(12) United States Patent
Cost et al.

(10) Patent No.: US 9,963,715 B2
(45) Date of Patent: May 8, 2018

(54) METHODS AND COMPOSITIONS FOR TREATMENT OF A GENETIC CONDITION

(71) Applicant: Sangamo BioSciences, Inc., Richmond, CA (US)

(72) Inventors: Gregory J. Cost, Richmond, CA (US); Philip D. Gregory, Richmond, CA (US); Dmitry Guschin, Richmond, CA (US); Michael C. Holmes, Richmond, CA (US); Jeffrey C. Miller, Richmond, CA (US); David Paschon, Richmond, CA (US); Edward J. Rebar, Richmond, CA (US); Andreas Reik, Richmond, CA (US); Fyodor Urnov, Richmond, CA (US); Lei Zhang, Richmond, CA (US)

(73) Assignee: Sangamo Therapeutics, Inc., Richmond, CA (US)

(*) Notice: Subject to any disclaimer, the term of this patent is extended or adjusted under 35 U.S.C. 154(b) by 256 days.

(21) Appl. No.: 14/013,236

(22) Filed: Aug. 29, 2013

(65) Prior Publication Data
US 2014/0093913 A1    Apr. 3, 2014

Related U.S. Application Data

(60) Provisional application No. 61/694,693, filed on Aug. 29, 2012.

(51) Int. Cl.
| | | |
|---|---|---|
| C12N 15/85 | (2006.01) | |
| C12N 15/52 | (2006.01) | |
| C12N 9/22 | (2006.01) | |
| C07K 14/47 | (2006.01) | |
| C07K 14/805 | (2006.01) | |

(52) U.S. Cl.
CPC .......... *C12N 15/85* (2013.01); *C07K 14/4702* (2013.01); *C07K 14/805* (2013.01); *C12N 9/22* (2013.01); *C12N 15/52* (2013.01); *C07K 2319/81* (2013.01)

(58) Field of Classification Search
CPC .... C07K 16/00; A01K 67/0278; A61K 39/35; C12N 15/85; C12N 15/52; C12N 9/22
See application file for complete search history.

(56) References Cited

U.S. PATENT DOCUMENTS

| | | | |
|---|---|---|---|
| 5,356,802 A | 10/1994 | Chandrasegaran | |
| 5,436,150 A | 7/1995 | Chandrasegaran | |
| 5,487,994 A | 1/1996 | Chandrasegaran | |
| 5,789,538 A | 8/1998 | Rebar et al. | |
| 5,925,523 A | 7/1999 | Dove et al. | |
| 6,007,988 A | 12/1999 | Choo | |
| 6,013,453 A | 1/2000 | Choo | |
| 6,140,081 A | 10/2000 | Barbas | |
| 6,140,466 A | 10/2000 | Barbas, III et al. | |
| 6,200,759 B1 | 3/2001 | Dove et al. | |
| 6,242,568 B1 | 6/2001 | Barbas, III et al. | |
| 6,410,248 B1 | 6/2002 | Greisman et al. | |
| 6,453,242 B1 | 9/2002 | Eisenberg et al. | |
| 6,479,626 B1 | 11/2002 | Kim et al. | |
| 6,503,717 B2 | 1/2003 | Case et al. | |
| 6,532,231 B1 | 3/2003 | Blumberg et al. | |
| 6,534,261 B1 | 3/2003 | Cox, III et al. | |
| 6,599,692 B1 | 7/2003 | Case et al. | |
| 6,607,882 B1 | 8/2003 | Cox, III et al. | |
| 6,689,558 B2 | 2/2004 | Case | |
| 6,794,136 B1 | 9/2004 | Eisenberg et al. | |
| 6,824,978 B1 | 11/2004 | Cox, III et al. | |
| 6,903,185 B2 | 6/2005 | Kim et al. | |
| 6,933,113 B2 | 8/2005 | Case et al. | |
| 6,979,539 B2 | 12/2005 | Cox, III et al. | |
| 7,013,219 B2 | 3/2006 | Case et al. | |
| 7,030,215 B2 | 4/2006 | Liu et al. | |
| 7,067,317 B2 | 6/2006 | Rebar et al. | |
| 7,070,934 B2 | 7/2006 | Cox, III et al. | |
| 7,153,949 B2 | 12/2006 | Kim et al. | |
| 7,163,824 B2 | 1/2007 | Cox, III et al. | |
| 7,253,273 B2 | 8/2007 | Collingwood | |
| 7,361,635 B2 | 4/2008 | Miller et al. | |
| 7,629,326 B2 | 12/2009 | Choulika et al. | |
| 7,888,121 B2 | 2/2011 | Urnov et al. | |
| 7,951,925 B2 | 5/2011 | Ando et al. | |
| 8,012,946 B1 | 9/2011 | Zhang et al. | |
| 8,110,379 B2 | 2/2012 | DeKelver et al. | |
| 8,383,604 B2 | 2/2013 | Orkin et al. | |
| 8,420,782 B2 | 4/2013 | Bonas et al. | |
| 8,440,431 B2 | 5/2013 | Voytas et al. | |
| 8,921,332 B2 | 12/2014 | Choulika et al. | |
| 2003/0232410 A1 | 12/2003 | Liljedahl et al. | |
| 2005/0026157 A1 | 2/2005 | Baltimore et al. | |

(Continued)

FOREIGN PATENT DOCUMENTS

| | | |
|---|---|---|
| GB | 2338237 | 12/1999 |
| WO | WO 95/19431 | 7/1995 |

(Continued)

OTHER PUBLICATIONS

Greisman et al. 1997, Science 275:657-661.*
Tan et al. 2003 PNAS, pp. 11997-12002.*
Rudinger, J., "Characteristics of the amino acids as components of a peptide hormone sequence",in Peptide Hormones, University Park Press: Baltimore, MD, pp. 1-7, 1976.*
Ngo, J. et al., "Computational Complexity, Protein Structure Prediction, and the Levinthal Paradox", 1994, The Protein Folding Problem and Tertiary Structure Prediction, Merz et al. (eds.), Birkhauser Boston: Boston, MA, pp. 491-495.*
Li et al Nature, Jul. 14, 2011, 475, 7355, 217-221.*
Porteus Nature Biotechnology, Aug. 2005, vol. 23, No. 8, 967-973.*
Hauschild (PNAS, 2011, 108( 29), 12013-12017.*
Funnell et al Blood, 126:89-93 (Year: 2015).*
Smith et al (Human Molecular Genetics, vol. 25, No. R2 R99-R105), (Year: 2016).*

(Continued)

*Primary Examiner* — Anoop K Singh
(74) *Attorney, Agent, or Firm* — Pasternak Patent Law; Susan Abrahamson

(57) ABSTRACT

Disclosed herein are nucleases and methods of using these nucleases for alteration of a globin gene and generation of cells.

11 Claims, 14 Drawing Sheets

(56) References Cited

U.S. PATENT DOCUMENTS

| | | |
|---|---|---|
| 2005/0064474 A1 | 3/2005 | Urnov et al. |
| 2005/0208489 A1 | 9/2005 | Carroll et al. |
| 2005/0267061 A1 | 12/2005 | Martin |
| 2006/0063231 A1 | 8/2006 | Guschin et al. |
| 2006/0188987 A1 | 8/2006 | Guschin et al. |
| 2007/0141038 A1 | 6/2007 | Choulika et al. |
| 2007/0218528 A1 | 9/2007 | Miller |
| 2008/0131962 A1 | 6/2008 | Miller |
| 2008/0159996 A1 | 7/2008 | Ando et al. |
| 2008/0299580 A1 | 12/2008 | DeKelver et al. |
| 2009/0068164 A1 | 3/2009 | Barbas et al. |
| 2009/0305419 A1 | 12/2009 | Miller |
| 2010/0047805 A1 | 2/2010 | Wang |
| 2010/0218264 A1 | 8/2010 | Cui et al. |
| 2010/0261271 A1 | 10/2010 | Cox, III et al. |
| 2011/0041195 A1 | 2/2011 | Doyon |
| 2011/0189775 A1 | 8/2011 | Ainley et al. |
| 2011/0201055 A1 | 8/2011 | Doyon et al. |
| 2011/0207221 A1 | 8/2011 | Cost et al. |
| 2011/0281361 A1 | 11/2011 | DeKelver et al. |
| 2011/0287512 A1 | 11/2011 | Paschon et al. |
| 2011/0301073 A1 | 12/2011 | Gregory et al. |
| 2012/0142062 A1 | 6/2012 | Doyon et al. |
| 2012/0230971 A1 | 10/2012 | Choulika et al. |
| 2013/0122591 A1 | 5/2013 | Cost et al. |
| 2013/0137104 A1 | 5/2013 | Cost et al. |
| 2013/0177960 A1 | 7/2013 | Rebar |
| 2013/0177983 A1 | 7/2013 | Rebar |
| 2013/0326645 A1 | 12/2013 | Cost et al. |
| 2015/0166969 A1* | 6/2015 | Takeuchi ............ A61K 38/465 435/196 |
| 2016/0010067 A1 | 1/2016 | Kock et al. |

FOREIGN PATENT DOCUMENTS

| | | |
|---|---|---|
| WO | WO 96/06166 | 2/1996 |
| WO | WO 98/37186 | 8/1998 |
| WO | WO 98/53057 | 11/1998 |
| WO | WO 98/53058 | 11/1998 |
| WO | WO 98/53059 | 11/1998 |
| WO | WO 98/53060 | 11/1998 |
| WO | WO 98/54311 | 12/1998 |
| WO | 2000/46386 A3 | 2/2000 |
| WO | WO 00/27878 | 5/2000 |
| WO | 0041566 A1 | 7/2000 |
| WO | WO 01/60970 | 8/2001 |
| WO | WO 01/88197 | 11/2001 |
| WO | WO 02/016536 | 2/2002 |
| WO | 200242459 A2 | 5/2002 |
| WO | WO 02/077227 | 10/2002 |
| WO | WO 02/099084 | 12/2002 |
| WO | WO 03/016496 | 2/2003 |
| WO | 2005014791 A2 | 2/2005 |
| WO | 2005100392 A2 | 10/2005 |
| WO | WO 2007/014275 | 2/2007 |
| WO | WO 2009/042163 | 4/2009 |
| WO | WO 2009/054985 | 4/2009 |
| WO | 2010030963 A2 | 3/2010 |
| WO | WO 2010/079430 | 7/2010 |
| WO | 2011097036 A1 | 8/2011 |
| WO | WO 2013/126794 | 8/2013 |
| WO | 2014186585 A2 | 11/2014 |

OTHER PUBLICATIONS

Glarneau et al Nature Genetics, 42:1049-1051 (Year: 2010).*
Baden et al Haematologica. 96(11):1712-4 (Year: 2011).*
U.S. Appl. No. 60/118,669, filed Feb. 3, 1999.
Beerli, et al., "Engineering Polydactyl Zinc-Finger Transcription Factors," *Nature Biotechnology* 20:135-141(2002).
Bieker, "Putting a Finger on the Switch," *Nat Genet* 42(9):733-734 (2010).
Boch, et al., "Breaking the Code of DNA Binding Specificity of TAL-Type III Effectors," *Science* 326:1509-1512 (2009).
Bonas, et al., "Genetic and Structural Characterization of the Avirulence Gene AVRBS3 From Xanthomonas Campestris PV. Vesicatoria," *Mol. Gen. Genet.* 218:127-136 (1989).
Borg, et al., "Haploinsufficiency for the Erythroid Transcription Factor KLF1 Causes Hereditary Persistence of Fetal Hemoglobin," *Nat Genet* 42(9):801-805 (2010).
Choo, et al., "Advanes in Zinc Finger Engineering," *Curr. Opin. Struct. Biol.* 10:411-416 (2000).
Chui, et al., "Hemoglobin H Disease: Not Necessarily a Benign Disorder," *Blood* 101(3):791 (2003).
Constantoulakis, et al., "Alpha Amino N Butyric Acid Stimulates Fetal Hemoglobin in the Adult," *Blood* 72(6):1961-1967 (1988).
DeSimone, "5-Azacytidine Stimulates Fetal Hemoglobin Synthesis in Anemic Baboons," *Proc. Natl. Acad. Sci. USA* 79(14):4428-4431 (1982).
Guschin, et al., "A Rapid and General Assay for Monitoring Endogenous Gene Modification," *Methods Mol. Biol.* 649:247-256 (2010).
Harteveld and Higgs, "A-Thalassaemia," *Orphanet Journal of Rare Diseases* 5:13 (2010).
Heuer, et al., "Repeat Domain Diversity of AVRBS3-Like Genes in Ralstonia Solanacearum Strains and Association With Host Preferences in the Field," *Appl. And Envir. Micro.* 73(13):4379-4384 (2007).
Holt, et al., "Human Hematopoietic Stem/Progenitor Cells Modified by Zinc-Finger Nucleases Targeted to CCR5 Control HIV-1 In Vivo," *Nat. Biotechnol.* 28(8):839-47 (2010).
Isalan, et al., "A Rapid, Generally Applicable Method to Engineer Zinc Fingers Illustrated by Targeting the HIV-1 Promoter," *Nat. Biotechnol.* 19:656-660 (2001).
Kay, et al., "A Bacterial Effector Acts As a Plant Transcription Factor and Induces a Cell Size Regulator," *Science* 318:648-651 (2007).
Kim, et al., "Chimeric Restriction Endonuclease," *PNAS USA* 91:883-887 (1994).
Kim, et al., "Insertion and Deletion Mutants of Foki Restriction Endonuclease," *J. Biol. Chem.* 269:31978-31982 (1994).
Ley, et al., "5-Azacytidine Increases Gamma-Globin Synthesis and Reduces the Proportion of Dense Cells in Patients With Sickle Cell Anemia," *Blood* 62:370-380 (1983).
Ley, et al., "5-Azacytidine Selectively Increases Γ-Globin Synthesis in a Patient With B+ Thalassemia," *N. Engl. J. Medicine* 307:1469-1475 (1982).
Li, et al., "Alteration of the Cleavage Distance of FOK I Restriction Endonuclease by Insertion Mutagenesis," *PNAS USA* 90:2764-2768 (1993).
Li, et al., "Functional Domains in FOK I Restriction Endonuclease," *PNAS USA* 89:4275-4279 (1992).
Moscou and Bogdanove, "A Simple Cipher Governs DNA Recognition by TAL Effectors," *Science* 326:1501 (2009).
Pabo et al., "Design and Selection of Novel CYS2HIS2 Zinc Finger Proteins," *Ann. Rev. Biochem.* 70:313-340 (2001).
Perez, et al., "Establishment of HIV-1 Resistance in CD4+ T Cells by Genome Editing Using Zinc-Finger Nucleases," *Nature Biotechnology* 26(7):808-816 (2008).
Sankaran, et al., "Human Fetal Hemoglobin Expression Is Regulated by the Developmental Stage-Specific Repressor BCL11A," *Science* 332:1839-1842 (2008).
Schomack, et al., "Gene-For-Gene-Mediated Recognition of Nuclear-Targeted AVRBS3-Like Bacterial Effector Proteins," *J. Plant Physiol.* 163(3):256-272 (2006).
Segal, et al., "Custom DNA-Binding Proteins Come of Age: Polydactyl Zinc-Finger Proteins," *Curr. Opin. Biotechnol.* 12:632-637 (2001).
Thein, et al., "Control of Fetal Hemoglobin: New Insights Emerging From Genomics and Clinical Implications," *Hum. Mol. Genet.* 18(R2):R216-R223 (2009).
Urnov, et al., "Highly Efficient Endogenous Human Gene Correction Using Designed Zinc-Finger Nucleases," *Nature* 435(7042):646-651 (2005).
Voon, et al., "Sirna-Mediated Reduction of A-Globin Results in Phenotypic Improvements in B-Thalassemic Cells," *Haematologica* 93(8):1238(2008).

(56) References Cited

OTHER PUBLICATIONS

Yang, et al., "Purification, Cloning, and Characterization of the CEL I Nuclease," *Biochemistry* 39:3533-3541 (2000).
Zhou, et al., "KLF1 Regulates BCL11A Expression and Γ- to B-Globin Gene Switching," *Nat Genet* 42(9):742-744 (2010).
Holt, et al., "Human Hematopoietic Stem/ Progenitor Cells Modified by Zinc-Finger Nucleases Targetd to CCR5 Control HIV-1 In Vivo," Nature Biotechnology 28(8):839-847 (2010).
Li, et al., "Progress on Applications of Zinc Finger Nuclease Technology in Gene Therapy," Journal of Northwest A&F University 39(6):50-60 (2011) (English translation of Abstract only).
Sankaran, et al., "Transcriptional Silencing of Fetal Hemoglobim by BCL11A," Annals of the New York Academy of Sciences 1202:64-68 (2010).
Sankaran, et al., "Human Fetal Hemoglobin Expression Is Regulated by the Developmental Stage-Specific Represso BCL11A," Science 322(5909)1839-1842 (2008).
Bauer, et al., "Reawakening Fetal Hemoglobin: Prospects for New Therapies for the Beta-Globin Disorders," Blood 120(15):2945-2953 (2012).
Bauer, et al., "Update on Fetal Hemoglobin Gene Regulation in Hemoglobinopathies," Current Opinion in Pediatrics 23(1): 1-8 (2011).
Sankaran, et al., "Developmental and Species-Divergent Globin Switching Are Driven by BCL11A," Nature 460(7259):1093-1097 (2009).
Sebastiano, et al., "In Situ Genetic Correction of the Sickle Cell Anemia Mutation in Human Induced Pluripotent Stem Cells Using Engineered Zinc Finger Nucleaes," Stem Cells 29(11):1717-1726 (2011).
Sedgewick, et al., "BCL11A Is a Major HBF Quantitative Trait Locus in Three Different Populations With Beta-Hemoglobinopathies," Blood Cells, Molecules and Diseases 41(3):255-258 (2008).
Sun, et al.,"Optimized TAL Effector Nucleases (TALENS) for Use in Treatment of Sickle Cell Disease," Molecular Biosystems 8(4):1255 (2012).
Uda, et al., "Genome-Wide Association Study Shows BCL11A Associated With Persistent Fetak Hemoglobin and Amelioration of the Phenotype of Beta-Thalassemia," PNAS USA 105(5):1620-1625 (2008).
Urnov, et al., "Genome Editing With Engineered Zinc Finger Nucleases," Nature Reviews Genetics 11(9):636-646 (2010).
Wayengera, "Zinc Finger Nucleases for Targeted Mutagenesis and Repair of the Sickle-Cell Disease Mutation: An In-Silico Study," BMC Blood Disorders, 12(5):1-8 (2012).

* cited by examiner

β-thal: G → A

Sickle

C→T: 9-18%

```
           exon 1
HBB_S   1043  CAGACACC ATG GTGCAC CTGACTC C TGAGGAGAAGTCTGCCGTTA C T GGGCAAGGTGAACGTGGATGAAGTTGGTGGTGAGGCCCTGGGCAGGT
HBB     1043  CAGACACC ATG GTGCAC CTGACTC C TGAGGAGAAGTCTGCCGTTA C T GGGCAAGGTGAACGTGGATGAAGTTGGTGGTGAGGCCCTGGGCAGGT
HBD     1188  CAGACACC ATG GTGCAT CTGACT G CCTGAGGAGAAGTCTGCCGTTA C T GGGCAAGGTGAACGTGAACGTTGATGAAGTTGGTGGTGAGGCCCTGGGCAG
HBBP1   1045  C ATGACA G T GTAGC AT CTACTCC CTGTCTGCCTATTGGTCTATTTTCCCACCCCTAGGCTGCTGGTGGTCTACCCTTGGACCCAGAGGTTCTTTGAGTCC
HBE1    1246  CAGAC AC CCATGG G TACCT TACTCC CTTCT CTGCCCT G CAAGGACTAC CTGCA CAACAAGAATGTGGTGATC CTGGC TGGAGGAAGGTGGGCAGGT
HBG1    1046  CAGAC G CCATGG G TCATT TACTCC CTTCT CTGCCTCT G C AA CTAC TATGGGGTGAATGATAC TGGAAGGTGAAGATAC CTGGAGGAGAAGGGGCAGGT
HBG2    1046  CAGAC G CCATGG G TCATT TACTCC CTTCT CTGCCTCT G C AA CTAC TATGGGGTGAATGATAC TGGAAGGTGAAGATAC CTGGAGGAGAAGGGGCAGGT
``` locus 3: 35256; 35263
locus 4: 34770; 34791
locus 5: 34805; 34826
locus 7: 35301; 35328
locus 8: 35497; 35506

| Locus | % indels, CD34 studies | |
|---|---|---|
| | exp 1 | exp 2 |
| 3 | 13.3 | 0.0 |
| 4 | 0.0 | 0.0 |
| 5 | 36.8 | 25.6 |
| 6 | 42.0 | 23.7 |
| 7 | 23.2 | 19.9 |

FIGURE 1

A. RFLP

B. CEL-I

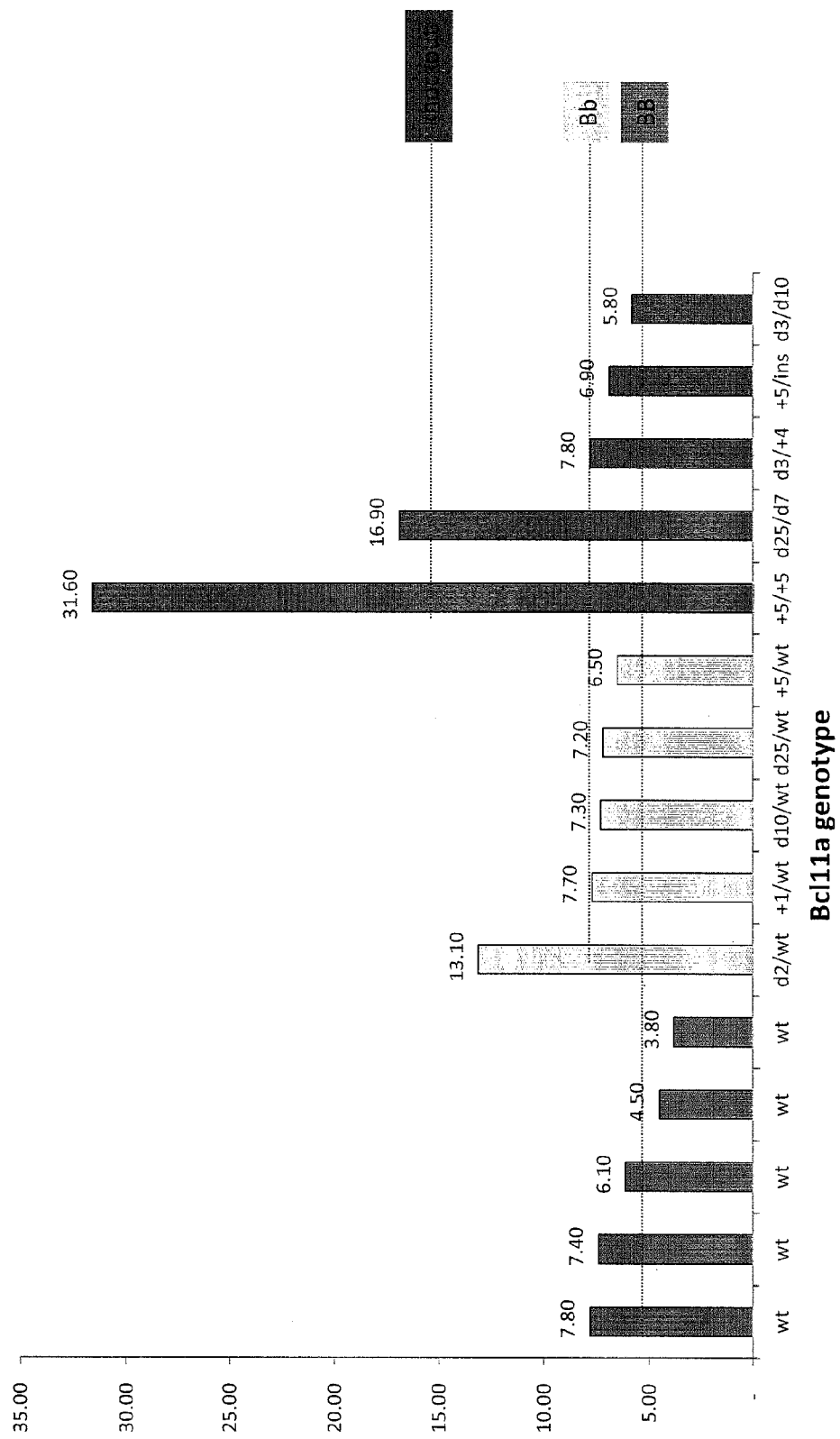

```
Reference    GGCCAGCCCTTGCCTTGACCAATAGCCCTTGACAAGGCAAACTTGACCAATAG wt (26)      GGCCAGCCCTTGCCTTGACCAATAGCCCTTGACAAGGCAAACTTGACCAATAG
Δ1bp (1)     GGCCAGCCCTTGCCTTGACC-ATAGCCCTTGACAAGGCAAACTTGACCAATAG
Δ4bp (1)     GGCCAGCCCTTGCCTTT----AATAGCCCTTGACAAGGCAAACTTGACCAATAG
Δ6bp (2)     GGCCAGCCCTTGCCTTGAC------CCTTGACAAGGCAAACTTGACCAATAG
Δ6bp (1)     GGCCAGCCCTTGCCTTGACCAATAGC------AAGGCAAACTTGACCAATAG
Δ13bp (9)    GGCCAGCCCTTGCCTTGAC-------------AAGGCAAACTTGACCAATAG
+1bp (1)     GGCCAGCCCTTGCCTTGACCAATAGCCCTTGACAAGGCAAACTTGACCAATA
+3bp (1)     GGCCAGCCCTTGCCTTGACCAATAGCAGCCTTGACAAGGCAAACTTGACCAA
+5bp (3)     GGCCAGCCCTTGCCTTGACCAATAGAATAGCCCTTGACAAGGCAAACTTGACC
```

METHODS AND COMPOSITIONS FOR TREATMENT OF A GENETIC CONDITION

CROSS-REFERENCE TO RELATED APPLICATIONS

The present application claims the benefit of U.S. Provisional Application No. 61/694,693, filed Aug. 29, 2012, the disclosure of which is hereby incorporated by reference in its entirety.

TECHNICAL FIELD

The present disclosure is in the field of genome engineering of hematopoietic stem cells, especially for the treatment of a hemoglobinopathy.

BACKGROUND

Gene therapy holds enormous potential for a new era in human medicine. These methodologies will allow treatment for conditions that heretofore have not been addressable by standard medical practice. One area that is especially promising is the ability to genetically engineer a cell to cause that cell to express a product not previously being produced in that cell. Examples of uses of this technology include the insertion of a gene encoding a novel therapeutic protein, insertion of a coding sequence encoding a protein that is lacking in the cell or in the individual, insertion of a wild type gene in a cell containing a mutated gene sequence, and insertion of a sequence that encodes a structural nucleic acid such as a microRNA or siRNA.

Transgenes can be delivered to a cell by a variety of ways, such that the transgene becomes integrated into the cell's own genome and is maintained there. In recent years, a strategy for transgene integration has been developed that uses cleavage with site-specific nucleases for targeted insertion into a chosen genomic locus (see, e.g., co-owned U.S. Pat. No. 7,888,121). Nucleases specific for targeted genes can be utilized such that the transgene construct is inserted by either homology directed repair (HDR) or by end capture during non-homologous end joining (NHEJ) driven processes. Targeted loci include "safe harbor" loci for example a CCR5 gene, a CXCR4 gene, a PPP1R12C (also known as AAVS1) gene, an albumin gene or a Rosa gene. See, e.g., U.S. Patent Publication Nos. 20080299580; 20080159996; 201000218264; 20110301073; 20130177983; 20130177960 and 20150056705. Nuclease-mediated integration offers the prospect of improved transgene expression, increased safety and expressional durability, as compared to classic integration approaches that rely on random integration of the transgene, since it allows exact transgene positioning for a minimal risk of gene silencing or activation of nearby oncogenes.

Red blood cells (RBCs), or erythrocytes, are the major cellular component of blood. In fact, RBCs account for one quarter of the cells in a human. Mature RBCs lack a nucleus and many other organelles in humans, and are full of hemoglobin, a metalloprotein found in RBCs that functions to carry oxygen to the tissues as well as carry carbon dioxide out of the tissues and back to the lungs for removal. The protein makes up approximately 97% of the dry weight of RBCs and it increases the oxygen carrying ability of blood by about seventy fold. Hemoglobin is a heterotetramer comprising two α-like globin chains and two β-like globin chains and 4 heme groups. In adults the α2β2 tetramer is referred to as Hemoglobin A (HbA) or adult hemoglobin. Typically, the alpha and beta globin chains are synthesized in an approximate 1:1 ratio and this ratio seems to be critical in terms of hemoglobin and RBC stabilization. In fact, in some cases where one type of globin gene is inadequately expressed (see below), reducing expression (e.g. using a specific siRNA) of the other type of globin, restoring this 1:1 ratio, alleviates some aspects of the mutant cellular phenotype (see Voon et at (2008) *Haematologica* 93(8):1288). In a developing fetus, a different form of hemoglobin, fetal hemoglobin (HbF) is produced which has a higher binding affinity for oxygen than Hemoglobin A such that oxygen can be delivered to the baby's system via the mother's blood stream. Fetal hemoglobin also contains two α globin chains, but in place of the adult β-globin chains, it has two fetal γ-globin chains (i.e., fetal hemoglobin is α2γ2). At approximately 30 weeks of gestation, the synthesis of γ globin in the fetus starts to drop while the production of β globin increases. By approximately 10 months of age, the newborn's hemoglobin is nearly all α2β2 although some HbF persists into adulthood (approximately 1-3% of total hemoglobin). The regulation of the switch from production of γ to β is quite complex, and primarily involves an expressional down-regulation of γ globin with a simultaneous up-regulation of β globin expression.

Genetic defects in the sequences encoding the hemoglobin chains can be responsible for a number of diseases known as hemoglobinopathies, including sickle cell anemia and thalassemias. In the majority of patients with hemoglobinopathies, the genes encoding γ globin remain present, but expression is relatively low due to normal gene repression occurring around parturition as described above.

It is estimated that 1 in 5000 people in the U.S. have sickle cell disease (SCD), mostly in people of sub-Saharan Africa descent. There appears to be a benefit of sickle cell heterozygosity for protection against malaria, so this trait may have been selected for over time, such that it is estimated that in sub-Saharan Africa, one third of the population has the sickle cell trait. Sickle cell disease is caused by a mutation in the β globin gene in which valine is substituted for glutamic acid at amino acid #6 (a GAG to GTG at the DNA level), where the resultant hemoglobin is referred to as "hemoglobin S" or "HbS." Under lower oxygen conditions, a conformational shift in the deoxy form of HbS exposes a hydrophobic patch on the protein between the E and F helices. The hydrophobic residues of the valine at position 6 of the beta chain in hemoglobin are able to associate with the hydrophobic patch, causing HbS molecules to aggregate and form fibrous precipitates. These aggregates in turn cause the abnormality or 'sickling' of the RBCs, resulting in a loss of flexibility of the cells. The sickling RBCs are no longer able to squeeze into the capillary beds and can result in vaso-occlusive crisis in sickle cell patients. In addition, sickled RBCs are more fragile than normal RBCs, and tend towards hemolysis, eventually leading to anemia in the patient.

Treatment and management of sickle cell patients is a life-long proposition involving antibiotic treatment, pain management and transfusions during acute episodes. One approach is the use of hydroxyurea, which exerts its effects in part by increasing the production of γ globin. Long term side effects of chronic hydroxyurea therapy are still unknown, however, and treatment gives unwanted side effects and can have variable efficacy from patient to patient. Despite an increase in the efficacy of sickle cell treatments, the life expectancy of patients is still only in the mid to late 50's and the associated morbidities of the disease have a profound impact on a patient's quality of life.

Thalassemias are also diseases relating to hemoglobin and typically involve a reduced expression of globin chains. This can occur through mutations in the regulatory regions of the genes or from a mutation in a globin coding sequence that results in reduced expression. Alpha thalassemias are associated with people of Western Africa and South Asian descent, and may confer malarial resistance. Beta thalassemia is associated with people of Mediterranean descent, typically from Greece and the coastal areas of Turkey and Italy. Treatment of thalassemias usually involves blood transfusions and iron chelation therapy. Bone marrow transplants are also being used for treatment of people with severe thalassemias if an appropriate donor can be identified, but this procedure can have significant risks.

One approach for the treatment of both SCD and beta thalassemias that has been proposed is to increase the expression of γ globin with the aim to have HbF functionally replace the aberrant adult hemoglobin. As mentioned above, treatment of SCD patients with hydroxyurea is thought to be successful in part due to its effect on increasing γ globin expression. The first group of compounds discovered to affect HbF reactivation activity were cytotoxic drugs. The ability to cause de novo synthesis of gamma-globin by pharmacological manipulation was first shown using 5-azacytidine in experimental animals (DeSimone (1982) *Proc Natl Acad Sci USA* 79(14):4428-31). Subsequent studies confirmed the ability of 5-azacytidine to increase HbF in patients with β-thalassemia and sickle cell disease (Ley, et al., (1982) *N. Engl. J. Medicine,* 307: 1469-1475, and Ley, et al., (1983) *Blood* 62: 370-380). In addition, short chain fatty acids (e.g. butyrate and derivatives) have been shown in experimental systems to increase HbF (Constantoulakis et al., (1988) *Blood* 72(6):1961-1967). Also, there is a segment of the human population with a condition known as 'Hereditary Persistence of Fetal Hemoglobin' (HPFH) where elevated amounts of HbF persist in adulthood (10-40% in HPFH heterozygotes (see Thein et al (2009) *Hum. Mol. Genet* 18 (R2): R216-R223). This is a rare condition, but in the absence of any associated beta globin abnormalities, is not associated with any significant clinical manifestations, even when 100% of the individual's hemoglobin is HbF. When individuals that have a beta thalassemia also have co-incident HPFH, the expression of HbF can lessen the severity of the disease. Further, the severity of the natural course of sickle cell disease can vary significantly from patient to patient, and this variability, in part, can be traced to the fact that some individuals with milder disease express higher levels of HbF.

One approach to increase the expression of HbF involves identification of genes whose products play a role in the regulation of γ globin expression. One such gene is BCL11A, first identified because of its role in lymphocyte development. BCL11A encodes a zinc finger protein that is thought to be involved in the stage specific regulation of γ globin expression. BCL11A is expressed in adult erythroid precursor cells and down-regulation of its expression leads to an increase in γ globin expression. In addition, it appears that the splicing of the BCL11A mRNA is developmentally regulated. In embryonic cells, it appears that the shorter BCL11A mRNA variants, known as BCL11A-S and BCL11A-XS are primary expressed, while in adult cells, the longer BCL11A-L and BCL11A-XL mRNA variants are predominantly expressed. See, Sankaran et al (2008) *Science* 322 p. 1839-1842. The BCL11A protein appears to interact with the β globin locus to alter its conformation and thus its expression at different developmental stages. In addition, another regulatory protein KLF1, appears to be involved in regulation of γ globin expression. It has been found that KLF1 levels are directly proportional to BCL11A levels, and both are inversely proportional to γ globin levels. For example, in a Maltese family with persistent expression of HbF, the family carries a heterozygous mutation of the KLF1 gene (Borg et al (2010) *Nat Genet,* 42(9):801-805). The KLF1 gene product appears to bind directly to the BCL11A gene in vivo, and thus may be responsible for its upregulation (see Borg et al. ibid; Bieker (2010) *Nat Genet* 42(9): 733-734; Zhou et al. (2010) *Nat Genet* 42(9):742-744). Thus, if KLF1 stimulates BCL11A expression, the action of that induced BCL11A will result in the suppression of γ globin and HbF production. Use of an inhibitory RNA targeted to the BCL11A gene has been proposed (see, e.g., U.S. Patent Publication 20110182867) but this technology has several potential drawbacks, namely that complete knock down may not be achieved, delivery of such RNAs may be problematic and the RNAs must be present continuously, requiring multiple treatments for life.

Alpha thalassemias are also prevalent in the human population, especially in Asia and some type of alpha globin aberrancy is thought to be the commonest genetic disorder in humans. In the tropical and subtropical areas of the world, alpha globin disorder is found in 80-90% of the population (see Harteveld and Higgs (2010) *Orphanet Journal of Rare Diseases* 5:13).

Humans carry 2 copies of the alpha globin gene in tandem (α1 and α2) on chromosome 16, so in a normal diploid cell there are 4 copies all together. The α2 gene normally accounts for 2-3 times more α-globin mRNA than the α1 gene. The tandem organization of these two genes may be associated with the high prevalence of large deletions in alpha globin genes in alpha thalessemia patients, where generally the number of alpha globin genes that are non-functional relates directly to the severity of any alpha thalassemia (see Chui et al (2003) *Blood* 101(3):791). Deletion of one copy seems to be fairly common (30% of African Americans and 60-80% of people living in Saudi Arabia, India, and Thailand), and is generally not evident in the individual unless genetic testing is done. Deletion of two copies, whether on the same chromosome (cis) or one from each chromosome (trans), may cause the afflicted person to have mild anemia. When three a globin genes are deleted, such that the individual has only one functioning α globin gene, moderate anemia is found, but more importantly, the crucial α globin to β globin ratio is disrupted. β4 tetramers, comprising four beta globin chains, are often observed in patients with only one functional alpha globin gene, an condition known as HbH. The β4 tetramers are able to bind oxygen but do not release it into the periphery, causing what is known as HbH disease. Individuals with HbH disease have RBCs with shortened half-lives and which undergo hemolysis easily, leading to increased anemia. Loss of all four a globin genes is usually fatal in utero.

Thus, there remains a need for additional methods and compositions that can be used for genome editing, to correct an aberrant gene or alter the expression of others for example to treat hemoglobinopathies such as sickle cell disease and thalassemia.

SUMMARY

Disclosed herein are methods and compositions for altering the expression or for correcting one or more genes encoding proteins involved in a genetic disease (e.g., producing proteins lacking, deficient or aberrant in the disease and/or proteins that regulate these proteins) such as sickle cell disease or a thalassemia. Alteration of such proteins can result in the treatment of these genetic diseases. In particular, genome editing is used to correct an aberrant gene, insert a wild type gene, or change the expression of an endogenous gene. By way of non-limiting example, a wild type gene encoding β globin may be inserted into a cell to produce a protein lacking in and/or treat a hemoglobinopathy caused by faulty β globin. In some instances, the wild type gene may be inserted into a safe harbor locus or at a locus known to be highly expressed in a tissue of interest such as the β globin locus in erythroid cells. Genome editing may be similarly used to produce a protein lacking (and thereby treat) an alpha thalessemia by insertion of a wild type alpha globin gene into a safe harbor. Another approach involves the use of gene correction where a faulty endogenous α or β globin gene is targeted and the mutant sequence replaced. Alternately, a regulatory gene involved in repression of γ globin may be altered or knocked out (e.g., to increase expression of γ globin by inactivating and/or reducing the amount of the repressive protein) and/or the regulatory binding site upstream of the γ globin gene or in other areas of the beta-globin locus may be altered so that the regulators cannot interact properly at the γ globin locus and HbF is produced, thereby abrogating the effects (i.e. SCD or β-thalassemia) caused by the aberrant β globin gene. One approach further involves the use of modification of a stem cell (e.g., hematopoietic stem cell or RBC precursor), which stem cell can then be used to engraft into a patient, for treatment of a hemoglobinopathy.

In one aspect, described herein is a zinc-finger protein (ZFP) that binds to target site in a region of interest (e.g., a β globin, α globin or safe harbor gene, or a regulatory gene or its DNA target such as BCL11A, γ globin or KLF1) in a genome, wherein the ZFP comprises one or more engineered zinc-finger binding domains. In one embodiment, the ZFP is a zinc-finger nuclease (ZFN) that cleaves a target genomic region of interest, wherein the ZFN comprises one or more engineered zinc-finger binding domains and a nuclease cleavage domain or cleavage half-domain. Cleavage domains and cleavage half domains can be obtained, for example, from various restriction endonucleases and/or homing endonucleases. In one embodiment, the cleavage half-domains are derived from a Type IIS restriction endonuclease (e.g., Fok I). In certain embodiments, the zinc finger domain recognizes a target site in a globin or safe harbor gene. In certain embodiments, the zinc finger domain comprises 5 or 6 zinc finger domains and recognizes a target site in a globin gene (e.g., a zinc finger protein having 5 or 6 fingers with the recognition helix regions shown in Table 1A). In another embodiment, the zinc finger domain recognizes a target site in a BCL11A, KLF1, α, β or γ globin gene or their regulatory elements. In certain embodiments, the zinc finger domain comprises 5 or 6 zinc finger domains and recognizes a target site in a BCL11A, KLF1, α, β or γ globin gene or in their regulatory elements (e.g., a zinc finger protein having 5 or 6 fingers with the recognition helix regions shown in Table 1A).

In another aspect, described herein is a TALE protein (Transcription activator like) that binds to target site in a region of interest (e.g., an α or β globin or safe harbor gene, or a regulatory gene or its DNA target such as BCL11A, γ globin or KLF1) in a genome, wherein the TALE comprises one or more engineered TALE binding domains. In one embodiment, the TALE is a nuclease (TALEN) that cleaves a target genomic region of interest, wherein the TALEN comprises one or more engineered TALE DNA binding domains and a nuclease cleavage domain or cleavage half-domain. Cleavage domains and cleavage half domains can be obtained, for example, from various restriction endonucleases and/or homing endonucleases. In one embodiment, the cleavage half-domains are derived from a Type IIS restriction endonuclease (e.g., Fok I). In certain embodiments, the TALE DNA binding domain recognizes a target site in a globin or safe harbor gene. In other embodiments, the TALE DNA binding domain recognizes a target site in a BCL11A, KLF1, α, β or γ globin gene or in their regulatory elements (e.g., a TALEN protein exemplified in Table 3).

In another aspect, described herein is a CRISPR/Cas system that binds to target site in a region of interest (e.g., a highly expressed gene, a disease associated gene or a safe harbor gene) in a genome, wherein the CRISPR/Cas system comprises a CRIPSR/Cas nuclease and an engineered crRNA/tracrRNA (or single guide RNA). In certain embodiments, the CRISPR/Cas system recognizes a target site in a highly expressed, disease associated, or safe harbor gene. In certain embodiments, the CRISPR/Cas system recognizes a target in a globin, albumin, CCR5, CXCR4, AAVS1, Rosa, or HPRT gene.

The ZFNs, TALENs and/or CRISPR/Cas system as described herein may bind to and/or cleave the region of interest in a coding or non-coding region within or adjacent to the gene, such as, for example, a leader sequence, trailer sequence or intron, or within a non-transcribed region, either upstream or downstream of the coding region. In certain embodiments, the ZFNs, TALENs and/or CRISPR/Cas system binds to and/or cleave a globin gene. In other embodiments, the ZFNs, TALENs and/or CRISPR/Cas system binds to and/or cleaves a safe-harbor gene, for example a CCR5 gene, a CXCR4 gene, a PPP1R12C (also known as AAVS1) gene, an albumin gene or a Rosa gene. See, e.g., U.S. Patent Publication Nos. 20080299580; 20080159996; 201000218264; 20110301073; 20130177983; 20130177960 and 20150056705. In addition, to aid in selection, the HPRT locus may be used (see U.S. Patent Publication No. 20130122591). In another aspect, described herein are compositions comprising one or more of the zinc-finger and/or TALE nucleases or CRISPR/Cas system as described herein. In some embodiments, the ZFNs, TALENs and/or CRISPR/Cas system binds to and cleaves a BCL11A, KLF1, α, β or γ globin gene or cleaves in their regulatory elements. In another aspect, described herein are compositions comprising one or more of the zinc-finger, TALE or Cas nucleases as described herein.

In another aspect, described herein is a polynucleotide encoding one or more ZFNs, TALENs and/or CRISPR/Cas system as described herein. The polynucleotide may be, for example, mRNA. In some aspects, the mRNA may be chemically modified (See e.g. Kormann et al, (2011) *Nature Biotechnology* 29(2):154-157).

In another aspect, described herein is a ZFN, TALEN and/or CRISPR/Cas system expression vector comprising a polynucleotide, encoding one or more ZFNs, TALENs and/or CRISPR/Cas system described herein, operably linked to a promoter. In one embodiment, the expression vector is a viral vector.

In one aspect, described herein is a ZFN, TALEN and/or CRISPR/Cas system protein that is used to cleave a target DNA.

In other aspects, genetically modified RBC precursors (hematopoietic stem cells known as "HSCs") are given in a bone marrow transplant and the RBCs differentiate and mature in vivo. In some embodiments, the HSCs are isolated following G-CSF-induced mobilization, and in others, the cells are isolated from human bone marrow or umbilical cords. In some aspects, the HSCs are edited by treatment with a nuclease designed to knock out a globin expressional regulator (e.g., BCL11A or KLF1). In other aspects, the HSCs are modified with an engineered nuclease and a donor nucleic acid such that a wild type gene (e.g., globin gene) is inserted and expressed and/or an endogenous aberrant gene is corrected. In some cases, the wild type gene sequence for insertion encodes a wild type β globin or a wild type α globin. In other cases, the endogenous aberrant gene is the β globin or the α globin gene. In some embodiments, the modified HSCs are administered to the patient following mild myeloablative pre-conditioning. In other aspects, the HSCs are administered after full myeloablation such that following engraftment, 100% of the hematopoietic cells are derived from the modified HSCs.

In another aspect, described herein is a method for cleaving an endogenous gene (e.g., a gene whose inactivation results in increased gamma globin expression such as BCL11A or KLF1) in an RBC precursor cell, the method comprising: introducing, into the cell, one or more polynucleotides encoding one or more ZFNs, TALENs and/or a CRISPR/Cas system that binds to a target site in the one or more endogenous genes under conditions such that the ZFN(s), TALENs and/or CRISPR/Cas system is (are) expressed and the one or more genes are cleaved. In another aspect, described herein is a method for cleaving a BCL11A or KLF1 gene in a cell, the method comprising: introducing, into the cell, one or more polynucleotides encoding one or more ZFNs, TALENs and/or CRISPR/Cas systems that bind to a target site in the one or more BCL11A or KLF1 genes under conditions such that the ZFN(s), TALENs and/or CRISPR/Cas system is (are) expressed and the one or more BCL11A or KLF1 genes are cleaved. In certain embodiments, the zinc finger domain comprises 5 or 6 zinc finger domains and recognizes a target site in a globin gene (e.g., a zinc finger protein having 5 to 6 fingers with the recognition helix regions shown in Table 1A). In other embodiments the TALEN recognizes a target site in a β globin, α-globin, gamma globin, KLF or BCL11A sequence (exemplified in Table 3). In still other embodiments, the CRIPSR/Cas system recognizes a target site in a β globin, α globin, gamma globin, KLF or BCL11A sequence wherein the single guide RNA is engineered to recognize a desired target site in the target gene of interest. The cleaved gene(s) may be inactivated (knockout), for example knockout of one or more genes whose product(s) may inhibit expression of a gene (e.g., globin gene), or the disruption of the regulatory target site on the DNA for such proteins. In some embodiments, the inactivated gene(s) or their target sequences are those involved in inhibiting the expression of fetal hemoglobin. Cells (e.g., stem cells) when differentiated contain fetal hemoglobin and can be given to patients in need thereof. In some embodiments, a globin gene is knocked out. For example an alpha globin gene may be knocked out to restore the alpha globin to beta globin ratio when a beta globin is poorly expressed, or an HbS encoding beta globin gene may be knocked out concomitant with insertion of a wild type beta globin. The cells (e.g., stem cells) when differentiated will contain HbA hemoglobin and can be given to patients in need thereof.

In another aspect, described herein is a method for inserting a sequence into an endogenous gene (e.g., a beta globin, alpha globin and/or safe harbor gene) in a cell (e.g. stem cell), the method comprising cleaving the endogenous gene using one or more nucleases and inserting a sequence into the cleavage site. In certain embodiments, a genomic sequence in any target gene is replaced, for example using a ZFN or TALEN pair, or a CRIPSR/Cas system (or vector encoding said ZFN, TALEN and/or CRIPSR/Cas system) as described herein and a "donor" sequence (also known as a "transgene") that is inserted into the gene following targeted cleavage with the ZFN, TALEN and/or a CRIPSR/Cas system. The donor sequence may be present in the ZFN or TALEN vector, present in a separate vector (e.g., Ad, AAV or LV vector) or, alternatively, may be introduced into the cell using a different nucleic acid delivery mechanism. Such insertion of a donor nucleotide sequence into the target locus (e.g., globin gene, other safe-harbor gene, etc.) results in the expression of the transgene under control of the target locus's (e.g. globin's) genetic control elements. In some embodiments, the transgene encodes a non-coding RNA (e.g., an shRNA). Expression of the transgene prior to RBC maturation will result in a RBC containing the non-coding RNA of interest.

In other embodiments, the transgene comprises a functional protein, for example a globin (e.g., wild type beta and/or wild type gamma) protein. In some embodiments, insertion of the transgene of interest into an endogenous gene (e.g., a globin gene), results in expression of an intact exogenous protein sequence and lacks any sequences encoded by the endogenous gene. In other embodiments, the expressed exogenous protein is a fusion protein and comprises amino acids encoded by the transgene and by a globin gene (e.g., from the endogenous target locus or, alternatively from globin-encoding sequences on the transgene). In some instances, the globin gene is a beta globin, while in other instances, the globin gene is an alpha globin. In other instances, the globin gene is a gamma globin gene. When present, endogenous globin sequences may be present on the amino (N)-terminal portion of the exogenous protein and/or the carboxy (C)-terminal portion of the exogenous protein. The globin sequences may include full-length wild-type or mutant globin sequences or, alternatively, may include partial globin coding sequences. In some embodiments, the globin-transgene fusion is located at the endogenous locus within the cell while in other embodiments, the globin-transgene coding sequence is inserted into a safe harbor within a genome. In some aspects, the safe harbor is selected from a CCR5 gene, a CXCR4 gene, a PPP1R12C (also known as AAVS1) gene, an albumin gene or a Rosa gene. See, e.g., U.S. Patent Publication Nos. 20080299580; 20080159996; 201000218264; 20110301073; 20130177983; 20130177960 and 20150056705. In addition, to aid in selection, the HPRT locus may be used (see U.S. Patent Publication No. 20130122591).

In yet another aspect, provided herein are cell lines and/or transgenic animal models (systems.) In some embodiments, the transgenic cell and/or animal includes a transgene that encodes a human gene. In some instances, the transgenic animal comprises a knock-out at the endogenous locus corresponding to exogenous transgene (e.g., the mouse globin gene is knocked out and the human globin gene is inserted into a mouse), thereby allowing the development of an in vivo system where the human protein may be studied in isolation. Such transgenic models may be used for screening purposes to identify small molecules or large biomolecules or other entities which may interact with or modify the human protein of interest. In some aspects, the transgene is integrated into the selected locus (e.g., globin or safe-harbor) into a stem cell (e.g., an embryonic stem cell, an induced pluripotent stem cell, a hematopoietic stem cell, etc.) or animal embryo obtained by any of the methods described herein, and then the embryo is implanted such that a live animal is born. In other aspects, the stem cells contain genomic alterations at endogenous loci such as the BCL11A, KLF1 or γ globin genes, or combinations thereof, such that γ globin expression is elevated. In some embodiments, the elevation of γ globin expression alters the ratio of γ globin to β globin in the cell as compared to the unedited stem cell. The animal is then raised to sexual maturity and allowed to produce offspring wherein at least some of the offspring comprise edited endogenous gene sequence or the integrated transgene.

In a still further aspect, provided herein is a method for site specific integration of a nucleic acid sequence into an endogenous locus (e.g., globin or safe harbor gene) of a chromosome, for example into the chromosome of an embryo. In certain embodiments, the method comprises: (a) injecting an embryo with (i) at least one DNA vector, wherein the DNA vector comprises an upstream sequence and a downstream sequence flanking the nucleic acid sequence to be integrated, and (ii) at least one RNA molecule encoding a zinc finger, TALE or Cas9 nuclease. In the case of using a Cas9 protein, an engineered sgRNA is also introduced. The nuclease or nuclease system recognizes the target site in the target locus (e.g., globin or safe harbor locus), and then (b) the embryo is cultured to allow expression of the zinc finger or TALE nuclease and/or CRISPR/Cas system, wherein a double stranded break is introduced into the target by the zinc finger nuclease, TALEN or CRISPR/Cas system is then repaired, via homologous recombination with the DNA vector, so as to integrate the nucleic acid sequence into the chromosome.

In any of the methods described herein, the polynucleotide encoding the zinc finger nuclease(s), TALEN(s) and/or CRIPSR/Cas system can comprise DNA, RNA or combinations thereof. In certain embodiments, the polynucleotide comprises a plasmid. In other embodiments, the polynucleotide encoding the nuclease comprises mRNA.

A kit, comprising the ZFPs, TALENs and/or CRIPSR/Cas system of the invention, is also provided. The kit may comprise nucleic acids encoding the ZFPs, TALENs or CRISPR/Cas system, (e.g. RNA molecules or ZFP, TALEN or Cas9 encoding genes contained in a suitable expression vector) and engineered sg RNA if needed, or aliquots of the nuclease proteins, donor molecules, suitable host cell lines, instructions for performing the methods of the invention, and the like.

These and other aspects will be readily apparent to the skilled artisan in light of disclosure as a whole.

BRIEF DESCRIPTION OF THE DRAWINGS

FIG. 1 depicts an alignment of the β like globin gene sequence in the region surrounding the sickle cell disease mutation (indicated on the figure). Shown (top line to bottom line) are hemoglobin beta sequences with the sickle cell mutation (HBB-sickle, SEQ ID NO:1); hemoglobin beta (HBB, SEQ ID NO:2); hemoglobin delta (HBD, SEQ ID NO:3); a beta hemoglobin pseudo gene (HBBP1, SEQ ID NO:4); hemoglobin epsilon (HBE1, SEQ ID NO:5), hemoglobin gamma 1 (HBG1, SEQ ID NO:6) and hemoglobin gamma 2 (HBG2, SEQ ID NO:7). The results of the Cel I activity analysis are shown below the alignment for the five ZFN pairs indicated.

FIG. 2A (RFLP) depicts insertion of a sequence specified by a β globin donor where the insertion is verified by the presence of a novel restriction site present on the donor DNA. FIG. 2B depicts the results of a Cel-1 mismatch assay (Surveyor™, Transgenomic) demonstrating the presence of novel sequences that create a mismatch. The percent of alleles carrying the mutation (% NHEJ) is indicated in the text to the right of the gels (first column corresponding to lane number on the gels). Numbers refer to ZFN combinations; unt: untransfected control.

FIG. 4E depicts the same type of Cel 1 analysis carried out with samples harvested 3 days after transfection of the HSCs or after 17 days of erythroid differentiation. The percent of alleles carrying the mutation (% NHEJ) is indicated at the bottom on the lanes, and the identity of the ZFN pairs used is indicated in each Figure.

In FIG. 5B, the relative level of gamma globin as normalized by the 18s RNA is depicted above the bars, and demonstrates that the level of gamma globin mRNA with respect to 18S is higher in cells that have been treated with the BCL11A-specific ZFNs.

FIG. 6 depicts the amount of gamma globin mRNA in methylcellulose colonies derived from HSC depending on the genotype of the cells. Cells in which both BCL11A genes are wild type ("BB") produce the lowest amount of gamma globin mRNA in comparison with cells that have had a single BCL11A knockout allele ("Bb") or have had both alleles knocked out ("knockout"). Numbers above the bars indicate the percent of gamma globin produced out of total beta-globin.

FIG. 7 shows a series of DNA sequences (SEQ ID NO:140 to 148) of the region upstream of the gamma globin gene following treatment with gamma globin specific ZFNs in K562 cells. The sequences have a number of insertions and deletions including a 13 bp deletion ("Δ13 bp") that is identical to one of the human genotypes associated with HPFH. The 'Reference' sequence (SEQ ID NO: 140) at the top is the sequence of the wild type 5' regulatory region for gamma globin. The binding sites of the ZFN pair are highlighted in red, the naturally occurring 13 bp deletion is underlined.

FIG. 8A shows the relative gamma/beta-globin mRNA ratios; FIG. 8B shows the gamma-globin mRNA levels corrected by 18s RNA levels and FIG. 8C shows the corresponding analysis of beta-globin levels corrected by 18s. Comparison of the averages of the ratios for wild type and mutated colonies indicates that the gamma-globin levels in the colonies with ZFN-induced mutations in the gamma-globin promoter are elevated.

FIG. 9 shows the promoter region of the gamma globin gene (SEQ ID NO:149-152). Two gamma globin alleles are aligned (HBG1 and HBG2). Differences in the sequences of the two alleles are indicated with grey boxes. In addition, the mutations that are associated with HPFH are indicated with black outlines. The starting ATG is indicated as are the exon 1 boundaries. The increase in fetal globin levels associated with each mutation is indicated by a number above it.

DETAILED DESCRIPTION

Figure 2:
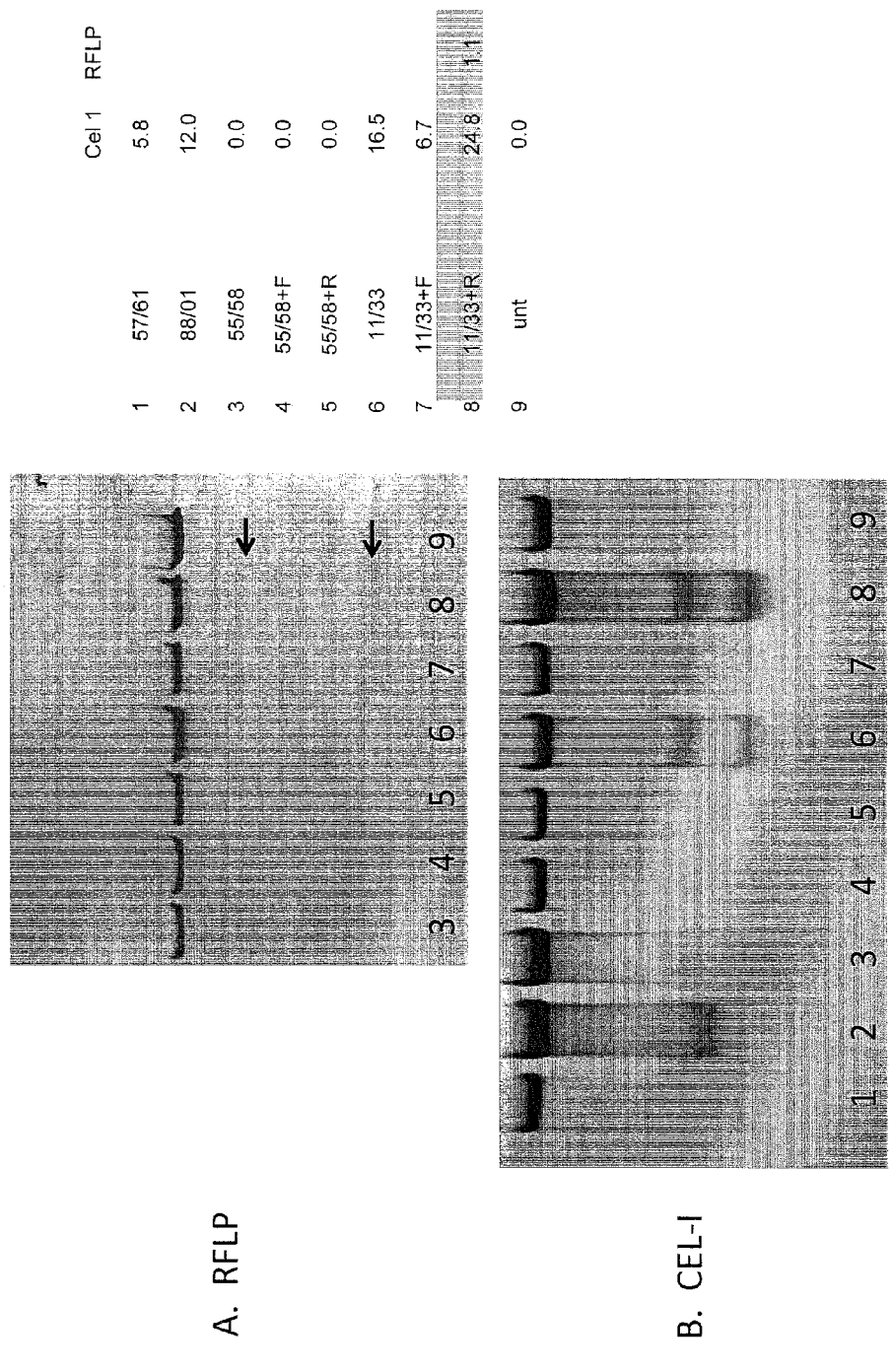
FIG. 2, panels A and B, are gels depicting insertion of a sequence specified by a β globin donor in CD34+ cells.

Disclosed herein are methods and compositions for studying and treating a genetic disease such as a hemoglobinopathy. The invention describes genomic editing of a target cell such that there is a favorable change in the expression of one or more globin genes, which in turn results in treatment of hemoglobinopathies such as sickle cell disease or a thalassemia in a subject in need thereof. Favorable changes in the expression of a globin gene includes, but are not limited to provision of a γ globin gene in a subject with aberrant β globin; and/or correction of an aberrant α or β globin gene sequence. Additionally, delivery of altered hematopoietic stem cells in a transplant altered to express a desired protein product can be similarly beneficial in treating hemoglobinopathies such as sickle cell anemia or a thalassemia. Also described are cell lines and animals with altered globin expression.

Thus, the methods and compositions of the invention can be used to alter the expression of one or more globin genes (e.g., γ, α and/or β) in a cell (e.g., an erythroid precursor cell). These methods and compositions can be used to disrupt genes involved in γ globin repression (e.g., BCL11A or KLF1), such that following editing, the cells will express γ globin at higher levels, and HbF can be produced. Alternatively, editing may be used to disrupt the binding site on a gene (e.g., disrupt BCL11A binding in the beta-globin locus, disrupt binding of repressor of gamma-globin transcription at the gamma-globin promoter) to disable the repression of a gene. Alternatively or in addition to these alterations, the methods and compositions can be used to correct an aberrant endogenous α and/or β globin gene or insert a wild type gene at a desired location in the genome of a cell (e.g., into an HSC). Precursor cells can be derived from subjects in need, modified ex vivo, and then given back to the subject either in a bone marrow graft.

General

Practice of the methods, as well as preparation and use of the compositions disclosed herein employ, unless otherwise indicated, conventional techniques in molecular biology, biochemistry, chromatin structure and analysis, computational chemistry, cell culture, recombinant DNA and related fields as are within the skill of the art. These techniques are fully explained in the literature. See, for example, Sambrook et al. MOLECULAR CLONING: A LABORATORY MANUAL, Second edition, Cold Spring Harbor Laboratory Press, 1989 and Third edition, 2001; Ausubel et al., CURRENT PROTOCOLS IN MOLECULAR BIOLOGY, John Wiley & Sons, New York, 1987 and periodic updates; the series METHODS IN ENZYMOLOGY, Academic Press, San Diego; Wolffe, CHROMATIN STRUCTURE AND FUNCTION, Third edition, Academic Press, San Diego, 1998; METHODS IN ENZYMOLOGY, Vol. 304, "Chromatin" (P. M. Wassarman and A. P. Wolffe, eds.), Academic Press, San Diego, 1999; and METHODS IN MOLECULAR BIOLOGY, Vol. 119, "Chromatin Protocols" (P. B. Becker, ed.) Humana Press, Totowa, 1999.

Definitions

The terms "nucleic acid," "polynucleotide," and "oligonucleotide" are used interchangeably and refer to a deoxyribonucleotide or ribonucleotide polymer, in linear or circular conformation, and in either single- or double-stranded form. For the purposes of the present disclosure, these terms are not to be construed as limiting with respect to the length of a polymer. The terms can encompass known analogues of natural nucleotides, as well as nucleotides that are modified in the base, sugar and/or phosphate moieties (e.g., phosphorothioate backbones). In general, an analogue of a particular nucleotide has the same base-pairing specificity; i.e., an analogue of A will base-pair with T.

The terms "polypeptide," "peptide" and "protein" are used interchangeably to refer to a polymer of amino acid residues. The term also applies to amino acid polymers in which one or more amino acids are chemical analogues or modified derivatives of corresponding naturally-occurring amino acids.

"Binding" refers to a sequence-specific, non-covalent interaction between macromolecules (e.g., between a protein and a nucleic acid). Not all components of a binding interaction need be sequence-specific (e.g., contacts with phosphate residues in a DNA backbone), as long as the interaction as a whole is sequence-specific. Such interactions are generally characterized by a dissociation constant ($K_d$) of $10^{-6}$ $M^{-1}$ or lower. "Affinity" refers to the strength of binding: increased binding affinity being correlated with a lower $K_d$.

A "binding protein" is a protein that is able to bind non-covalently to another molecule. A binding protein can bind to, for example, a DNA molecule (a DNA-binding protein), an RNA molecule (an RNA-binding protein) and/or a protein molecule (a protein-binding protein). In the case of a protein-binding protein, it can bind to itself (to form homodimers, homotrimers, etc.) and/or it can bind to one or more molecules of a different protein or proteins. A binding protein can have more than one type of binding activity. For example, zinc finger proteins have DNA-binding, RNA-binding and protein-binding activity.

A "zinc finger DNA binding protein" (or binding domain) is a protein, or a domain within a larger protein, that binds DNA in a sequence-specific manner through one or more zinc fingers, which are regions of amino acid sequence within the binding domain whose structure is stabilized through coordination of a zinc ion. The term zinc finger DNA binding protein is often abbreviated as zinc finger protein or ZFP.

A "TALE DNA binding domain" or "TALE" is a polypeptide comprising one or more TALE repeat domains/units. The repeat domains are involved in binding of the TALE to its cognate target DNA sequence. A single "repeat unit" (also referred to as a "repeat") is typically 33-35 amino acids in length and exhibits at least some sequence homology with other TALE repeat sequences within a naturally occurring TALE protein. See, e.g., U.S. Patent Publication No. 20110301073.

Zinc finger and TALE binding domains can be "engineered" to bind to a predetermined nucleotide sequence, for example via engineering (altering one or more amino acids) of the recognition helix region of a naturally occurring zinc finger or TALE protein. Therefore, engineered DNA binding proteins (zinc fingers or TALEs) are proteins that are non-naturally occurring. Non-limiting examples of methods for engineering DNA-binding proteins are design and selection. A designed DNA binding protein is a protein not occurring in nature whose design/composition results principally from rational criteria. Rational criteria for design include application of substitution rules and computerized algorithms for processing information in a database storing information of existing ZFP and/or TALE designs and binding data. See, for example, U.S. Pat. Nos. 6,140,081; 6,453,242; and 6,534,261; see also WO 98/53058; WO 98/53059; WO 98/53060; WO 02/016536 and WO 03/016496 and U.S. Publication No. 20110301073.

A "selected" zinc finger protein or TALE is a protein not found in nature whose production results primarily from an empirical process such as phage display, interaction trap or hybrid selection. See e.g., U.S. Pat. No. 5,789,538; U.S. Pat. No. 5,925,523; U.S. Pat. No. 6,007,988; U.S. Pat. No. 6,013,453; U.S. Pat. No. 6,200,759; WO 95/19431; WO 96/06166; WO 98/53057; WO 98/54311; WO 00/27878; WO 01/60970 WO 01/88197; WO 02/099084 and U.S. Publication No. 20110301073.

"Recombination" refers to a process of exchange of genetic information between two polynucleotides. For the purposes of this disclosure, "homologous recombination" (HR) refers to the specialized form of such exchange that takes place, for example, during repair of double-strand breaks in cells via homology-directed repair mechanisms. This process requires nucleotide sequence homology, uses a "donor" molecule to template repair of a "target" molecule (i.e., the one that experienced the double-strand break), and is variously known as "non-crossover gene conversion" or "short tract gene conversion," because it leads to the transfer of genetic information from the donor to the target. Without wishing to be bound by any particular theory, such transfer can involve mismatch correction of heteroduplex DNA that forms between the broken target and the donor, and/or "synthesis-dependent strand annealing," in which the donor is used to re-synthesize genetic information that will become part of the target, and/or related processes. Such specialized HR often results in an alteration of the sequence of the target molecule such that part or all of the sequence of the donor polynucleotide is incorporated into the target polynucleotide.

In the methods of the disclosure, one or more targeted nucleases as described herein create a double-stranded break in the target sequence (e.g., cellular chromatin) at a predetermined site, and a "donor" polynucleotide, having homology to the nucleotide sequence in the region of the break, can be introduced into the cell. The presence of the double-stranded break has been shown to facilitate integration of the donor sequence. The donor sequence may be physically integrated or, alternatively, the donor polynucleotide is used as a template for repair of the break via homologous recombination, resulting in the introduction of all or part of the nucleotide sequence as in the donor into the cellular chromatin. Thus, a first sequence in cellular chromatin can be altered and, in certain embodiments, can be converted into a sequence present in a donor polynucleotide. Thus, the use of the terms "replace" or "replacement" can be understood to represent replacement of one nucleotide sequence by another, (i.e., replacement of a sequence in the informational sense), and does not necessarily require physical or chemical replacement of one polynucleotide by another.

In any of the methods described herein, additional pairs of zinc-finger or TALEN proteins can be used for additional double-stranded cleavage of additional target sites within the cell. In addition, a CRISPR/Cas system may be similarly employed to induce additional double strand breaks.

In certain embodiments of methods for targeted recombination and/or replacement and/or alteration of a sequence in a region of interest in cellular chromatin, a chromosomal sequence is altered by homologous recombination with an exogenous "donor" nucleotide sequence. Such homologous recombination is stimulated by the presence of a double-stranded break in cellular chromatin, if sequences homologous to the region of the break are present.

In any of the methods described herein, the exogenous nucleotide sequence (the "donor sequence" or "transgene") can contain sequences that are homologous, but not identical, to genomic sequences in the region of interest, thereby stimulating homologous recombination to insert a non-identical sequence in the region of interest. Thus, in certain embodiments, portions of the donor sequence that are homologous to sequences in the region of interest exhibit between about 80 to 99% (or any integer therebetween) sequence identity to the genomic sequence that is replaced. In other embodiments, the homology between the donor and genomic sequence is higher than 99%, for example if only 1 nucleotide differs as between donor and genomic sequences of over 100 contiguous base pairs. In certain cases, a non-homologous portion of the donor sequence can contain sequences not present in the region of interest, so that new sequences are introduced into the region of interest. In these instances, the non-homologous sequence is generally flanked by sequences of 50-1,000 base pairs (or any integral value therebetween) or any number of base pairs greater than 1,000, that are homologous or identical to sequences in the region of interest. In other embodiments, the donor sequence is non-homologous to the first sequence, and is inserted into the genome by non-homologous recombination mechanisms.

Any of the methods described herein can be used for partial or complete inactivation of one or more target sequences in a cell by targeted integration of donor sequence that disrupts expression of the gene(s) of interest. Cell lines with partially or completely inactivated genes are also provided.

Furthermore, the methods of targeted integration as described herein can also be used to integrate one or more exogenous sequences. The exogenous nucleic acid sequence can comprise, for example, one or more genes or cDNA molecules, or any type of coding or non-coding sequence, as well as one or more control elements (e.g., promoters). In addition, the exogenous nucleic acid sequence may produce one or more RNA molecules (e.g., small hairpin RNAs (shRNAs), inhibitory RNAs (RNAis), microRNAs (miRNAs), etc.).

"Cleavage" refers to the breakage of the covalent backbone of a DNA molecule. Cleavage can be initiated by a variety of methods including, but not limited to, enzymatic or chemical hydrolysis of a phosphodiester bond. Both single-stranded cleavage and double-stranded cleavage are possible, and double-stranded cleavage can occur as a result of two distinct single-stranded cleavage events. DNA cleavage can result in the production of either blunt ends or staggered ends. In certain embodiments, fusion polypeptides are used for targeted double-stranded DNA cleavage.

A "cleavage half-domain" is a polypeptide sequence which, in conjunction with a second polypeptide (either identical or different) forms a complex having cleavage activity (preferably double-strand cleavage activity). The terms "first and second cleavage half-domains;" "+ and − cleavage half-domains" and "right and left cleavage half-domains" are used interchangeably to refer to pairs of cleavage half-domains that dimerize.

An "engineered cleavage half-domain" is a cleavage half-domain that has been modified so as to form obligate heterodimers with another cleavage half-domain (e g., another engineered cleavage half-domain) See, also, U.S. Patent Publication Nos. 2005/0064474, 2007/0218528; 2008/0131962 and 2011/0201055, incorporated herein by reference in their entireties.

The term "sequence" refers to a nucleotide sequence of any length, which can be DNA or RNA; can be linear, circular or branched and can be either single-stranded or double stranded. The term "donor sequence" refers to a nucleotide sequence that is inserted into a genome. A donor sequence can be of any length, for example between 2 and 10,000 nucleotides in length (or any integer value therebetween or thereabove), preferably between about 100 and 1,000 nucleotides in length (or any integer therebetween), more preferably between about 200 and 500 nucleotides in length.

A "disease associated gene" is one that is defective in some manner in a monogenic disease. Non-limiting examples of monogenic diseases include severe combined immunodeficiency, cystic fibrosis, lysosomal storage diseases (e.g. Gaucher's, Hurler's, Hunter's, Fabry's, Neimann-Pick, Tay-Sach's, etc.), sickle cell anemia, and thalassemia.

"Chromatin" is the nucleoprotein structure comprising the cellular genome. Cellular chromatin comprises nucleic acid, primarily DNA, and protein, including histones and non-histone chromosomal proteins. The majority of eukaryotic cellular chromatin exists in the form of nucleosomes, wherein a nucleosome core comprises approximately 150 base pairs of DNA associated with an octamer comprising two each of histones H2A, H2B, H3 and H4; and linker DNA (of variable length depending on the organism) extends between nucleosome cores. A molecule of histone H1 is generally associated with the linker DNA. For the purposes of the present disclosure, the term "chromatin" is meant to encompass all types of cellular nucleoprotein, both prokaryotic and eukaryotic. Cellular chromatin includes both chromosomal and episomal chromatin.

A "chromosome," is a chromatin complex comprising all or a portion of the genome of a cell. The genome of a cell is often characterized by its karyotype, which is the collection of all the chromosomes that comprise the genome of the cell. The genome of a cell can comprise one or more chromosomes.

An "episome" is a replicating nucleic acid, nucleoprotein complex or other structure comprising a nucleic acid that is not part of the chromosomal karyotype of a cell. Examples of episomes include plasmids and certain viral genomes.

A "target site" or "target sequence" is a nucleic acid sequence that defines a portion of a nucleic acid to which a binding molecule will bind, provided sufficient conditions for binding exist.

An "exogenous" molecule is a molecule that is not normally present in a cell, but can be introduced into a cell by one or more genetic, biochemical or other methods. "Normal presence in the cell" is determined with respect to the particular developmental stage and environmental conditions of the cell. Thus, for example, a molecule that is present only during embryonic development of muscle is an exogenous molecule with respect to an adult muscle cell. Similarly, a molecule induced by heat shock is an exogenous molecule with respect to a non-heat-shocked cell. An exogenous molecule can comprise, for example, a functioning version of a malfunctioning endogenous molecule or a malfunctioning version of a normally-functioning endogenous molecule.

An exogenous molecule can be, among other things, a small molecule, such as is generated by a combinatorial chemistry process, or a macromolecule such as a protein, nucleic acid, carbohydrate, lipid, glycoprotein, lipoprotein, polysaccharide, any modified derivative of the above molecules, or any complex comprising one or more of the above molecules. Nucleic acids include DNA and RNA, can be single- or double-stranded; can be linear, branched or circular; and can be of any length. Nucleic acids include those capable of forming duplexes, as well as triplex-forming nucleic acids. See, for example, U.S. Pat. Nos. 5,176,996 and 5,422,251. Proteins include, but are not limited to, DNA-binding proteins, transcription factors, chromatin remodeling factors, methylated DNA binding proteins, polymerases, methylases, demethylases, acetylases, deacetylases, kinases, phosphatases, integrases, recombinases, ligases, topoisomerases, gyrases and helicases.

An exogenous molecule can be the same type of molecule as an endogenous molecule, e.g., an exogenous protein or nucleic acid. For example, an exogenous nucleic acid can comprise an infecting viral genome, a plasmid or episome introduced into a cell, or a chromosome that is not normally present in the cell. Methods for the introduction of exogenous molecules into cells are known to those of skill in the art and include, but are not limited to, lipid-mediated transfer (i.e., liposomes, including neutral and cationic lipids), electroporation, direct injection, cell fusion, particle bombardment, calcium phosphate co-precipitation, DEAE-dextran-mediated transfer and viral vector-mediated transfer. An exogenous molecule can also be the same type of molecule as an endogenous molecule but derived from a different species than the cell is derived from. For example, a human nucleic acid sequence may be introduced into a cell line originally derived from a mouse or hamster.

By contrast, an "endogenous" molecule is one that is normally present in a particular cell at a particular developmental stage under particular environmental conditions. For example, an endogenous nucleic acid can comprise a chromosome, the genome of a mitochondrion, chloroplast or other organelle, or a naturally-occurring episomal nucleic acid. Additional endogenous molecules can include proteins, for example, transcription factors and enzymes.

A "fusion" molecule is a molecule in which two or more subunit molecules are linked, preferably covalently. The subunit molecules can be the same chemical type of molecule, or can be different chemical types of molecules. Examples of the first type of fusion molecule include, but are not limited to, fusion proteins (for example, a fusion between a ZFP or TALE DNA-binding domain and one or more activation domains) and fusion nucleic acids (for example, a nucleic acid encoding the fusion protein described supra). Examples of the second type of fusion molecule include, but are not limited to, a fusion between a triplex-forming nucleic acid and a polypeptide, and a fusion between a minor groove binder and a nucleic acid.

Expression of a fusion protein in a cell can result from delivery of the fusion protein to the cell or by delivery of a polynucleotide encoding the fusion protein to a cell, wherein the polynucleotide is transcribed, and the transcript is translated, to generate the fusion protein. Trans-splicing, polypeptide cleavage and polypeptide ligation can also be involved in expression of a protein in a cell. Methods for polynucleotide and polypeptide delivery to cells are presented elsewhere in this disclosure.

A "gene," for the purposes of the present disclosure, includes a DNA region encoding a gene product (see infra), as well as all DNA regions which regulate the production of the gene product, whether or not such regulatory sequences are adjacent to coding and/or transcribed sequences. Accordingly, a gene includes, but is not necessarily limited to, promoter sequences, terminators, translational regulatory sequences such as ribosome binding sites and internal ribosome entry sites, enhancers, silencers, insulators, boundary elements, replication origins, matrix attachment sites and locus control regions.

"Gene expression" refers to the conversion of the information, contained in a gene, into a gene product. A gene product can be the direct transcriptional product of a gene (e.g., mRNA, tRNA, rRNA, antisense RNA, ribozyme, structural RNA or any other type of RNA) or a protein produced by translation of an mRNA. Gene products also include RNAs which are modified, by processes such as capping, polyadenylation, methylation, and editing, and proteins modified by, for example, methylation, acetylation, phosphorylation, ubiquitination, ADP-ribosylation, myristilation, and glycosylation.

"Modulation" of gene expression refers to a change in the activity of a gene. Modulation of expression can include, but is not limited to, gene activation and gene repression. Genome editing (e.g., cleavage, alteration, inactivation, random mutation) can be used to modulate expression. Gene inactivation refers to any reduction in gene expression as compared to a cell that does not include a ZFP or TALEN as described herein. Thus, gene inactivation may be partial or complete.

A "region of interest" is any region of cellular chromatin, such as, for example, a gene or a non-coding sequence within or adjacent to a gene, in which it is desirable to bind an exogenous molecule. Binding can be for the purposes of targeted DNA cleavage and/or targeted recombination. A region of interest can be present in a chromosome, an episome, an organellar genome (e.g., mitochondrial, chloroplast), or an infecting viral genome, for example. A region of interest can be within the coding region of a gene, within transcribed non-coding regions such as, for example, leader sequences, trailer sequences or introns, or within non-transcribed regions, either upstream or downstream of the coding region. A region of interest can be as small as a single nucleotide pair or up to 2,000 nucleotide pairs in length, or any integral value of nucleotide pairs.

"Eukaryotic" cells include, but are not limited to, fungal cells (such as yeast), plant cells, animal cells, mammalian cells and human cells (e.g., T-cells).

"Red Blood Cells" (RBCs), or erythrocytes, are terminally differentiated cells derived from hematopoietic stem cells. They lack a nuclease and most cellular organelles. RBCs contain hemoglobin to carry oxygen from the lungs to the peripheral tissues. In fact, 33% of an individual RBC is hemoglobin. They also carry CO2 produced by cells during metabolism out of the tissues and back to the lungs for release during exhale. RBCs are produced in the bone marrow in response to blood hypoxia which is mediated by release of erythropoietin (EPO) by the kidney. EPO causes an increase in the number of proerythroblasts and shortens the time required for full RBC maturation. After approximately 120 days, since the RBC do not contain a nucleus or any other regenerative capabilities, the cells are removed from circulation by either the phagocytic activities of macrophages in the liver, spleen and lymph nodes (~90%) or by hemolysis in the plasma (~10%). Following macrophage engulfment, chemical components of the RBC are broken down within vacuoles of the macrophages due to the action of lysosomal enzymes.

"Secretory tissues" are those tissues in an animal that secrete products out of the individual cell into a lumen of some type which are typically derived from epithelium. Examples of secretory tissues that are localized to the gastrointestinal tract include the cells that line the gut, the pancreas, and the gallbladder. Other secretory tissues include the liver, tissues associated with the eye and mucous membranes such as salivary glands, mammary glands, the prostate gland, the pituitary gland and other members of the endocrine system. Additionally, secretory tissues include individual cells of a tissue type which are capable of secretion.

The terms "operative linkage" and "operatively linked" (or "operably linked") are used interchangeably with reference to a juxtaposition of two or more components (such as sequence elements), in which the components are arranged such that both components function normally and allow the possibility that at least one of the components can mediate a function that is exerted upon at least one of the other components. By way of illustration, a transcriptional regulatory sequence, such as a promoter, is operatively linked to a coding sequence if the transcriptional regulatory sequence controls the level of transcription of the coding sequence in response to the presence or absence of one or more transcriptional regulatory factors. A transcriptional regulatory sequence is generally operatively linked in cis with a coding sequence, but need not be directly adjacent to it. For example, an enhancer is a transcriptional regulatory sequence that is operatively linked to a coding sequence, even though they are not contiguous.

With respect to fusion polypeptides, the term "operatively linked" can refer to the fact that each of the components performs the same function in linkage to the other component as it would if it were not so linked. For example, with respect to a fusion polypeptide in which a ZFP, TALE or Cas DNA-binding domain is fused to an activation domain, the ZFP, TALE or Cas DNA-binding domain and the activation domain are in operative linkage if, in the fusion polypeptide, the ZFP, TALE or Cas DNA-binding domain portion is able to bind its target site and/or its binding site, while the activation domain is able to up-regulate gene expression. When a fusion polypeptide in which a ZFP or TALE DNA-binding domain is fused to a cleavage domain, the ZFP or TALE DNA-binding domain and the cleavage domain are in operative linkage if, in the fusion polypeptide, the ZFP or TALE DNA-binding domain portion is able to bind its target site and/or its binding site, while the cleavage domain is able to cleave DNA in the vicinity of the target site.

A "functional fragment" of a protein, polypeptide or nucleic acid is a protein, polypeptide or nucleic acid whose sequence is not identical to the full-length protein, polypeptide or nucleic acid, yet retains the same function as the full-length protein, polypeptide or nucleic acid. A functional fragment can possess more, fewer, or the same number of residues as the corresponding native molecule, and/or can contain one or more amino acid or nucleotide substitutions. Methods for determining the function of a nucleic acid (e.g., coding function, ability to hybridize to another nucleic acid) are well-known in the art. Similarly, methods for determining protein function are well-known. For example, the DNA-binding function of a polypeptide can be determined, for example, by filter-binding, electrophoretic mobility-shift, or immunoprecipitation assays. DNA cleavage can be assayed by gel electrophoresis. See Ausubel et al., supra. The ability of a protein to interact with another protein can be determined, for example, by co-immunoprecipitation, two-hybrid assays or complementation, both genetic and biochemical. See, for example, Fields et al. (1989) *Nature* 340:245-246; U.S. Pat. No. 5,585,245 and PCT WO 98/44350.

A "vector" is capable of transferring gene sequences to target cells. Typically, "vector construct," "expression vector," and "gene transfer vector," mean any nucleic acid construct capable of directing the expression of a gene of interest and which can transfer gene sequences to target cells. Thus, the term includes cloning, and expression vehicles, as well as integrating vectors.

A "reporter gene" or "reporter sequence" refers to any sequence that produces a protein product that is easily measured, preferably although not necessarily in a routine assay. Suitable reporter genes include, but are not limited to, sequences encoding proteins that mediate antibiotic resistance (e.g., ampicillin resistance, neomycin resistance, G418 resistance, puromycin resistance), sequences encoding colored or fluorescent or luminescent proteins (e.g., green fluorescent protein, enhanced green fluorescent protein, red fluorescent protein, luciferase), and proteins which mediate enhanced cell growth and/or gene amplification (e.g., dihydrofolate reductase). Epitope tags include, for example, one or more copies of FLAG, His, myc, Tap, HA or any detectable amino acid sequence. "Expression tags" include sequences that encode reporters that may be operably linked to a desired gene sequence in order to monitor expression of the gene of interest.

The terms "subject" and "patient" are used interchangeably and refer to mammals such as human patients and non-human primates, as well as experimental animals such as rabbits, dogs, cats, rats, mice, and other animals. Accordingly, the term "subject" or "patient" as used herein means any mammalian patient or subject to which the altered RBCs (or stem cells) of the invention can be administered. Subjects of the present invention include those that have been exposed to one or more chemical toxins, including, for example, a nerve toxin.

Nucleases

Described herein are compositions, particularly nucleases, which are useful targeting a gene for use with hemoglobinopathies. In certain embodiments, the nuclease is naturally occurring. In other embodiments, the nuclease is non-naturally occurring, i.e., engineered in the DNA-binding domain and/or cleavage domain. For example, the DNA-binding domain of a naturally-occurring nuclease may be altered to bind to a selected target site (e.g., a meganuclease that has been engineered to bind to site different than the cognate binding site). In other embodiments, the nuclease comprises heterologous DNA-binding and cleavage domains (e.g., zinc finger nucleases; TAL-effector nucleases; meganuclease DNA-binding domains with heterologous cleavage domains), or a generic nuclease guided by a specific guide RNA (e.g. a CRIPSR/Cas).

A. DNA-Binding Domains

In certain embodiments, the nuclease is a meganuclease (homing endonuclease). Naturally-occurring meganucleases recognize 15-40 base-pair cleavage sites and are commonly grouped into four families: the LAGLIDADG (SEQ ID NO: 252) family, the GIY-YIG family, the His-Cyst box family and the HNH family. Exemplary homing endonucleases include I-SceI, I-CeuI, PI-PspI, PI-Sce, I-SceIV, I-CsmI, I-PanI, I-SceII, I-PpoI, I-SceIII, I-CreI, I-TevI, I-TevII and I-TevIII. Their recognition sequences are known. See also U.S. Pat. No. 5,420,032; U.S. Pat. No. 6,833,252; Belfort et al. (1997) *Nucleic Acids Res.* 25:3379-3388; Dujon et al. (1989) *Gene* 82:115-118; Perler et al. (1994) *Nucleic Acids Res.* 22, 1125-1127; Jasin (1996) *Trends Genet.* 12:224-228; Gimble et al. (1996) *J. Mol. Biol.* 263:163-180; Argast et al. (1998) *J. Mol. Biol.* 280:345-353 and the New England Biolabs catalogue.

In certain embodiments, the nuclease comprises an engineered (non-naturally occurring) homing endonuclease (meganuclease). The recognition sequences of homing endonucleases and meganucleases such as I-SceI, I-CeuI, PI-PspI, PI-Sce, I-SceIV, I-CsmI, I-PanI, I-SceII, I-PpoI, I-SceIII, I-CreI, I-TevI, I-TevII and I-TevIII are known. See also U.S. Pat. No. 5,420,032; U.S. Pat. No. 6,833,252; Belfort et al. (1997) *Nucleic Acids Res.* 25:3379-3388; Dujon et al. (1989) *Gene* 82:115-118; Perler et al. (1994) *Nucleic Acids Res.* 22, 1125-1127; Jasin (1996) *Trends Genet.* 12:224-228; Gimble et al. (1996) *J. Mol. Biol.* 263:163-180; Argast et al. (1998) *J. Mol. Biol.* 280:345-353 and the New England Biolabs catalogue. In addition, the DNA-binding specificity of homing endonucleases and meganucleases can be engineered to bind non-natural target sites. See, for example, Chevalier et al. (2002) *Molec. Cell* 10:895-905; Epinat et al. (2003) *Nucleic Acids Res.* 31:2952-2962; Ashworth et al. (2006) *Nature* 441:656-659; Paques et al. (2007) *Current Gene Therapy* 7:49-66; U.S. Patent Publication No. 20070117128. The DNA-binding domains of the homing endonucleases and meganucleases may be altered in the context of the nuclease as a whole (i.e., such that the nuclease includes the cognate cleavage domain) or may be fused to a heterologous cleavage domain.

In other embodiments, the DNA-binding domain comprises a naturally occurring or engineered (non-naturally occurring) TAL effector DNA binding domain. See, e.g., U.S. Patent Publication No. 20110301073, incorporated by reference in its entirety herein. The plant pathogenic bacteria of the genus *Xanthomonas* are known to cause many diseases in important crop plants. Pathogenicity of *Xanthomonas* depends on a conserved type III secretion (T3S) system which injects more than 25 different effector proteins into the plant cell. Among these injected proteins are transcription activator-like effectors (TALE) which mimic plant transcriptional activators and manipulate the plant transcriptome (see Kay et al (2007) *Science* 318:648-651). These proteins contain a DNA binding domain and a transcriptional activation domain. One of the most well characterized TALEs is AvrBs3 from *Xanthomonas campestgris* pv. *Vesi-*

*catoria* (see Bonas et al (1989) *Mol Gen Genet* 218: 127-136 and WO2010079430). TALEs contain a centralized domain of tandem repeats, each repeat containing approximately 34 amino acids, which are key to the DNA binding specificity of these proteins. In addition, they contain a nuclear localization sequence and an acidic transcriptional activation domain (for a review see Schornack S, et al (2006) *J Plant Physiol* 163(3): 256-272). In addition, in the phytopathogenic bacteria *Ralstonia solanacearum* two genes, designated brg11 and hpx17 have been found that are homologous to the AvrBs3 family of *Xanthomonas* in the *R. solanacearum* biovar 1 strain GMI1000 and in the biovar 4 strain RS1000 (See Heuer et al (2007) *Appl and Envir Micro* 73(13): 4379-4384). These genes are 98.9% identical in nucleotide sequence to each other but differ by a deletion of 1,575 bp in the repeat domain of hpx17. However, both gene products have less than 40% sequence identity with AvrBs3 family proteins of *Xanthomonas*.

Thus, in some embodiments, the DNA binding domain that binds to a target site in a target locus (e.g., globin or safe harbor) is an engineered domain from a TAL effector similar to those derived from the plant pathogens *Xanthomonas* (see Boch et al, (2009) *Science* 326: 1509-1512 and Moscou and Bogdanove, (2009) *Science* 326: 1501) and Ralstonia (see Heuer et at (2007) *Applied and Environmental Microbiology* 73(13): 4379-4384); U.S. Pat. Nos. 8,420,782 and 8,440,431 and U.S. Patent Publication No. 20110301073.

In certain embodiments, the DNA binding domain comprises a zinc finger protein (e.g., a zinc finger protein that binds to a target site in a globin or safe-harbor gene). Preferably, the zinc finger protein is non-naturally occurring in that it is engineered to bind to a target site of choice. See, for example, See, for example, Beerli et al. (2002) *Nature Biotechnol.* 20:135-141; Pabo et al. (2001) *Ann. Rev. Biochem.* 70:313-340; Isalan et al. (2001) *Nature Biotechnol.* 19:656-660; Segal et al. (2001) *Curr. Opin. Biotechnol.* 12:632-637; Choo et al. (2000) *Curr. Opin. Struct. Biol.* 10:411-416; U.S. Pat. Nos. 6,453,242; 6,534,261; 6,599, 692; 6,503,717; 6,689,558; 7,030,215; 6,794,136; 7,067, 317; 7,262,054; 7,070,934; 7,361,635; 7,253,273; and U.S. Patent Publication Nos. 2005/0064474; 2007/0218528; 2005/0267061, all incorporated herein by reference in their entireties.

An engineered zinc finger binding or TALE domain can have a novel binding specificity, compared to a naturally-occurring zinc finger protein. Engineering methods include, but are not limited to, rational design and various types of selection. Rational design includes, for example, using databases comprising triplet (or quadruplet) nucleotide sequences and individual zinc finger amino acid sequences, in which each triplet or quadruplet nucleotide sequence is associated with one or more amino acid sequences of zinc fingers which bind the particular triplet or quadruplet sequence. See, for example, co-owned U.S. Pat. Nos. 6,453, 242 and 6,534,261, incorporated by reference herein in their entireties.

Exemplary selection methods, including phage display and two-hybrid systems, are disclosed in U.S. Pat. Nos. 5,789,538; 5,925,523; 6,007,988; 6,013,453; 6,410,248; 6,140,466; 6,200,759; and 6,242,568; as well as WO 98/37186; WO 98/53057; WO 00/27878; WO 01/88197 and GB 2,338,237. In addition, enhancement of binding specificity for zinc finger binding domains has been described, for example, in co-owned WO 02/077227.

In addition, as disclosed in these and other references, DNA domains (e.g., multi-fingered zinc finger proteins or TALE domains) may be linked together using any suitable linker sequences, including for example, linkers of 5 or more amino acids in length. See, also, U.S. Pat. Nos. 6,479,626; 6,903,185; and 7,153,949 for exemplary linker sequences 6 or more amino acids in length. The DNA binding proteins described herein may include any combination of suitable linkers between the individual zinc fingers of the protein. In addition, enhancement of binding specificity for zinc finger binding domains has been described, for example, in co-owned WO 02/077227.

Selection of target sites; DNA-binding domains and methods for design and construction of fusion proteins (and polynucleotides encoding same) are known to those of skill in the art and described in detail in U.S. Pat. Nos. 6,140,081; 5,789,538; 6,453,242; 6,534,261; 5,925,523; 6,007,988; 6,013,453; 6,200,759; WO 95/19431; WO 96/06166; WO 98/53057; WO 98/54311; WO 00/27878; WO 01/60970 WO 01/88197; WO 02/099084; WO 98/53058; WO 98/53059; WO 98/53060; WO 02/016536 and WO 03/016496 and U.S. Publication No. 20110301073.

In addition, as disclosed in these and other references, DNA-binding domains (e.g., multi-fingered zinc finger proteins) may be linked together using any suitable linker sequences, including for example, linkers of 5 or more amino acids in length. See, also, U.S. Pat. Nos. 6,479,626; 6,903,185; and 7,153,949 for exemplary linker sequences 6 or more amino acids in length. The proteins described herein may include any combination of suitable linkers between the individual zinc fingers of the protein.

B. Cleavage Domains

Any suitable cleavage domain can be operatively linked to a DNA-binding domain to form a nuclease. For example, ZFP DNA-binding domains have been fused to nuclease domains to create ZFNs—a functional entity that is able to recognize its intended nucleic acid target through its engineered (ZFP) DNA binding domain and cause the DNA to be cut near the ZFP binding site via the nuclease activity. See, e.g., Kim et al. (1996) *Proc Nat'l Acad Sci USA* 93(3):1156-1160. More recently, ZFNs have been used for genome modification in a variety of organisms. See, for example, United States Patent Publications 20030232410; 20050208489; 20050026157; 20050064474; 20060188987; 20060063231; and International Publication WO 07/014, 275. Likewise, TALE DNA-binding domains have been fused to nuclease domains to create TALENs. See, e.g., U.S. Publication No. 20110301073.

As noted above, the cleavage domain may be heterologous to the DNA-binding domain, for example a zinc finger DNA-binding domain and a cleavage domain from a nuclease or a TALEN DNA-binding domain and a cleavage domain, or meganuclease DNA-binding domain and cleavage domain from a different nuclease. Heterologous cleavage domains can be obtained from any endonuclease or exonuclease. Exemplary endonucleases from which a cleavage domain can be derived include, but are not limited to, restriction endonucleases and homing endonucleases. See, for example, 2002-2003 Catalogue, New England Biolabs, Beverly, Mass.; and Belfort et al. (1997) *Nucleic Acids Res.* 25:3379-3388. Additional enzymes which cleave DNA are known (e.g., S1 Nuclease; mung bean nuclease; pancreatic DNase I; micrococcal nuclease; yeast HO endonuclease; see also Linn et al. (eds.) *Nucleases*, Cold Spring Harbor Laboratory Press, 1993). One or more of these enzymes (or functional fragments thereof) can be used as a source of cleavage domains and cleavage half-domains.

Similarly, a cleavage half-domain can be derived from any nuclease or portion thereof, as set forth above, that requires dimerization for cleavage activity. In general, two fusion proteins are required for cleavage if the fusion proteins comprise cleavage half-domains. Alternatively, a single protein comprising two cleavage half-domains can be used. The two cleavage half-domains can be derived from the same endonuclease (or functional fragments thereof), or each cleavage half-domain can be derived from a different endonuclease (or functional fragments thereof). In addition, the target sites for the two fusion proteins are preferably disposed, with respect to each other, such that binding of the two fusion proteins to their respective target sites places the cleavage half-domains in a spatial orientation to each other that allows the cleavage half-domains to form a functional cleavage domain, e.g., by dimerizing. Thus, in certain embodiments, the near edges of the target sites are separated by 5-8 nucleotides or by 15-18 nucleotides. However any integral number of nucleotides or nucleotide pairs can intervene between two target sites (e.g., from 2 to 50 nucleotide pairs or more). In general, the site of cleavage lies between the target sites.

Restriction endonucleases (restriction enzymes) are present in many species and are capable of sequence-specific binding to DNA (at a recognition site), and cleaving DNA at or near the site of binding. Certain restriction enzymes (e.g., Type IIS) cleave DNA at sites removed from the recognition site and have separable binding and cleavage domains. For example, the Type IIS enzyme Fok I catalyzes double-stranded cleavage of DNA, at 9 nucleotides from its recognition site on one strand and 13 nucleotides from its recognition site on the other. See, for example, U.S. Pat. Nos. 5,356,802; 5,436,150 and 5,487,994; as well as Li et al. (1992) *Proc. Natl. Acad. Sci. USA* 89:4275-4279; Li et al. (1993) *Proc. Natl. Acad. Sci. USA* 90:2764-2768; Kim et al. (1994a) *Proc. Natl. Acad. Sci. USA* 91:883-887; Kim et al. (1994b) *J. Biol. Chem.* 269:31,978-31,982. Thus, in one embodiment, fusion proteins comprise the cleavage domain (or cleavage half-domain) from at least one Type IIS restriction enzyme and one or more zinc finger binding domains, which may or may not be engineered.

An exemplary Type IIS restriction enzyme, whose cleavage domain is separable from the binding domain, is Fok I. This particular enzyme is active as a dimer. Bitinaite et al. (1998) *Proc. Natl. Acad. Sci. USA* 95: 10,570-10,575. Accordingly, for the purposes of the present disclosure, the portion of the Fok I enzyme used in the disclosed fusion proteins is considered a cleavage half-domain. Thus, for targeted double-stranded cleavage and/or targeted replacement of cellular sequences using zinc finger-Fok I fusions, two fusion proteins, each comprising a FokI cleavage half-domain, can be used to reconstitute a catalytically active cleavage domain. Alternatively, a single polypeptide molecule containing a DNA binding domain and two Fok I cleavage half-domains can also be used.

A cleavage domain or cleavage half-domain can be any portion of a protein that retains cleavage activity, or that retains the ability to multimerize (e.g., dimerize) to form a functional cleavage domain.

Exemplary Type IIS restriction enzymes are described in International Publication WO 07/014,275, incorporated herein in its entirety. Additional restriction enzymes also contain separable binding and cleavage domains, and these are contemplated by the present disclosure. See, for example, Roberts et al. (2003) *Nucleic Acids Res.* 31:418-420.

In certain embodiments, the cleavage domain comprises one or more engineered cleavage half-domain (also referred to as dimerization domain mutants) that minimize or prevent homodimerization, as described, for example, in U.S. Patent Publication Nos. 20050064474; 20060188987 and 20080131962, the disclosures of all of which are incorporated by reference in their entireties herein. Amino acid residues at positions 446, 447, 479, 483, 484, 486, 487, 490, 491, 496, 498, 499, 500, 531, 534, 537, and 538 of Fok I are all targets for influencing dimerization of the Fok I cleavage half-domains.

Exemplary engineered cleavage half-domains of Fok I that form obligate heterodimers include a pair in which a first cleavage half-domain includes mutations at amino acid residues at positions 490 and 538 of Fok I and a second cleavage half-domain includes mutations at amino acid residues 486 and 499.

Thus, in one embodiment, a mutation at 490 replaces Glu (E) with Lys (K); the mutation at 538 replaces Iso (I) with Lys (K); the mutation at 486 replaced Gln (Q) with Glu (E); and the mutation at position 499 replaces Iso (I) with Lys (K). Specifically, the engineered cleavage half-domains described herein were prepared by mutating positions 490 (E→K) and 538 (I→K) in one cleavage half-domain to produce an engineered cleavage half-domain designated "E490K:I538K" and by mutating positions 486 (Q→E) and 499 (I→L) in another cleavage half-domain to produce an engineered cleavage half-domain designated "Q486E: I499L". The engineered cleavage half-domains described herein are obligate heterodimer mutants in which aberrant cleavage is minimized or abolished. See, e.g., U.S. Patent Publication No. 2008/0131962, the disclosure of which is incorporated by reference in its entirety for all purposes.

In certain embodiments, the engineered cleavage half-domain comprises mutations at positions 486, 499 and 496 (numbered relative to wild-type FokI), for instance mutations that replace the wild type Gln (Q) residue at position 486 with a Glu (E) residue, the wild type Iso (I) residue at position 499 with a Leu (L) residue and the wild-type Asn (N) residue at position 496 with an Asp (D) or Glu (E) residue (also referred to as a "ELD" and "ELE" domains, respectively). In other embodiments, the engineered cleavage half-domain comprises mutations at positions 490, 538 and 537 (numbered relative to wild-type FokI), for instance mutations that replace the wild type Glu (E) residue at position 490 with a Lys (K) residue, the wild type Iso (I) residue at position 538 with a Lys (K) residue, and the wild-type His (H) residue at position 537 with a Lys (K) residue or a Arg (R) residue (also referred to as "KKK" and "KKR" domains, respectively). In other embodiments, the engineered cleavage half-domain comprises mutations at positions 490 and 537 (numbered relative to wild-type FokI), for instance mutations that replace the wild type Glu (E) residue at position 490 with a Lys (K) residue and the wild-type His (H) residue at position 537 with a Lys (K) residue or a Arg (R) residue (also referred to as "KIK" and "KIR" domains, respectively). (See US Patent Publication No. 20110201055, incorporated by reference herein). Engineered cleavage half-domains described herein can be prepared using any suitable method, for example, by site-directed mutagenesis of wild-type cleavage half-domains (Fok I) as described in U.S. Patent Publication Nos. 20050064474; 20080131962; and 20110201055.

Alternatively, nucleases may be assembled in vivo at the nucleic acid target site using so-called "split-enzyme" technology (see, e.g., U.S. Patent Publication No. 20090068164). Components of such split enzymes may be expressed either on separate expression constructs, or can be linked in one open reading frame where the individual components are separated, for example, by a self-cleaving 2A peptide or IRES sequence. Components may be individual zinc finger binding domains or domains of a meganuclease nucleic acid binding domain.

Nucleases can be screened for activity prior to use, for example in a yeast-based chromosomal system as described in WO 2009/042163 and 20090068164. Nuclease expression constructs can be readily designed using methods known in the art. See, e.g., United States Patent Publications 20030232410; 20050208489; 20050026157; 20050064474; 20060188987; 20060063231; and International Publication WO 07/014,275. Expression of the nuclease may be under the control of a constitutive promoter or an inducible promoter, for example the galactokinase promoter which is activated (de-repressed) in the presence of raffinose and/or galactose and repressed in presence of glucose.

The CRISPR/Cas System

Compelling evidence has recently emerged for the existence of an RNA-mediated genome defense pathway in archaea and many bacteria that has been hypothesized to parallel the eukaryotic RNAi pathway (for reviews, see Godde and Bickerton, 2006. *J. Mol. Evol.* 62: 718-729; Lillestol et al., 2006. *Archaea* 2: 59-72; Makarova et al., 2006. *Biol. Direct* 1: 7; Sorek et al., 2008. *Nat. Rev. Microbiol.* 6: 181-186). Known as the CRISPR-Cas system or prokaryotic RNAi (pRNAi), the pathway is proposed to arise from two evolutionarily and often physically linked gene loci: the CRISPR (clustered regularly interspaced short palindromic repeats) locus, which encodes RNA components of the system, and the cas (CRISPR-associated) locus, which encodes proteins (Jansen et al., 2002. *Mol. Microbiol.* 43: 1565-1575; Makarova et al., 2002. *Nucleic Acids Res.* 30: 482-496; Makarova et al., 2006. *Biol. Direct* 1: 7; Haft et al., 2005. *PLoS Comput. Biol.* 1: e60). CRISPR loci in microbial hosts contain a combination of CRISPR-associated (Cas) genes as well as non-coding RNA elements capable of programming the specificity of the CRISPR-mediated nucleic acid cleavage. The individual Cas proteins do not share significant sequence similarity with protein components of the eukaryotic RNAi machinery, but have analogous predicted functions (e.g., RNA binding, nuclease, helicase, etc.) (Makarova et al., 2006. *Biol. Direct* 1: 7). The CRISPR-associated (cas) genes are often associated with CRISPR repeat-spacer arrays. More than forty different Cas protein families have been described. Of these protein families, Cas1 appears to be ubiquitous among different CRISPR/Cas systems. Particular combinations of cas genes and repeat structures have been used to define 8 CRISPR subtypes (*Ecoli*, Ypest, Nmeni, Dvulg, Tneap, Hmari, Apern, and Mtube), some of which are associated with an additional gene module encoding repeat-associated mysterious proteins (RAMPs). More than one CRISPR subtype may occur in a single genome. The sporadic distribution of the CRISPR/Cas subtypes suggests that the system is subject to horizontal gene transfer during microbial evolution.

The Type II CRISPR (exemplified by Cas9) is one of the most well characterized systems and carries out targeted DNA double-strand break in four sequential steps. First, two non-coding RNA, the pre-crRNA array and tracrRNA, are transcribed from the CRISPR locus. Second, tracrRNA hybridizes to the repeat regions of the pre-crRNA and mediates the processing of pre-crRNA into mature crRNAs containing individual spacer sequences. Third, the mature crRNA:tracrRNA complex directs Cas9 to the target DNA via Watson-Crick base-pairing between the spacer on the crRNA and the protospacer on the target DNA next to the protospacer adjacent motif (PAM), an additional requirement for target recognition. Finally, Cas9 mediates cleavage of target DNA to create a double-stranded break within the protospacer. Activity of the CRISPR/Cas system comprises of three steps: (i) insertion of alien DNA sequences into the CRISPR array to prevent future attacks, in a process called 'adaptation,' (ii) expression of the relevant proteins, as well as expression and processing of the array, followed by (iii) RNA-mediated interference with the alien nucleic acid. Thus, in the bacterial cell, several of the so-called 'Cas' proteins are involved with the natural function of the CRISPR/Cas system.

The primary products of the CRISPR loci appear to be short RNAs that contain the invader targeting sequences, and are termed guide RNAs or prokaryotic silencing RNAs (psiRNAs) based on their hypothesized role in the pathway (Makarova et al. (2006) *Biol. Direct* 1:7; Hale et al. (2008) *RNA* 14: 2572-2579). RNA analysis indicates that CRISPR locus transcripts are cleaved within the repeat sequences to release ~60- to 70-nt RNA intermediates that contain individual invader targeting sequences and flanking repeat fragments (Tang et al. (2002) *Proc. Natl. Acad. Sci.* 99: 7536-7541; Tang et al. (2005) *Mol. Microbiol.* 55:469-481; Lillestol et al. (2006) *Archaea* 2:59-72; Brouns et al. (2008) *Science* 321: 960-964; Hale et al. (2008) *RNA* 14:2572-2579). In the archaeon *Pyrococcusfuriosus*, these intermediate RNAs are further processed to abundant, stable ~35- to 45-nt mature psiRNAs (Hale et al. (2008) *RNA* 14: 2572-2579).

Cas Proteins

"Cas1" polypeptide refers to CRISPR associated (Cas) protein1. Cas1 (COG1518 in the Clusters of Orthologous Group of proteins classification system) is the best marker of the CRISPR-associated systems (CASS). Based on phylogenetic comparisons, seven distinct versions of the CRISPR-associated immune system have been identified (CASS1-7).

Cas1 polypeptide used in the methods described herein can be any Cas1 polypeptide present in any prokaryote. In certain embodiments, a Cas1 polypeptide is a Cas1 polypeptide of an archaeal microorganism. In certain embodiments, a Cas1 polypeptide is a Cas1 polypeptide of a Euryarchaeota microorganism. In certain embodiments, a Cas1 polypeptide is a Cas1 polypeptide of a Crenarchaeota microorganism. In certain embodiments, a Cas1 polypeptide is a Cas1 polypeptide of a bacterium. In certain embodiments, a Cas1 polypeptide is a Cas1 polypeptide of a gram negative or gram positive bacteria. In certain embodiments, a Cas1 polypeptide is a Cas1 polypeptide of *Pseudomonas aeruginosa*. In certain embodiments, a Cas1 polypeptide is a Cas1 polypeptide of *Aquifexaeolicus*. In certain embodiments, a Cas1 polypeptide is a Cas1 polypeptide that is a member of one of CASS1-7. In certain embodiments, Cas1 polypeptide is a Cas1 polypeptide that is a member of CASS3. In certain embodiments, a Cas1 polypeptide is a Cas1 polypeptide that is a member of CASS7. In certain embodiments, a Cas1 polypeptide is a Cas1 polypeptide that is a member of CASS3 or CASS7.

In some embodiments, a Cas1 polypeptide is encoded by a nucleotide sequence provided in GenBank at, e.g., GeneID number: 2781520, 1006874, 9001811, 947228, 3169280, 2650014, 1175302, 3993120, 4380485, 906625, 3165126, 905808, 1454460, 1445886, 1485099, 4274010, 888506, 3169526, 997745, 897836, or 1193018 and/or an amino acid sequence exhibiting homology (e.g., greater than 80%, 90 to 99% including 91%, 92%, 93%, 94%, 95%, 96%, 97%, 98% or 99%) to the amino acids encoded by these polynucleotides and which polypeptides function as Cas1 polypeptides.

Cas6 is another Cas polypeptide, and the endoribonuclease activity is referred to herein as Cas6 endoribonuclease activity. Non-limiting examples of suitable Cas6 polypeptides are depicted at Genbank Accession No. AAL81255. A Cas6 polypeptide may be enriched, isolated, or purified from a microbe having a CRISPR locus and the cas (CRISPR-associated) locus, such as, but not limited to, *Pyrococcus furiosus*, or may be produced using recombinant techniques, or chemically or enzymatically synthesized using routine methods. In some aspects, a Cas6 polypeptide may be enriched, isolated, or purified from a microbe that does not have CRISPR loci. A Cas6 polypeptide contains at least one residue that may play a role in catalysis, or conservative substitution thereof. A Cas6 polypeptide may contain other residues which may also play a role in catalysis, or conservative substitution thereof. The residue(s) expected to play a role in catalysis may be located near the G-rich loop that contains the Cas6 signature motif in the 3D structure of the protein. Cas6 polypeptides may include domains present in the TIGRFAM database at accession numbers TIGR01877 and PF01881. The TIGRFAM database includes families of polypeptides for which function is conserved (Haft et al. (2003) *Nucl. Acids Res.* 31:371-373, Bateman and Haft (2002) *Briefings Bioinformatics*, 3:236-245, and Haft et al. (2005) *PLoS Computational Biol.* 1(6):e60).

Other examples of Cas6 polypeptides provided herein include those present in prokaryotic microbes having a CRISPR locus and a cas locus. Cas6 polypeptides can be easily identified in any microbe that includes a CRISPR locus. A coding region encoding a Cas6 polypeptide is typically in a cas locus located in close proximity to a CRISPR locus. Haft et al. (2005) *PLoS Computational Biol.* 1(6):e60) review the Cas protein family, and created rules for the identification of specific subtypes of the CRISPR/Cas system. Haft et al. describe the coding region encoding Cas6 polypeptides as being found in association with at least four separate CRISPR/Cas subtypes (Tneap, Hmari, Apern, and Mtube), and as typically being the cas coding region located most distal to the CRISPR locus. Cas6 polypeptides may be identified using the resources available at the JCVI Comprehensive Microbial Resource. Thus, Cas6 polypeptides that are useful in the methods described herein can be identified by the skilled person using routine methods.

Examples of prokaryotic microbes with known whole genomic sequences containing coding regions expected to encode a Cas6 polypeptide include *Thermotoga maritima* MSB8, *Campylobacter fetus* subsp. *fetus* 82-40, *Fusobacterium nucleatum* ATCC 25586, *Streptococcus thermophilus* LMG 18311, *Thermoanaerobacter tengcongensis* MB4(T), *Moorella thermoacetica* ATCC 39073, *Desulfitobacterium hafniense* Y51, *Clostridium tetani* E88, *Clostridium perfringens* SM101, *Clostridium difficile* QCD-32g58, *Clostridium botulinum* Hall A Sanger, *Clostridium botulinum* F Langeland, *Clostridium botulinum* B1 strain Okra, *Clostridium botulinum* A3 strain Loch Maree, *Clostridium botulinum* A Hall, *Clostridium botulinum* A ATCC 19397, *Carboxydothermus hydrogenoformans* Z-2901, *Staphylococcus epidermidis* RP62A, *Thermus thermophilus* HB8, *Thermus thermophilus* HB27, Nostoc sp. PCC 7120, *Anabaena variabilis* ATCC 29413, *Synechococccus* sp. OS Type B prime, *Synechococccus* sp. OS Type A, *Porphyromonas gingivalis* W83, *Bacteroides fragilis* YCH46, *Bacteroides fragilis* NCTC9343, *Aquifex aeolicus* VF5, *Rubrobacter xylanophilus* DSM 9941, *Mycobacterium tuberculosis* H37Rv (lab strain), *Mycobacterium tuberculosis* CDC1551, *Mycobacterium bovis* subsp. *bovis* AF2122/97, *Frankia alni* ACN14a, *Thermoplasma volcanium* GSS1, *Picrophilus torridus* DSM 9790, *Thermococcus kodakarensis* KOD1, *Pyrococcus horikoshiishinkaj* OT3, *Pyrococcus furiosus* DSM 3638, *Pyrococcus abyssi* GE5, *Methanosarcina barkerifusaro*, *Methanosarcina acetivorans* C2A, *Methanococcoides burtonii* DSM 6242, *Methanococcus jannaschii* DSM2661, *Methanobacterium thermoautotrophicum* delta H, *Haloarcula marismortui* ATCC 43049, *Archaeoglobus fulgidus* DSM4304, *Pyrobaculum aerophilum* 1M2, *Sulfolobus tokodaii* strain 7, *Sulfolobus solfataricus* P2, *Sulfolobus acidocaldarius* DSM 639, *Aeropyrum pernix* K1. Other examples of Cas6 polypeptides are known to the skilled person, see, for instance, members of the COG1583 group of polypeptides (available at the Clusters of Orthologous Groups of proteins (COGs) web page through the National Center for Biotechnology Information internet site, see also Tatusov et al. (1997) *Science* 278:631-637 and Tatusov et al. (2003) BMC *Bioinformatics* 4(1):41), members of the InterPro family having accession number IPRO10156, Makarova et al. (2002) *Nuc. Acids Res.* 30:482-496 and Haft et al. (2005) *PLoS Comput. Biol.* 1(6):e60, 474-483).

There are three types of CRISPR/Cas systems which all incorporate RNAs and Cas proteins. Types I and III both have Cas endonucleases that process the pre-crRNAs, that, when fully processed into crRNAs, assemble a multi-Cas protein complex that is capable of cleaving nucleic acids that are complementary to the crRNA.

In type II CRISPR/Cas systems, crRNAs are produced using a different mechanism where a trans-activating RNA (tracrRNA) complementary to repeat sequences in the pre-crRNA, triggers processing by a double strand-specific RNase III in the presence of the Cas9 protein. Cas9 is then able to cleave a target DNA that is complementary to the mature crRNA however cleavage by Cas 9 is dependent both upon base-pairing between the crRNA and the target DNA, and on the presence of a short motif in the crRNA referred to as the PAM sequence (protospacer adjacent motif) (see Qi et al. (2013) *Cell* 152:1173). In addition, the tracrRNA must also be present as it base pairs with the crRNA at its 3' end, and this association triggers Cas9 activity.

The Cas9 protein has at least two nuclease domains: one nuclease domain is similar to a HNH endonuclease, while the other resembles a Ruv endonuclease domain. The HNH-type domain appears to be responsible for cleaving the DNA strand that is complementary to the crRNA while the Ruv domain cleaves the non-complementary strand.

The requirement of the crRNA-tracrRNA complex can be avoided by use of an engineered "single-guide RNA" (sgRNA) that comprises the hairpin normally formed by the annealing of the crRNA and the tracrRNA (see, Jinek et al. (2012) *Science* 337:816 and Cong et al. (2013) *Sciencexpress*/10.1126/science.1231143). In *S. pyrogenes*, the engineered tracrRNA:crRNA fusion, or the sgRNA, guides Cas9 to cleave the target DNA when a double strand RNA:DNA heterodimer forms between the Cas associated RNAs and the target DNA. This system comprising the Cas9 protein and an engineered sgRNA containing a PAM sequence has been used for RNA guided genome editing (see Ramalingam, ibid) and has been useful for zebrafish embryo genomic editing in vivo (see Hwang et al. (2013) *Nature Biotechnology* 31(3):227) with editing efficiencies similar to ZFNs and TALENs.

In certain embodiments, Cas protein may be a "functional derivative" of a naturally occurring Cas protein. A "functional derivative" of a native sequence polypeptide is a compound having a qualitative biological property in common with a native sequence polypeptide. "Functional derivatives" include, but are not limited to, fragments of a native sequence and derivatives of a native sequence polypeptide and its fragments, provided that they have a biological activity in common with a corresponding native sequence polypeptide. A biological activity contemplated herein is the ability of the functional derivative to hydrolyze a DNA substrate into fragments. The term "derivative" encompasses both amino acid sequence variants of polypeptide, covalent modifications, and fusions thereof.

"Cas polypeptide" encompasses a full-length Cas polypeptide, an enzymatically active fragment of a Cas polypeptide, and enzymatically active derivatives of a Cas polypeptide or fragment thereof. Suitable derivatives of a Cas polypeptide or a fragment thereof include but are not limited to mutants, fusions, covalent modifications of Cas protein or a fragment thereof.

Cas proteins and Cas polypeptides may be obtainable from a cell or synthesized chemically or by a combination of these two procedures. The cell may be a cell that naturally produces Cas protein, or a cell that naturally produces Cas protein and is genetically engineered to produce the endogenous Cas protein at a higher expression level or to produce a Cas protein from an exogenously introduced nucleic acid, which nucleic acid encodes a Cas that is same or different from the endogenous Cas. In some case, the cell does not naturally produce Cas protein and is genetically engineered to produce a Cas protein.

The CRISPR/Cas system can also be used to inhibit gene expression. Lei et al. (2013) *Cell* 152(5):1173-1183) have shown that a catalytically dead Cas9 lacking endonuclease activity, when coexpressed with a guide RNA, generates a DNA recognition complex that can specifically interfere with transcriptional elongation, RNA polymerase binding, or transcription factor binding. This system, called CRISPR interference (CRISPRi), can efficiently repress expression of targeted genes.

Additionally, Cas proteins have been developed which comprise mutations in their cleavage domains to render them incapable of inducing a DSB, and instead introduce a nick into the target DNA ("Cas9 nicking enzyme", see Cong et al., ibid).

The Cas proteins of the invention may be mutated to alter functionality. Exemplary selection methods, including phage display and two-hybrid systems, are disclosed in U.S. Pat. Nos. 5,789,538; 5,925,523; 6,007,988; 6,013,453; 6,410,248; 6,140,466; 6,200,759; and 6,242,568; as well as WO 98/37186; WO 98/53057; WO 00/27878; WO 01/88197 and GB 2,338,237.

RNA Components of CRISPR/Cas

The Cas9 related CRISPR/Cas system comprises two RNA non-coding components: tracrRNA and a pre-crRNA array containing nuclease guide sequences (spacers) interspaced by identical direct repeats (DRs). To use a CRISPR/Cas system to accomplish genome engineering, both functions of these RNAs must be present (see Cong et al, (2013) *Sciencexpress* 1/10.1126/science 1231143). In some embodiments, the tracrRNA and pre-crRNAs are supplied via separate expression constructs or as separate RNAs. In other embodiments, a chimeric RNA is constructed where an engineered mature crRNA (conferring target specificity) is fused to a tracrRNA (supplying interaction with the Cas9) to create a chimeric cr-RNA-tracrRNA hybrid (also termed a single guide RNA). (see Jinek, ibid and Cong, ibid). Chimeric or sgRNAs can be engineered to comprise a sequence complementary to any desired target. The RNAs comprise 22 bases of complementarity to a target and of the form G[n19], followed by a protospacer-adjacent motif (PAM) of the form NGG. Thus, in one method, sgRNAs can be designed by utilization of a known ZFN target in a gene of interest by (i) aligning the recognition sequence of the ZFN heterodimer with the reference sequence of the relevant genome (human, mouse, or of a particular plant species); (ii) identifying the spacer region between the ZFN half-sites; (iii) identifying the location of the motif G[N20]GG that is closest to the spacer region (when more than one such motif overlaps the spacer, the motif that is centered relative to the spacer is chosen); (iv) using that motif as the core of the sgRNA. This method advantageously relies on proven nuclease targets. Alternatively, sgRNAs can be designed to target any region of interest simply by identifying a suitable target sequence that conforms to the G[n20]GG formula.

Target Sites

As described in detail above, DNA-binding domains can be engineered to bind to any sequence of choice in a locus, for example a globin or safe-harbor gene. An engineered DNA-binding domain can have a novel binding specificity, compared to a naturally-occurring DNA-binding domain. Engineering methods include, but are not limited to, rational design and various types of selection. Rational design includes, for example, using databases comprising triplet (or quadruplet) nucleotide sequences and individual (e.g., zinc finger) amino acid sequences, in which each triplet or quadruplet nucleotide sequence is associated with one or more amino acid sequences of DNA binding domain which bind the particular triplet or quadruplet sequence. See, for example, co-owned U.S. Pat. Nos. 6,453,242 and 6,534,261, incorporated by reference herein in their entireties. Rational design of TAL-effector domains can also be performed. See, e.g., U.S. Patent Publication No. 20110301073.

Exemplary selection methods applicable to DNA-binding domains, including phage display and two-hybrid systems, are disclosed in U.S. Pat. Nos. 5,789,538; 5,925,523; 6,007,988; 6,013,453; 6,410,248; 6,140,466; 6,200,759; and 6,242,568; as well as WO 98/37186; WO 98/53057; WO 00/27878; WO 01/88197 and GB 2,338,237.

Selection of target sites; nucleases and methods for design and construction of fusion proteins (and polynucleotides encoding same) are known to those of skill in the art and described in detail in U.S. Patent Application Publication Nos. 20050064474 and 20060188987, incorporated by reference in their entireties herein.

In addition, as disclosed in these and other references, DNA-binding domains (e.g., multi-fingered zinc finger proteins) may be linked together using any suitable linker sequences, including for example, linkers of 5 or more amino acids. See, e.g., U.S. Pat. Nos. 6,479,626; 6,903,185; and 7,153,949 for exemplary linker sequences 6 or more amino acids in length. The proteins described herein may include any combination of suitable linkers between the individual DNA-binding domains of the protein. See, also, U.S. Patent Publication No. 20110287512.

Donors

As noted above, insertion of an exogenous sequence (also called a "donor sequence" or "donor" or "transgene"), for example for correction of a mutant gene or for increased expression of a wild-type gene. It will be readily apparent that the donor sequence is typically not identical to the genomic sequence where it is placed. A donor sequence can contain a non-homologous sequence flanked by two regions of homology to allow for efficient HDR at the location of interest. Additionally, donor sequences can comprise a vector molecule containing sequences that are not homologous to the region of interest in cellular chromatin. A donor molecule can contain several, discontinuous regions of homology to cellular chromatin. For example, for targeted insertion of sequences not normally present in a region of interest, said sequences can be present in a donor nucleic acid molecule and flanked by regions of homology to sequence in the region of interest.

Described herein are methods of targeted insertion of any polynucleotides for insertion into a chosen location. Polynucleotides for insertion can also be referred to as "exogenous" polynucleotides, "donor" polynucleotides or molecules or "transgenes." The donor polynucleotide can be DNA or RNA, single-stranded and/or double-stranded and can be introduced into a cell in linear or circular form. See, e.g., U.S. Patent Publication Nos. 20100047805, 20110281361, 20110207221 and 20130326645. The donor sequence(s) can be contained within a DNA MC, which may be introduced into the cell in circular or linear form. If introduced in linear form, the ends of the donor sequence can be protected (e.g., from exonucleolytic degradation) by methods known to those of skill in the art. For example, one or more dideoxynucleotide residues are added to the 3' terminus of a linear molecule and/or self-complementary oligonucleotides are ligated to one or both ends. See, for example, Chang et al. (1987) *Proc. Natl. Acad. Sci. USA* 84:4959-4963; Nehls et al. (1996) *Science* 272:886-889. Additional methods for protecting exogenous polynucleotides from degradation include, but are not limited to, addition of terminal amino group(s) and the use of modified internucleotide linkages such as, for example, phosphorothioates, phosphoramidates, and O-methyl ribose or deoxyribose residues.

A polynucleotide can be introduced into a cell as part of a vector molecule having additional sequences such as, for example, replication origins, promoters and genes encoding antibiotic resistance. Moreover, donor polynucleotides can be introduced as naked nucleic acid, as nucleic acid complexed with an agent such as a liposome or poloxamer, or can be delivered by viruses (e.g., adenovirus, AAV, herpesvirus, retrovirus, lentivirus and integrase defective lentivirus (IDLV)).

In certain embodiments, the double-stranded donor includes sequences (e.g., coding sequences, also referred to as transgenes) greater than 1 kb in length, for example between 2 and 200 kb, between 2 and 10 kb (or any value therebetween). The double-stranded donor also includes at least one nuclease target site, for example. In certain embodiments, the donor includes at least 1 target site, for example, for use with a CRISPR/Cas, or 2 target sites, for example for a pair of ZFNs or TALENs. Typically, the nuclease target sites are outside the transgene sequences, for example, 5' and/or 3' to the transgene sequences, for cleavage of the transgene. The nuclease cleavage site(s) may be for any nuclease(s). In certain embodiments, the nuclease target site(s) contained in the double-stranded donor are for the same nuclease(s) used to cleave the endogenous target into which the cleaved donor is integrated via homology-independent methods.

The donor is generally inserted so that its expression is driven by the endogenous promoter at the integration site, namely the promoter that drives expression of the endogenous gene into which the donor is inserted (e.g., globin, AAVS1, etc.). However, it will be apparent that the donor may comprise a promoter and/or enhancer, for example a constitutive promoter or an inducible or tissue specific promoter.

The donor molecule may be inserted into an endogenous gene such that all, some or none of the endogenous gene is expressed. For example, a transgene as described herein may be inserted into a globin locus such that some or none of the endogenous globin sequences are expressed, for example as a fusion with the transgene. In other embodiments, the transgene (e.g., with or without globin encoding sequences) is integrated into any endogenous locus, for example a safe-harbor locus. See, e.g., US patent publications 20080299580; 20080159996 and 201000218264.

When additional (e.g., globin sequences, endogenous or part of the transgene) are expressed with the transgene, the additionally (e.g., globin) sequences may be full-length sequences (wild-type or mutant) or partial sequences. Preferably, the additional sequences are functional. Non-limiting examples of the function of these full length or partial additional sequences, for example globin-encoding sequences, include increasing the serum half-life of the polypeptide expressed by the transgene (e.g., therapeutic gene) and/or acting as a carrier.

Furthermore, although not required for expression, exogenous sequences may also include transcriptional or translational regulatory sequences, for example, promoters, enhancers, insulators, internal ribosome entry sites, sequences encoding 2A peptides and/or polyadenylation signals.

The transgenes carried on the donor sequences described herein may be isolated from plasmids, cells or other sources using standard techniques known in the art such as PCR. Donors for use can include varying types of topology, including circular supercoiled, circular relaxed, linear and the like. Alternatively, they may be chemically synthesized using standard oligonucleotide synthesis techniques. In addition, donors may be methylated or lack methylation. Donors may be in the form of bacterial or yeast artificial chromosomes (BACs or YACs).

The double-stranded donor polynucleotides described herein may include one or more non-natural bases and/or backbones. In particular, insertion of a donor molecule with methylated cytosines may be carried out using the methods described herein to achieve a state of transcriptional quiescence in a region of interest.

The exogenous (donor) polynucleotide may comprise any sequence of interest (exogenous sequence). Exemplary exogenous sequences include, but are not limited to any polypeptide coding sequence (e.g., cDNAs), promoter sequences, enhancer sequences, epitope tags, marker genes, cleavage enzyme recognition sites and various types of expression constructs. Marker genes include, but are not limited to, sequences encoding proteins that mediate antibiotic resistance (e.g., ampicillin resistance, neomycin resistance, G418 resistance, puromycin resistance), sequences encoding colored or fluorescent or luminescent proteins (e.g., green fluorescent protein, enhanced green fluorescent protein, red fluorescent protein, luciferase), and proteins which mediate enhanced cell growth and/or gene amplification (e.g., dihydrofolate reductase). Epitope tags include, for example, one or more copies of FLAG, His, myc, Tap, HA or any detectable amino acid sequence.

In a preferred embodiment, the exogenous sequence (transgene) comprises a polynucleotide encoding any polypeptide of which expression in the cell is desired, including, but not limited to antibodies, antigens, enzymes, receptors (cell surface or nuclear), hormones, lymphokines, cytokines, reporter polypeptides, growth factors, and functional fragments of any of the above. The coding sequences may be, for example, cDNAs.

In certain embodiments, the exogenous sequences can comprise a marker gene (described above), allowing selection of cells that have undergone targeted integration, and a linked sequence encoding an additional functionality. Non-limiting examples of marker genes include GFP, drug selection marker(s) and the like.

Additional gene sequences that can be inserted may include, for example, wild-type genes to replace mutated sequences. For example, a wild-type beta globin gene sequence may be inserted into the genome of a stem cell in which the endogenous copy of the gene is mutated. The wild-type copy may be inserted at the endogenous locus, or may alternatively be targeted to a safe harbor locus.

Construction of such expression cassettes, following the teachings of the present specification, utilizes methodologies well known in the art of molecular biology (see, for example, Ausubel or Maniatis). Before use of the expression cassette to generate a transgenic animal, the responsiveness of the expression cassette to the stress-inducer associated with selected control elements can be tested by introducing the expression cassette into a suitable cell line (e.g., primary cells, transformed cells, or immortalized cell lines).

Furthermore, although not required for expression, exogenous sequences may also transcriptional or translational regulatory sequences, for example, promoters, enhancers, insulators, internal ribosome entry sites, sequences encoding 2A peptides and/or polyadenylation signals. Further, the control elements of the genes of interest can be operably linked to reporter genes to create chimeric genes (e.g., reporter expression cassettes).

Targeted insertion of non-coding nucleic acid sequence may also be achieved. Sequences encoding antisense RNAs, RNAi, shRNAs and micro RNAs (miRNAs) may also be used for targeted insertions.

In additional embodiments, the donor nucleic acid may comprise non-coding sequences that are specific target sites for additional nuclease designs. Subsequently, additional nucleases may be expressed in cells such that the original donor molecule is cleaved and modified by insertion of another donor molecule of interest. In this way, reiterative integrations of donor molecules may be generated allowing for trait stacking at a particular locus of interest or at a safe harbor locus.

Delivery

The nucleases, polynucleotides encoding these nucleases, donor polynucleotides and compositions comprising the proteins and/or polynucleotides described herein may be delivered in vivo or ex vivo by any suitable means.

Methods of delivering nucleases as described herein are described, for example, in U.S. Pat. Nos. 6,453,242; 6,503,717; 6,534,261; 6,599,692; 6,607,882; 6,689,558; 6,824,978; 6,933,113; 6,979,539; 7,013,219; and 7,163,824, the disclosures of all of which are incorporated by reference herein in their entireties.

Nucleases and/or donor constructs as described herein may also be delivered using vectors containing sequences encoding one or more of the zinc finger or TALEN protein(s). Any vector systems may be used including, but not limited to, plasmid vectors, retroviral vectors, lentiviral vectors, adenovirus vectors, poxvirus vectors; herpesvirus vectors and adeno-associated virus vectors, etc. See, also, U.S. Pat. Nos. 6,534,261; 6,607,882; 6,824,978; 6,933,113; 6,979,539; 7,013,219; and 7,163,824, incorporated by reference herein in their entireties. Furthermore, it will be apparent that any of these vectors may comprise one or more of the sequences needed for treatment. Thus, when one or more nucleases and a donor construct are introduced into the cell, the nucleases and/or donor polynucleotide may be carried on the same vector or on different vectors. When multiple vectors are used, each vector may comprise a sequence encoding one or multiple nucleases and/or donor constructs.

Conventional viral and non-viral based gene transfer methods can be used to introduce nucleic acids encoding nucleases and donor constructs in cells (e.g., mammalian cells) and target tissues. Non-viral vector delivery systems include DNA plasmids, naked nucleic acid, and nucleic acid complexed with a delivery vehicle such as a liposome or poloxamer. Viral vector delivery systems include DNA and RNA viruses, which have either episomal or integrated genomes after delivery to the cell. For a review of gene therapy procedures, see Anderson, *Science* 256:808-813 (1992); Nabel & Felgner, *TIBTECH* 11:211-217 (1993); Mitani & Caskey, *TIBTECH* 11:162-166 (1993); Dillon, *TIBTECH* 11:167-175 (1993); Miller, *Nature* 357:455-460 (1992); Van Brunt, *Biotechnology* 6(10):1149-1154 (1988); Vigne, *Restorative Neurology and Neuroscience* 8:35-36 (1995); Kremer & Perricaudet, *British Medical Bulletin* 51(1):31-44 (1995); Haddada et al., in *Current Topics in Microbiology and Immunology* Doerfler and Bohm (eds.) (1995); and Yu et al., *Gene Therapy* 1:13-26 (1994).

Methods of non-viral delivery of nucleic acids include electroporation, lipofection, microinjection, biolistics, virosomes, liposomes, immunoliposomes, polycation or lipid:nucleic acid conjugates, naked DNA, artificial virions, and agent-enhanced uptake of DNA. Sonoporation using, e.g., the Sonitron 2000 system (Rich-Mar) can also be used for delivery of nucleic acids.

Additional exemplary nucleic acid delivery systems include those provided by Amaxa Biosystems (Cologne, Germany), Maxcyte, Inc. (Rockville, Md.), BTX Molecular Delivery Systems (Holliston, Mass.) and Copernicus Therapeutics Inc, (see for example U.S. Pat. No. 6,008,336). Lipofection is described in e.g., U.S. Pat. Nos. 5,049,386; 4,946,787; and 4,897,355) and lipofection reagents are sold commercially (e.g., Transfectam™ and Lipofectin™). Cationic and neutral lipids that are suitable for efficient receptor-recognition lipofection of polynucleotides include those of Felgner, WO 91/17424, WO 91/16024.

The preparation of lipid:nucleic acid complexes, including targeted liposomes such as immunolipid complexes, is well known to one of skill in the art (see, e.g., Crystal, *Science* 270:404-410 (1995); Blaese et al., *Cancer Gene Ther.* 2:291-297 (1995); Behr et al., *Bioconjugate Chem.* 5:382-389 (1994); Remy et al., *Bioconjugate Chem.* 5:647-654 (1994); Gao et al., *Gene Therapy* 2:710-722 (1995); Ahmad et al., *Cancer Res.* 52:4817-4820 (1992); U.S. Pat. Nos. 4,186,183, 4,217,344, 4,235,871, 4,261,975, 4,485,054, 4,501,728, 4,774,085, 4,837,028, and 4,946,787).

Additional methods of delivery include the use of packaging the nucleic acids to be delivered into EnGeneIC delivery vehicles (EDVs). These EDVs are specifically delivered to target tissues using bispecific antibodies where one arm of the antibody has specificity for the target tissue and the other has specificity for the EDV. The antibody brings the EDVs to the target cell surface and then the EDV is brought into the cell by endocytosis. Once in the cell, the contents are released (see MacDiarmid et al (2009) *Nature Biotechnology* 27(7):643).

The use of RNA or DNA viral based systems for the delivery of nucleic acids encoding engineered ZFPs take advantage of highly evolved processes for targeting a virus to specific cells in the body and trafficking the viral payload to the nucleus. Viral vectors can be administered directly to subjects (in vivo) or they can be used to treat cells in vitro and the modified cells are administered to subjects (ex vivo). Conventional viral based systems for the delivery of ZFPs include, but are not limited to, retroviral, lentivirus, adenoviral, adeno-associated, vaccinia and herpes simplex virus vectors for gene transfer. Integration in the host genome is possible with the retrovirus, lentivirus, and adeno-associated virus gene transfer methods, often resulting in long term expression of the inserted transgene. Additionally, high transduction efficiencies have been observed in many different cell types and target tissues.

The tropism of a retrovirus can be altered by incorporating foreign envelope proteins, expanding the potential target population of target cells. Lentiviral vectors are retroviral vectors that are able to transduce or infect non-dividing cells and typically produce high viral titers. Selection of a retroviral gene transfer system depends on the target tissue. Retroviral vectors are comprised of cis-acting long terminal repeats with packaging capacity for up to 6-10 kb of foreign sequence. The minimum cis-acting LTRs are sufficient for replication and packaging of the vectors, which are then used to integrate the therapeutic gene into the target cell to provide permanent transgene expression. Widely used retroviral vectors include those based upon murine leukemia virus (MuLV), gibbon ape leukemia virus (GaLV), Simian Immunodeficiency virus (SIV), human immunodeficiency virus (HIV), and combinations thereof (see, e.g., Buchscher et al., *J. Virol.* 66:2731-2739 (1992); Johann et al., *J. Virol.* 66:1635-1640 (1992); Sommerfelt et al., *Virol.* 176:58-59 (1990); Wilson et al., *J. Virol.* 63:2374-2378 (1989); Miller et al., *J. Virol.* 65:2220-2224 (1991); PCT/US94/05700).

In applications in which transient expression is preferred, adenoviral based systems can be used. Adenoviral based vectors are capable of very high transduction efficiency in many cell types and do not require cell division. With such vectors, high titer and high levels of expression have been obtained. This vector can be produced in large quantities in a relatively simple system. Adeno-associated virus ("AAV") vectors are also used to transduce cells with target nucleic acids, e.g., in the in vitro production of nucleic acids and peptides, and for in vivo and ex vivo gene therapy procedures (see, e.g., West et al., *Virology* 160:38-47 (1987); U.S. Pat. No. 4,797,368; WO 93/24641; Kotin, *Human Gene Therapy* 5:793-801 (1994); Muzyczka, *J. Clin. Invest.* 94:1351 (1994). Construction of recombinant AAV vectors are described in a number of publications, including U.S. Pat. No. 5,173,414; Tratschin et al., *Mol. Cell. Biol.* 5:3251-3260 (1985); Tratschin, et al., *Mol. Cell. Biol.* 4:2072-2081 (1984); Hermonat & Muzyczka, *PNAS* 81:6466-6470 (1984); and Samulski et al., *J. Virol.* 63:03822-3828 (1989).

At least six viral vector approaches are currently available for gene transfer in clinical trials, which utilize approaches that involve complementation of defective vectors by genes inserted into helper cell lines to generate the transducing agent.

pLASN and MFG-S are examples of retroviral vectors that have been used in clinical trials (Dunbar et al., *Blood* 85:3048-305 (1995); Kohn et al., *Nat. Med.* 1:1017-102 (1995); Malech et al., *PNAS* 94:22 12133-12138 (1997)). PA317/pLASN was the first therapeutic vector used in a gene therapy trial. (Blaese et al., *Science* 270:475-480 (1995)). Transduction efficiencies of 50% or greater have been observed for MFG-S packaged vectors. (Ellem et al., *Immunol Immunother.* 44(1):10-20 (1997); Dranoff et al., *Hum. Gene Ther.* 1:111-2 (1997).

Recombinant adeno-associated virus vectors (rAAV) are a promising alternative gene delivery systems based on the defective and nonpathogenic parvovirus adeno-associated type 2 virus. All vectors are derived from a plasmid that retains only the AAV 145 bp inverted terminal repeats flanking the transgene expression cassette. Efficient gene transfer and stable transgene delivery due to integration into the genomes of the transduced cell are key features for this vector system. (Wagner et al., *Lancet* 351:9117 1702-3 (1998), Kearns et al., *Gene Ther.* 9:748-55 (1996)). Other AAV serotypes, including AAV1, AAV3, AAV4, AAV5, AAV6, AAV8, AAV9 and AAVrh10, and all variants thereof, can also be used in accordance with the present invention.

Replication-deficient recombinant adenoviral vectors (Ad) can be produced at high titer and readily infect a number of different cell types. Most adenovirus vectors are engineered such that a transgene replaces the Ad E1a, E1b, and/or E3 genes; subsequently the replication defective vector is propagated in human 293 cells that supply deleted gene function in trans. Ad vectors can transduce multiple types of tissues in vivo, including non-dividing, differentiated cells such as those found in liver, kidney and muscle. Conventional Ad vectors have a large carrying capacity. An example of the use of an Ad vector in a clinical trial involved polynucleotide therapy for anti-tumor immunization with intramuscular injection (Sterman et al., *Hum. Gene Ther.* 7:1083-9 (1998)). Additional examples of the use of adenovirus vectors for gene transfer in clinical trials include Rosenecker et al., *Infection* 24:1 5-10 (1996); Sterman et al., *Hum. Gene Ther.* 9:7 1083-1089 (1998); Welsh et al., *Hum. Gene Ther.* 2:205-18 (1995); Alvarez et al., *Hum. Gene Ther.* 5:597-613 (1997); Topf et al., *Gene Ther.* 5:507-513 (1998); Sterman et al., *Hum. Gene Ther.* 7:1083-1089 (1998).

Packaging cells are used to form virus particles that are capable of infecting a host cell. Such cells include 293 cells, which package adenovirus, and ψ2 cells or PA317 cells, which package retrovirus. Viral vectors used in gene therapy are usually generated by a producer cell line that packages a nucleic acid vector into a viral particle. The vectors typically contain the minimal viral sequences required for packaging and subsequent integration into a host (if applicable), other viral sequences being replaced by an expression cassette encoding the protein to be expressed. The missing viral functions are supplied in trans by the packaging cell line. For example, AAV vectors used in gene therapy typically only possess inverted terminal repeat (ITR) sequences from the AAV genome which are required for packaging and integration into the host genome. Viral DNA is packaged in a cell line, which contains a helper plasmid encoding the other AAV genes, namely rep and cap, but lacking ITR sequences. The cell line is also infected with adenovirus as a helper. The helper virus promotes replication of the AAV vector and expression of AAV genes from the helper plasmid. The helper plasmid is not packaged in significant amounts due to a lack of ITR sequences. Contamination with adenovirus can be reduced by, e.g., heat treatment to which adenovirus is more sensitive than AAV.

In many gene therapy applications, it is desirable that the gene therapy vector be delivered with a high degree of specificity to a particular tissue type. Accordingly, a viral vector can be modified to have specificity for a given cell type by expressing a ligand as a fusion protein with a viral coat protein on the outer surface of the virus. The ligand is chosen to have affinity for a receptor known to be present on the cell type of interest. For example, Han et al., *Proc. Natl. Acad. Sci. USA* 92:9747-9751 (1995), reported that Moloney murine leukemia virus can be modified to express human heregulin fused to gp70, and the recombinant virus infects certain human breast cancer cells expressing human epidermal growth factor receptor. This principle can be extended to other virus-target cell pairs, in which the target cell expresses a receptor and the virus expresses a fusion protein comprising a ligand for the cell-surface receptor. For example, filamentous phage can be engineered to display antibody fragments (e.g., FAB or Fv) having specific binding affinity for virtually any chosen cellular receptor. Although the above description applies primarily to viral vectors, the same principles can be applied to nonviral vectors. Such vectors can be engineered to contain specific uptake sequences which favor uptake by specific target cells.

Gene therapy vectors can be delivered in vivo by administration to an individual subject, typically by systemic administration (e.g., intravenous, intraperitoneal, intramuscular, subdermal, or intracranial infusion) or topical application, as described below. Alternatively, vectors can be delivered to cells ex vivo, such as cells explanted from an individual patient (e.g., lymphocytes, bone marrow aspirates, tissue biopsy) or universal donor hematopoietic stem cells, followed by reimplantation of the cells into a patient, usually after selection for cells which have incorporated the vector.

Vectors (e.g., retroviruses, adenoviruses, liposomes, etc.) containing nucleases and/or donor constructs can also be administered directly to an organism for transduction of cells in vivo. Alternatively, naked DNA can be administered. Administration is by any of the routes normally used for introducing a molecule into ultimate contact with blood or tissue cells including, but not limited to, injection, infusion, topical application and electroporation. Suitable methods of administering such nucleic acids are available and well known to those of skill in the art, and, although more than one route can be used to administer a particular composition, a particular route can often provide a more immediate and more effective reaction than another route.

Vectors suitable for introduction of polynucleotides described herein include non-integrating lentivirus vectors (IDLV). See, for example, Ory et al. (1996) *Proc. Natl. Acad. Sci. USA*_93:11382-11388; Dull et al. (1998) *J. Virol.* 72:8463-8471; Zuffery et al. (1998) *J. Virol.* 72:9873-9880; Follenzi et al. (2000) *Nature Genetics* 25:217-222; U.S. Patent Publication No WO 2009/054985.

Pharmaceutically acceptable carriers are determined in part by the particular composition being administered, as well as by the particular method used to administer the composition. Accordingly, there is a wide variety of suitable formulations of pharmaceutical compositions available, as described below (see, e.g., *Remington's Pharmaceutical Sciences,* 17th ed., 1989).

It will be apparent that the nuclease-encoding sequences and donor constructs can be delivered using the same or different systems. For example, a donor polynucleotide can be carried by a plasmid, while the one or more nucleases can be carried by a AAV vector. Furthermore, the different vectors can be administered by the same or different routes (intramuscular injection, tail vein injection, other intravenous injection, intraperitoneal administration and/or intramuscular injection. The vectors can be delivered simultaneously or in any sequential order.

Thus, the instant disclosure includes in vivo or ex vivo treatment of diseases and conditions that are amenable to insertion of a transgenes encoding a therapeutic protein, for example treatment of hemoglobinopathies via nuclease-mediated integration of a gene encoding a globin protein. The compositions are administered to a human patient in an amount effective to obtain the desired concentration of the therapeutic polypeptide in the serum or the target organ or cells. Administration can be by any means in which the polynucleotides are delivered to the desired target cells. For example, both in vivo and ex vivo methods are contemplated. Intravenous injection to the portal vein is a preferred method of administration. Other in vivo administration modes include, for example, direct injection into the lobes of the liver or the biliary duct and intravenous injection distal to the liver, including through the hepatic artery, direct injection in to the liver parenchyma, injection via the hepatic artery, and/or retrograde injection through the biliary tree. Ex vivo modes of administration include transduction in vitro of resected hepatocytes or other cells of the liver, followed by infusion of the transduced, resected hepatocytes back into the portal vasculature, liver parenchyma or biliary tree of the human patient, see e.g., Grossman et al., (1994) *Nature Genetics,* 6:335-341.

The effective amount of nuclease(s) and donor to be administered will vary from patient to patient and according to the therapeutic polypeptide of interest. Accordingly, effective amounts are best determined by the physician administering the compositions and appropriate dosages can be determined readily by one of ordinary skill in the art. After allowing sufficient time for integration and expression (typically 4-15 days, for example), analysis of the serum or other tissue levels of the therapeutic polypeptide and comparison to the initial level prior to administration will determine whether the amount being administered is too low, within the right range or too high. Suitable regimes for initial and subsequent administrations are also variable, but are typified by an initial administration followed by subsequent administrations if necessary. Subsequent administrations may be administered at variable intervals, ranging from daily to annually to every several years. One of skill in the art will appreciate that appropriate immunosuppressive techniques may be recommended to avoid inhibition or blockage of transduction by immunosuppression of the delivery vectors, see e.g., Vilquin et al., (1995) *Human Gene Ther.* 6:1391-1401.

Formulations for both ex vivo and in vivo administrations include suspensions in liquid or emulsified liquids. The active ingredients often are mixed with excipients which are pharmaceutically acceptable and compatible with the active ingredient. Suitable excipients include, for example, water, saline, dextrose, glycerol, ethanol or the like, and combinations thereof. In addition, the composition may contain minor amounts of auxiliary substances, such as, wetting or emulsifying agents, pH buffering agents, stabilizing agents or other reagents that enhance the effectiveness of the pharmaceutical composition.

Applications

The methods and compositions disclosed herein are for modifying expression of protein, or correcting an aberrant gene sequence that encodes a protein expressed in a genetic disease, such as a sickle cell disease or a thalassemia. Thus, the methods and compositions provide for the treatment and/or prevention of such genetic diseases. Genome editing, for example of stem cells, is used to correct an aberrant gene, insert a wild type gene, or change the expression of an endogenous gene. By way of non-limiting example, a wild type gene, e.g. encoding at least one globin (e.g., α and/or β globin), may be inserted into a cell to provide the globin proteins deficient and/or lacking in the cell and thereby treat a genetic disease, e.g., a hemoglobinopathy, caused by faulty globin expression. Alternatively or in addition, genomic editing with or without administration of the appropriate donor, can correct the faulty endogenous gene, e.g., correcting the point mutation in α- or β-hemoglobin, to restore expression of the gene and/or treat a genetic disease, e.g. sickle cell disease and/or knock out or alteration (overexpression or repression) of any direct or indirect globin regulatory gene (e.g. inactivation of the γ globin-regulating gene BCL11A or the BCL11A-regulator KLF1).

The methods and compositions of the invention can also be used in any circumstance wherein it is desired to supply a transgene encoding one or more therapeutics such that the therapeutic(s) is(are) produced in a RBC and/or hematopoietic stem cell such that mature RBCs derived from these cells contain the therapeutic.

The following Examples relate to exemplary embodiments of the present disclosure in which the nuclease comprises a zinc finger nuclease (ZFN) or a TALEN. It will be appreciated that this is for purposes of exemplification only and that other nucleases can be used, for instance homing endonucleases (meganucleases) with engineered DNA-binding domains and/or fusions of naturally occurring of engineered homing endonucleases (meganucleases) DNA-binding domains and heterologous cleavage domains and/or a CRISPR/Cas system comprising an engineered single guide RNA.

EXAMPLES

Example 1: Design, Construction and General Characterization of Zinc Finger Protein Nucleases (ZFN)

Zinc finger proteins were designed and incorporated into plasmids, AAV or adenoviral vectors essentially as described in Urnov et al. (2005) *Nature* 435(7042):646-651, Perez et al (2008) *Nature Biotechnology* 26(7):808-816, and as described in U.S. Pat. No. 6,534,261. For ZFNs and TALENs specific for the human beta globin locus and the human HPRT locus, see co-owned U.S. Pat. No. 7,888,121 and U.S. Patent Publication Nos. 20130137104 and 20130122591. For nucleases specific for human AAVS1, see co-owned U.S. Pat. No. 8,110,379. For nucleases specific for CCR5, see co-owned U.S. Pat. No. 7,951,925. For nucleases specific for albumin, see U.S. Patent Publication Nos. 20130177983 and 2013901779608.

Example 2: Activity of Globin-Specific ZFNs

ZFN pairs targeting the human globin locus or regulators of beta-like globin gene expression were used to test the ability of these ZFNs to induce DSBs at a specific target site. The amino acid sequences of the recognition helix regions of each finger of the indicated ZFNs are shown below in Table 1A along with the whole target sites (DNA target sites indicated in uppercase letters; non-contacted nucleotides indicated in lowercase).

TABLE 1A

Zinc finger nucleases

| SBS #, Target | F1 | F2 | F3 | F4 | F5 | F6 |
|---|---|---|---|---|---|---|
| | | | Design | | | |
| Human B-Hemoglobin specific ZFNs | | | | | | |
| SBS#33511<br>ggGCAGTAACGGC<br>AGACttctcctca<br>gg<br>(SEQ ID NO: 8) | DRSNLSR<br>(SEQ ID NO: 9) | QSSDLRR<br>(SEQ ID NO: 10) | RSDTLSA<br>(SEQ ID NO: 11) | QSGALAR<br>(SEQ ID NO: 12) | QSGDLTR<br>(SEQ ID NO: 13) | N/A |
| SBS#33533<br>tgGGGCAAGGTGA<br>ACGTGGAtgaagt<br>tg<br>(SEQ ID NO: 14) | QSAHRKN<br>(SEQ ID NO: 15) | LKHHLTD<br>(SEQ ID NO: 16) | QRSNLVR<br>(SEQ ID NO: 17) | TSGHLSR<br>(SEQ ID NO: 18) | QSNHLTE<br>(SEQ ID NO: 19) | RSHHLKA<br>(SEQ ID NO: 20) |
| SBS#35256<br>agAGTCAGGTGCA<br>CCATggtgtctgt<br>tt<br>(SEQ ID NO: 21) | TNQNRIT<br>(SEQ ID NO: 22) | DRSNRTT<br>(SEQ ID NO: 23) | RNASRTR<br>(SEQ ID NO: 24) | RSDNLSE<br>(SEQ ID NO: 25) | RSQHRKT<br>(SEQ ID NO: 26) | N/A |
| SBS#35263<br>gtGGAGAAGTCtG<br>CCGTTactgccct<br>gt(SEQ ID NO: 27) | TSGSLSR<br>(SEQ ID NO: 28) | DRSDLSR<br>(SEQ ID NO: 29) | DRSALAR<br>(SEQ ID NO: 30) | QSSNLAR<br>(SEQ ID NO: 31) | QSGHLSR<br>(SEQ ID NO: 32) | N/A |
| SBS#34770<br>acAGGAGTCAGGT<br>GCACcatggtgtc<br>tg(SEQ ID NO: 33) | DQSNLRA<br>(SEQ ID NO: 34) | RNASRTR<br>(SEQ ID NO: 24) | RSDNLSE<br>(SEQ ID NO: 25) | RSQHRKT<br>(SEQ ID NO: 26) | RSDHLTQ<br>(SEQ ID NO: 35) | N/A |
| SBS#34791<br>gaGAAGTCtGCCG<br>TTACTgccctgtg<br>gg(SEQ ID NO: 36) | ARSTRTN<br>(SEQ ID NO: 37) | TSGSLSR<br>(SEQ ID NO: 28) | DRSDLSR<br>(SEQ ID NO: 29) | DRSARTR<br>(SEQ ID NO: 38) | QSGNLAR<br>(SEQ ID NO: 39) | N/A |

TABLE 1A-continued

Zinc finger nucleases

Design

| SBS #, Target | F1 | F2 | F3 | F4 | F5 | F6 |
|---|---|---|---|---|---|---|
| SBS#34805 taACGGCAGACtT CTCCAcaggagtc ag (SEQ ID NO: 40) | QSGDLTR (SEQ ID NO: 13) | SSSDRKK (SEQ ID NO: 41) | DRSNLSR (SEQ ID NO: 9) | QSADRTK (SEQ ID NO: 42) | RSDTLSA (SEQ ID NO: 11) | N/A |
| SBS#34826 gcCCTGTGGGGCA AGGTgaacgtgga tg (SEQ ID NO: 43) | LRHHLTR (SEQ ID NO: 44) | QSGNLHV (SEQ ID NO: 45) | RSAHLSR (SEQ ID NO: 46) | RSDVLST (SEQ ID NO: 47) | RKQDLRT (SEQ ID NO: 48) | N/A |
| SBS#35301 ggGCAGTAACGGC AGACttctcctca gg (SEQ ID NO: 8) | DRSNLSR (SEQ ID NO: 9) | QSGDLTR (SEQ ID NO: 13) | RSDTLSA (SEQ ID NO: 11) | QSGALAR (SEQ ID NO: 12) | QSGDLTR (SEQ ID NO: 13) | N/A |
| SBS#35328 tgGGGCAAGGTGA ACGTggatgaagt tg (SEQ ID NO: 14) | MSHHLRD (SEQ ID NO: 49) | QRSNLVR (SEQ ID NO: 17) | TSGHLSR (SEQ ID NO: 18) | QSNHLTE (SEQ ID NO: 19) | RSHHLKA (SEQ ID NO: 20) | N/A |
| SBS#35497 caCAGGGCAGTAA CgGCAGACttctc ct (SEQ ID NO: 50) | DRSNLSR (SEQ ID NO: 9) | QSGDLTR (SEQ ID NO: 13) | DRSNLSR (SEQ ID NO: 9) | LKHHLTD (SEQ ID NO: 16) | DRSHLTR (SEQ ID NO: 51) | RSDNLRE (SEQ ID NO: 52) |
| SBS#35506 ggCAAGGTGAACG TGGAtgaagttgg tg (SEQ ID NO: 53) | QSGHLAR (SEQ ID NO: 54) | VSHHLRD (SEQ ID NO: 55) | QSGNLAR (SEQ ID NO: 39) | LRHHLTR (SEQ ID NO: 44) | QSGNLHV (SEQ ID NO: 45) | N/A |

Beta-globin IVS.1

| SBS #, Target | F1 | F2 | F3 | F4 | F5 | F6 |
|---|---|---|---|---|---|---|
| SBS#43545 atCAAGGTTACAA GACAGGTttaagg ag (SEQ ID NO: 158) | LRHHLTR (SEQ ID NO: 44) | QSGTRKT (SEQ ID NO: 153) | RSDNLST (SEQ ID NO: 154) | DSANRIK (SEQ ID NO: 155) | LRHHLTR (SEQ ID NO: 44) | QSGNLHV (SEQ ID NO: 45) |
| SBS#43544 aaTCTGCCCAGGG CCTCaccaccaac tt (SEQ ID NO: 159) | AMQTLRV (SEQ ID NO: 156) | DRSHLAR (SEQ ID NO: 76) | RSDNLSE (SEQ ID NO: 25) | ASKTRKN (SEQ ID NO: 77) | RNSDRTK (SEQ ID NO: 157) | N/A |

Human BCL11A specific ZFNs
Exon 2

| SBS #, Target | F1 | F2 | F3 | F4 | F5 | F6 |
|---|---|---|---|---|---|---|
| SBS#39172 ctCCAGAAGGGGA TCATGACctcctc ac (SEQ ID NO: 160) | DRSNLSR (SEQ ID NO: 9) | LRQNLIM (SEQ ID NO: 161) | TSANLTV (SEQ ID NO: 162) | RSDHLSR (SEQ ID NO: 94) | QSGNLAR (SEQ ID NO: 39) | QRNDRKS (SEQ ID NO: 163) |
| SBS#43490 ctCCAGAAGGGGA TCATGACctcctc ac (SEQ ID NO: 160) | DRSNLSR (SEQ ID NO: 9) | LRQNLIM (SEQ ID NO: 161) | LQSQLNR (SEQ ID NO: 164) | RSDHLSR (SEQ ID NO: 94) | QSGNLAR (SEQ ID NO: 39) | QRNDRKS (SEQ ID NO: 163) |
| SBS#44642 ctCCAGAAGGGGA TCATGACctcctc ac (SEQ ID NO: 160) | DRANLSR (SEQ ID NO: 165) | LRQNLIM (SEQ ID NO: 161) | LQSQLNR (SEQ ID NO: 164) | RSDHLSR (SEQ ID NO: 94) | QSGNLAR (SEQ ID NO: 39) | QRNDRKS (SEQ ID NO: 163) |

TABLE 1A-continued

Zinc finger nucleases

| SBS #, Target | Design | | | | | |
|---|---|---|---|---|---|---|
| | F1 | F2 | F3 | F4 | F5 | F6 |
| SBS#45148 ctCCAGAAGGGGA TCATGACctcctc ac(SEQ ID NO: 160) | DRSNLSR (SEQ ID NO: 9) | TSSNRNH (SEQ ID NO: 166) | HSGNLTK (SEQ ID NO: 167) | RSDHLSR (SEQ ID NO: 94) | QSGNLAR (SEQ ID NO: 39) | QKVDLSR (SEQ ID NO: 168) |
| SBS#45147 ctCCAGAAGGGGA TCATGACctcctc ac(SEQ ID NO: 160) | DRSNLSR (SEQ ID NO: 9) | TSSNRNH (SEQ ID NO: 166) | QANNLKV (SEQ ID NO: 169) | RSDHLSR (SEQ ID NO: 94) | QSGNLAR (SEQ ID NO: 39) | QKVDLSR (SEQ ID NO: 168) |
| SBS#39145 ccCAACGGGCCGT GGTCTGGttcatc at(SEQ ID NO: 170) | RSDHLSA (SEQ ID NO: 59) | DRSALAR (SEQ ID NO: 30) | RSDSLSR (SEQ ID NO: 171) | DRSVRTK (SEQ ID NO: 172) | RSDHLSA (SEQ ID NO: 59) | QRSNLKV (SEQ ID NO: 173) |
| SBS#44490 ccCAACGGGCCGT GGTCTGGttcatc at(SEQ ID NO: 170) | RSDHLTQ (SEQ ID NO: 35) | DRSALAR (SEQ ID NO: 30) | RSDSLSR (SEQ ID NO: 171) | DRSVRTK (SEQ ID NO: 172) | RSDHLSA (SEQ ID NO: 59) | QRSNLKV (SEQ ID NO: 173) |
| SBS#44489 ccCAACGGGCCGT GGTCTGGttcatc at(SEQ ID NO: 170) | RSDHLTT (SEQ ID NO: 174) | DRSALAR (SEQ ID NO: 30) | RSDSLSR (SEQ ID NO: 171) | DRSVRTK (SEQ ID NO: 172) | RSDHLSA (SEQ ID NO: 59) | QRSNLKV (SEQ ID NO: 173) |
| SBS#45081 ccCAACGGGCCGT GGTCTGGttcatc at(SEQ ID NO: 170) | RSDHLSA (SEQ ID NO: 59) | WATARDR (SEQ ID NO: 175) | RSDSLSR (SEQ ID NO: 171) | HTKSLSR (SEQ ID NO: 176) | RSDHLSA (SEQ ID NO: 59) | QRSNLKV (SEQ ID NO: 173) |
| SBS#44493 ccCAACGGGCCGT GGTCTGGttcatc at(SEQ ID NO: 170) | RSAHLTQ (SEQ ID NO: 177) | DRSVLRR (SEQ ID NO: 178) | RSDSLSR (SEQ ID NO: 171) | DRSVRTK (SEQ ID NO: 172) | RSDHLSA (SEQ ID NO: 59) | QRSNLKV (SEQ ID NO: 173) |
| SBS#29527 atCCCATGGAGAG GTGGCTGggaagg ac(SEQ ID NO: 56) | RSDVLSE (SEQ ID NO: 57) | RNQHRKT (SEQ ID NO: 58) | RSDHLSA (SEQ ID NO: 59) | RSANLTR (SEQ ID NO: 60) | RSDVLSN (SEQ ID NO: 61) | DRSTRIT (SEQ ID NO: 62) |
| SBS#29528 atATTGCAGACAA TAACcccttttaac ct(SEQ ID NO: 63) | DRSNLSR (SEQ ID NO: 9) | HRQHLVT (SEQ ID NO: 64) | DRSNLTR (SEQ ID NO: 65) | QSGDLTR (SEQ ID NO: 13) | HRSSLLN (SEQ ID NO: 66) | N/A |
| SBS# 29525 caTCCCAGGCGTG GGGAttagagctc ca(SEQ ID NO: 66) | QSGHLSR (SEQ ID NO: 32) | RSDHLST (SEQ ID NO: 67) | RSADLSR (SEQ ID NO: 68) | RSDNLSQ (SEQ ID NO: 69) | ASNDRKK (SEQ ID NO: 70) | N/A |
| SBS#29526 gtGCAGAATATGC CCCGCAGggtatt tg(SEQ ID NO: 71) | RSDNLSA (SEQ ID NO: 72) | RNNDRKT (SEQ ID NO: 73) | DRSDLSR (SEQ ID NO: 29) | TSSNRTK (SEQ ID NO: 74) | QSGNLAR (SEQ ID NO: 39) | QSGDLTR (SEQ ID NO: 13) |
| Exon4 | | | | | | |
| SBS#34678 atATTGCAGACAA TAACcccttttaac ct(SEQ ID NO: 179) | DRSNLSR (SEQ ID NO: 9) | HRQHLVT (SEQ ID NO: 64) | DRSNLTR (SEQ ID NO: 65) | QSGDLTR (SEQ ID NO: 13) | HRWLRSN (SEQ ID NO: 180) | N/A |

TABLE 1A-continued

Zinc finger nucleases

| SBS #, Target | Design | | | | | |
|---|---|---|---|---|---|---|
| | F1 | F2 | F3 | F4 | F5 | F6 |
| SBS#34642<br>atCCCATGgAGAG<br>GTGGCTGGaagg<br>ac(SEQ ID<br>NO: 56) | RSDHLSQ<br>(SEQ ID<br>NO: 99) | DSSHRTR<br>(SEQ ID<br>NO: 181) | LRHHLTR<br>(SEQ ID<br>NO: 44) | QSAHLKA<br>(SEQ ID<br>NO: 182) | RSDVLSN<br>(SEQ ID<br>NO: 61) | DRSTRIT<br>(SEQ ID<br>NO: 62) |

Bcl11a-XL

| SBS #, Target | F1 | F2 | F3 | F4 | F5 | F6 |
|---|---|---|---|---|---|---|
| SBS#44889<br>ctCACTGTCCACA<br>GGAGaagccacac<br>gg(SEQ ID<br>NO: 183) | RSANLAR<br>(SEQ ID<br>NO: 184) | RLDNRTA<br>(SEQ ID<br>NO: 185) | QSNDLNS<br>(SEQ ID<br>NO: 186) | WRSSLKT<br>(SEQ ID<br>NO: 187) | DRSNRKT<br>(SEQ ID<br>NO: 188) | N/A |
| SBS#44888<br>ttGCTACAGTTCT<br>TGAAGActttccc<br>ac(SEQ ID<br>NO: 189) | DRSNLSR<br>(SEQ ID<br>NO: 9) | QSGNLAR<br>(SEQ ID<br>NO: 39) | YKHVLSD<br>(SEQ ID<br>NO: 190) | TSGSLTR<br>(SEQ ID<br>NO: 191) | QSGDLTR<br>(SEQ ID<br>NO: 13) | LKDTLRR<br>(SEQ ID<br>NO: 192) |
| SBS#44905*<br>gaGAAGCCACACG<br>GGCGAAAggcctt<br>at(SEQ ID<br>NO: 193) | QSGNLDS<br>(SEQ ID<br>NO: 194) | RSADLSR<br>(SEQ ID<br>NO: 68) | RSDHLSE<br>(SEQ ID<br>NO: 78) | QNATRIN<br>(SEQ ID<br>NO: 195) | WNSDLRK<br>(SEQ ID<br>NO: 196) | QSGNLAR<br>(SEQ ID<br>NO: 39) |
| SBS#44904*<br>tgGACAGTGAGAT<br>TGCTacagttctt<br>ga(SEQ ID<br>NO: 197) | QSSDLSR<br>(SEQ ID<br>NO: 88) | YKWTLRN<br>(SEQ ID<br>NO: 198) | RSANLTR<br>(SEQ ID<br>NO: 60) | TSTKLRT<br>(SEQ ID<br>NO: 199) | DRSNLTR<br>(SEQ ID<br>NO: 65) | N/A |
| SBS#44911<br>gcCACACGGGCGA<br>AaGGCCTTataaa<br>tg(SEQ ID<br>NO: 200) | AMQTLRV<br>(SEQ ID<br>NO: 156) | DRSHLAR<br>(SEQ ID<br>NO: 76) | QRSNLVR<br>(SEQ ID<br>NO: 17) | DRSHLAR<br>(SEQ ID<br>NO: 76) | RSDTLST<br>(SEQ ID<br>NO: 201) | DSSNRIN<br>(SEQ ID<br>NO: 202) |
| SBS#44910<br>ctCCTGTGGACAG<br>TGAGATTgctaca<br>gt(SEQ ID<br>NO: 203) | NDLFLYL<br>(SEQ ID<br>NO: 204) | RSANLTR<br>(SEQ ID<br>NO: 60) | TSTKLRT<br>(SEQ ID<br>NO: 199) | DRSNLTR<br>(SEQ ID<br>NO: 65) | RSDSLSV<br>(SEQ ID<br>NO: 205) | HNDSRKN<br>(SEQ ID<br>NO: 206) |
| SBS#44945<br>aaGCTCACCAGGC<br>ACATGAAaacgca<br>tg(SEQ ID<br>NO: 207) | QSGNLAR<br>(SEQ ID<br>NO: 39) | CRQNLAN<br>(SEQ ID<br>NO: 208) | YQGVLTR<br>(SEQ ID<br>NO: 209) | RSDNLRE<br>(SEQ ID<br>NO: 52) | DRSNRTT<br>(SEQ ID<br>NO: 23) | HRSSLRR<br>(SEQ ID<br>NO: 210) |
| SBS#44944<br>ctACTCTGgGCAC<br>AGGCATAGttgca<br>ca(SEQ ID<br>NO: 211) | RSDNLST<br>(SEQ ID<br>NO: 154) | QSSDLRR<br>(SEQ ID<br>NO: 10) | RSDALSE<br>(SEQ ID<br>NO: 212) | QNATRTK<br>(SEQ ID<br>NO: 115) | RSDTLSE<br>(SEQ ID<br>NO: 84) | ARSTRTN<br>(SEQ ID<br>NO: 37) |
| SBS#44947**<br>ctCACCAGGCACA<br>TGAAAACgcatgg<br>cc(SEQ ID<br>NO: 213) | GSSALTQ<br>(SEQ ID<br>NO: 214) | QSGNLAR<br>(SEQ ID<br>NO: 39) | TASHLKE<br>(SEQ ID<br>NO: 215) | QNATRTK<br>(SEQ ID<br>NO: 115) | RSDNLSE<br>(SEQ ID<br>NO: 25) | SSRNLAS<br>(SEQ ID<br>NO: 216) |
| SBS#44946**<br>ctACTCTGgGCAC<br>AGGCATAGttgca<br>ca(SEQ ID<br>NO: 211) | RSDNLST<br>(SEQ ID<br>NO: 154) | QSSDLRR<br>(SEQ ID<br>NO: 10) | RSDALSE<br>(SEQ ID<br>NO: 212) | QNATRTK<br>(SEQ ID<br>NO: 115) | RSDTLSE<br>(SEQ ID<br>NO: 84) | ARSTRTN<br>(SEQ ID<br>NO: 37) |

TABLE 1A-continued

Zinc finger nucleases

| SBS #, Target | F1 | F2 | F3 | F4 | F5 | F6 |
|---|---|---|---|---|---|---|
| | | | Design | | | |

Human KLF1 specific ZFNs
KLF- Exon1

| SBS #, Target | F1 | F2 | F3 | F4 | F5 | F6 |
|---|---|---|---|---|---|---|
| SBS#36004 ggGAAGGGGCCCA GGGCGGTcagtgt gc (SEQ ID NO: 75) | TSGHLSR (SEQ ID NO: 18) | DRSHLAR (SEQ ID NO: 76) | RSDNLSQ (SEQ ID NO: 69) | ASNDRKK (SEQ ID NO: 70) | RSDHLSE SEQ ID NO: 78) | QSGNLAR (SEQ ID NO: 39) |
| SBS#36021 acACACAGGATGA Cttcctcaaggtg gg (SEQ ID NO: 79) | DRSNLTR (SEQ ID NO: 65) | TSANLSR (SEQ ID NO: 217) | RSDHLSE (SEQ ID NO: 78) | QSASRKN (SEQ ID NO: 81) | NA | NA |
| SBS#33237 ggGAAGGGGCCCA GGGCGGTcagtgt gc (SEQ ID NO: 75) | TSGHLSR (SEQ ID NO: 18) | DRSHLAR (SEQ ID NO: 76) | RSDNLSE (SEQ ID NO: 25) | ASKTRKN (SEQ ID NO: 77) | RSDHLSE (SEQ ID NO: 78) | QSGNLAR (SEQ ID NO: 39) |
| SBS#33238 acACACAGGATGA Cttcctcaaggtg gg (SEQ ID NO: 79) | DRSNLSR (SEQ ID NO: 9) | TSGNLTR (SEQ ID NO: 80) | RSDHLSE (SEQ ID NO: 78) | QSASRKN (SEQ ID NO: 81) | N/A | N/A |
| SBS#33257 cgCCACCGGGCTC CGGGcccgagaag tt (SEQ ID NO: 82) | RSAHLSR (SEQ ID NO: 46) | DSSDRKK (SEQ ID NO: 83) | DRSHLAR (SEQ ID NO: 76) | RSDTLSE (SEQ ID NO: 84) | QSGDLTR (SEQ ID NO: 13) | N/A |
| SBS#33258 ccCCAGACcTGCG CTCTGGCGcccag cg (SEQ ID NO: 85) | RSDSLLR (SEQ ID NO: 86) | RLDWLPV (SEQ ID NO: 87) | QSSDLSR (SEQ ID NO: 88) | AASNRSK (SEQ ID NO: 89) | DRSNLSR (SEQ ID NO: 9) | QSGDLTR (SEQ ID NO: 13) |
| SBS#33269 ggCTCGGGgGCCG GGGCTGGAgccag gg (SEQ ID NO: 90) | QSSHLTR (SEQ ID NO: 91) | QSSDLTR (SEQ ID NO: 92) | RSDHLSE (SEQ ID NO: 78) | HSRTRTK (SEQ ID NO: 93) | RSDHLSR (SEQ ID NO: 94) | DRSARNS (SEQ ID NO: 95) |
| SBS#33270 aaGGCGCTGGCGC TgCAACCGgtgta cc (SEQ ID NO: 96) | RSDTLSE (SEQ ID NO: 84) | QSHNRTK (SEQ ID NO: 97) | QSSDLSR (SEQ ID NO: 88) | DRSHLAR (SEQ ID NO: 76) | QSSDLSR (SEQ ID NO: 88) | DRSHLAR (SEQ ID NO: 76) |
| SBS#33271 ttGCAGCGCCAGC GCCTTGGgctcgg gg (SEQ ID NO: 98) | RSDHLSQ (SEQ ID NO: 99) | HRSSLGD (SEQ ID NO: 100) | RSDDLTR (SEQ ID NO: 101) | QRSTLSS (SEQ ID NO: 102) | RSADLTR (SEQ ID NO: 103) | QSGDLTR (SEQ ID NO: 13) |
| SBS#33272 cgGTGTACCCGGG GCCCggcgccggc tc (SEQ ID NO: 104) | DRSDLSR (SEQ ID NO: 29) | RSTHLVR (SEQ ID NO: 105) | RSDSLST (SEQ ID NO: 106) | DSSDRTK (SEQ ID NO: 107) | RSAALAR (SEQ ID NO: 108) | N/A |

TABLE 1A-continued

Zinc finger nucleases

| SBS #, Target | Design | | | | | |
|---|---|---|---|---|---|---|
| | F1 | F2 | F3 | F4 | F5 | F6 |

KLF- Exon2

| SBS #, Target | F1 | F2 | F3 | F4 | F5 | F6 |
|---|---|---|---|---|---|---|
| SBS#36071 ggTGAGGAGGAGA TCCAggtcccagg tg(SEQ ID NO: 218) | NNRDLIN (SEQ ID NO: 219) | TSSNLSR (SEQ ID NO: 220) | QSGHLSR (SEQ ID NO: 32) | QSGHLAR (SEQ ID NO: 54) | QRTHLNS SEQ ID NO: 221) | N/A |
| SBS#36085 ctTCTCGGGCCCG GaGCCCGGtggcg cg(SEQ ID NO: 222) | RSDHLSE (SEQ ID NO: 78) | HSRTRTK (SEQ ID NO: 93) | RSDHLSE (SEQ ID NO: 78) | HSRTRTK (SEQ ID NO: 93) | RSDHLSE (SEQ ID NO: 78) | RKSDRIK (SEQ ID NO: 223) |

Human gamma globin 5' regulatory region ZFNs
regulatory region (-175)

| SBS #, Target | F1 | F2 | F3 | F4 | F5 | F6 |
|---|---|---|---|---|---|---|
| SBS#34360 ttGCATTGAGATA GTGTGGGaagggg gc(SEQ ID NO: 109) | RSDHLSV (SEQ ID NO: 110) | RSDVRKT (SEQ ID NO: 111) | RSDYLSK (SEQ ID NO: 112) | TSSVRTT (SEQ ID NO: 113) | RPYTLRL (SEQ ID NO: 114) | QNATRTK (SEQ ID NO: 115) |
| SBS#34363 atCTGTCTGAAAC GGTCcctggctaa ac(SEQ ID NO: 116) | DRSALAR (SEQ ID NO: 30) | RRDILHQ (SEQ ID NO: 117) | QSGNLAR (SEQ ID NO: 39) | LAYDRRK (SEQ ID NO: 118) | RSDVLSE (SEQ ID NO: 57) | N/A |
| SBS#34398 ttTGCATTGAGAT AGTGtggggaagg gg(SEQ ID NO: 119) | RSDSLLR (SEQ ID NO: 86) | QSCARNV (SEQ ID NO: 120) | RSDNLAR (SEQ ID NO: 121) | HRNTLLG (SEQ ID NO: 122) | MRNRLNR (SEQ ID NO: 123) | N/A |
| SBS#34400 ctGTCTGAaACGG TCcCTGGCTaaac tc(SEQ ID NO: 124) | QSSDLSR (SEQ ID NO: 88) | RRDALLM (SEQ ID NO: 125) | DRSALAR (SEQ ID NO: 30) | RRDILHQ (SEQ ID NO: 117) | QNAHRKT (SEQ ID NO: 126) | DRSALAR (SEQ ID NO: 30) |
| SBS#31160 taTTTGCAttGAG ATAGTGTGgggaa gg(SEQ ID NO: 127) | RSDSLLR (SEQ ID NO: 86) | LQHHLTD (SEQ ID NO: 128) | TSGNLTR (SEQ ID NO: 80) | TSTHLHI (SEQ ID NO: 129) | QSGDLTR (SEQ ID NO: 13) | HKWVLRQ (SEQ ID NO: 130) |
| SBS#34365 ctGTCTGAaACGG TCcCTGGCTaaac tc(SEQ ID NO: 124) | QSSDLSR (SEQ ID NO: 88) | RRDALLM (SEQ ID NO: 131) | DRSALAR (SEQ ID NO: 30) | RRDILHQ (SEQ ID NO:117) | QNAHRKT (SEQ ID NO: 126) | DRSALAR (SEQ ID NO: 30) | regulatory region (-110)

| SBS #, Target | F1 | F2 | F3 | F4 | F5 | F6 |
|---|---|---|---|---|---|---|
| SBS#34539 tgGTCAAGGCAAG GCTGgccaaccca tg(SEQ ID NO: 224) | RSDVLSE (SEQ ID NO: 57) | RNQHRKT (SEQ ID NO: 58) | QSGDLTR (SEQ ID NO: 13) | RSDHLST (SEQ ID NO: 67) | DRSALAR (SEQ ID NO: 30) | NA |
| SBS#34574 gcCTTGACAAGGC AAACttgaccaat ag(SEQ ID NO: 225) | DRSNRTT (SEQ ID NO: 23) | QSGSLTR (SEQ ID NO: 226) | RSDNLSV (SEQ ID NO: 227) | DRSNLSR (SEQ ID NO: 9) | LKFALAN (SEQ ID NO: 228) | NA |
| SBS#43865 gcCTTGACAAGGC AAACttgaccaat ag(SEQ ID NO: 225) | NPANLTR (SEQ ID NO: 229) | QNATRTK (SEQ ID NO: 115) | RSDNLSV (SEQ ID NO: 227) | DRSNLSR (SEQ ID NO: 9) | LKFALAN (SEQ ID NO: 228) | NA |

TABLE 1A-continued

Zinc finger nucleases

| SBS #, Target | Design | | | | | |
|---|---|---|---|---|---|---|
| | F1 | F2 | F3 | F4 | F5 | F6 |
| SBS#43852 tgGTCAAGGCAAG GCTGgccaaccca tg(SEQ ID NO: 224) | RSDVLSE (SEQ ID NO: 57) | RNQHRKT (SEQ ID NO: 58) | QSGDLTR (SEQ ID NO: 13) | RSDNLST (SEQ ID NO: 154) | DSSARKK (SEQ ID NO: 230) | NA |

Note:
BCL11A XL-specific ZFN pairs marked with a single asterisk (*) or with a double asterisk (**) contain the novel linkers L7a and L8p, respectively. See Example 6.

The Cel-I assay (Surveyor™, Transgenomics) as described in Perez et al. (2008) *Nat. Biotechnol.* 26: 808-816 and Guschin et al. (2010) *Methods Mol Biol.* 649:247-56), was used to detect ZFN-induced modifications of the target gene in K562 or HSCs. In this assay, PCR-amplification of the target site was followed by quantification of insertions and deletions (indels) using the mismatch detecting enzyme Cel-I (Yang et al. (2000) *Biochemistry* 39: 3533-3541) which provided a lower-limit estimate of DSB frequency. Three days following transfection of the ZFN expression vector at either standard conditions (37° C.) or using a hypothermic shock (30° C., see co-owned US patent publication U.S. Patent Publication No. 20110041195), genomic DNA was isolated from K562 cells using the DNeasy kit (Qiagen).

The results from the Cel-I assay demonstrated that the ZFNs were capable of inducing cleavage at their respective target sites (see, also, co-owned U.S. Publication No. 20130137104). The results are shown in FIG. 1 and indicate that active proteins were found for most of the target loci in the beta globin gene.

Example 3: Editing of the Beta Globin Locus

The human beta globin gene (HBB) specific ZFNs (Table 1) were used to introduce a donor DNA into the beta globin locus as follows. Donor DNAs were designed such that the sequence encoding HBB gene sequences is flanked by sequences that were homologous (homology arms) to the region surrounding the ZFN cleavage site in the beta globin gene. The homology arms are approximately 500-600 base pairs in length. The HBB donor sequence lacks any noncoding sequence such that when inserted into the beta globin target site, the expression of the donor is regulated by the beta globin promoter and any other beta globin regulatory sequences. When inserted, the HBB donor is fused in frame with the endogenous globin sequences and results in a fusion protein. In addition, a HBB donor oligo was designed for capture into the cleaved HBB gene following ZFN treatment. The oligo contained a restriction site such that following insertion of the oligo, a novel restriction site was introduced into the HBB gene that could subsequently be cleaved.

As shown in FIG. 2A, the β globin oligo donor was inserted into the proper locus, as verified by the presence of the novel restriction site present on the donor DNA. Furthermore, as shown in FIG. 2B, Cel-I analysis shows that several of the ZFN pairs were able to cleave the DNA although the oligo was present only in the sample in lane 8.

To differentiate the transgenic CD34+ cells into mature RBCs, methods known in the art are used. For example, SCD CD34+ cells are purified using Ficoll-Paque (GE Healthcare) and CD34+ microbeads (Miltenyi Biotec) according to the manufacturers' instructions. CD34+ cells are cultured in Iscove's MDM with BIT 95000 (StemCell Technologies) in the presence of growth factors. Cells are differentiated toward the erythroid lineage using a 2-phase liquid culture model. During the first 6 days (first phase), CD34+ cells are expanded with SCF (100 ng/ml), Flt3-L (100 ng/ml), and IL-3 (20 ng/ml). Expanded cells are then committed and differentiated toward the erythroid lineage (second phase) with Epo (2 U/ml) and SCF (50 ng/ml). See, Giarratana et al. (2011) *Blood* 118(19):5071-9.

Example 4: Gene Correction of the Mutations in Beta Globin

To correct the human sickle cell mutation in the sickle beta globin gene, a double-strand break was made in the beta-globin locus with a ZFN followed by DNA repair using an exogenous corrective oligonucleotide as a template (a "donor oligo"). To avoid the possibility of the nucleases cleaving a corrected globin gene (one in which the donor oligo has directed correction of the sickle mutation in the endogenous HBB gene), an donor oligo was designed to co-introduce translationaly silent mutations into the HBB coding sequence so that the corrected alleles would lack one of the ZFN target sequences. In this way, an increase in the frequency of the desired gene corrected allele would be observed. To design the optimal oligonucleotide donor, several mutations in the ZFN target sequence were investigated as well as length of the homology arms.

Below, the sequence surrounding the sickle mutation is shown and the various mutations are indicated with numbers. Thus, mutation 1=G to A change, mutation 2=G to A, mutation 3=TCT to AGC, mutation 4=C to T and mutation 5=T to G. Oligonucleotides were generated which comprised various combinations of the mutations. The wild-type sequence ("wt") is indicated on top (SEQ ID NO:231) and the sequence with the mutations ("mut") is indicated below (SEQ ID NO:232).

Target sites for the nucleases ("target") are indicated by heavy lines, and the site of the sickle mutation is boxed. Oligonucleotides are labeled according to the mutations, thus, for example, oligonucleotide SMS1 has only silent mutation site 1 present, while SMS 124 has the silent mutation sites 1, 2 and 4 present.

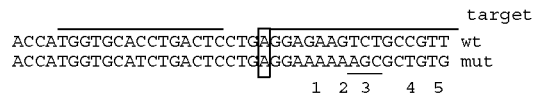

The various oligos were delivered to CD34+ cells as single stranded molecules either as 'sense' or forward strands (indicated as 'F') or 'antisense' or reverse strands (indicated as 'R'). The oligos were delivered via transfection with a BTX ECM 830 Square Wave device either with or without nucleases. Unless indicated otherwise, 3 µg of nucleases were delivered. Gene editing was measured by high-throughput DNA sequencing of PCR amplicons of the HBB gene. Percent gene modification by non-homologous end joining ("NHEJ", caused by the healing of a double stranded break in the DNA following ZFN-induced cleavage) or targeted integration of the oligo following ZFN cleavage ("gene correction") is indicated (see FIG. 9). The results indicate that some combinations of mutations were able to enhance gene correction in the cells such that up to 20% of the cells displayed gene correction at the sickle locus.

Figure 10:
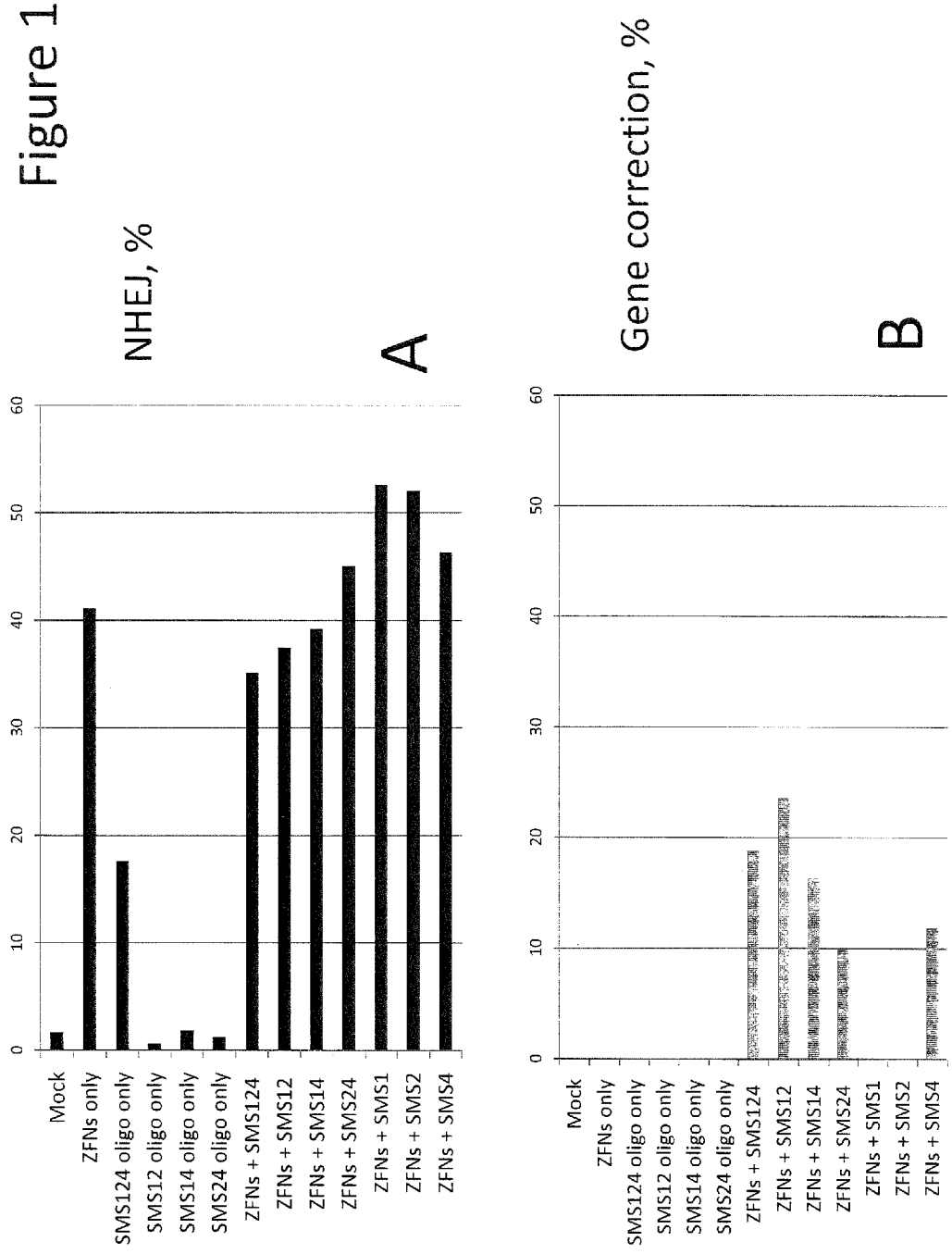
FIG. 10, panels A and B, depict the amount of NHEJ (i.e., targeted locus disruption that results from an NHEJ-based repair event of the nuclease-targeted break) and gene correction detected for the beta globin gene in CD34+ cells using the indicated zinc finger nuclease and oligonucleotide donors.

To investigate the effect of homology arm length on the percentage of gene correction, the SMS12 and SMS 124 oligos were used with either 41 and 46 nucleotides (the 88 bp donor oligo) or 50 and 50 nucleotides of homology (the 101 bp donor oligo) on either side of the sickle mutation site. The results (see FIG. 10) indicated that the longer homology arms were more effective at causing gene correction with up to 40% of alleles incorporating the changes specified by the oligo. The oligos used are shown below:

```
SMS124, 88 bp, R (SEQ ID NO: 233):
5' CGTTCACCTTGCCCCACAGGGCAGTAACAGCAGATTTTTCCTCAGGAGTCAGGTGCACCATGG

TGTCTGTTTGAGGTTGCTAGTGAAC

SMS12, 88 bp, R (SEQ ID NO: 234):
5' CGTTCACCTTGCCCCACAGGGCAGTAACGGCAGATTTTTCCTCAGGAGTCAGGTGCACCATGG

TGTCTGTTTGAGGTTGCTAGTGAAC

SMS124, 101 bp, R (SEQ ID NO: 235):
5' CTTCATCCACGTTCACCTTGCCCCACAGGGCAGTAACAGCAGATTTTTCCTCAGGAGTCAGGT

GCACCATGGTGTCTGTTTGAGGTTGCTAGTGAACACAG
```

Figure 11:
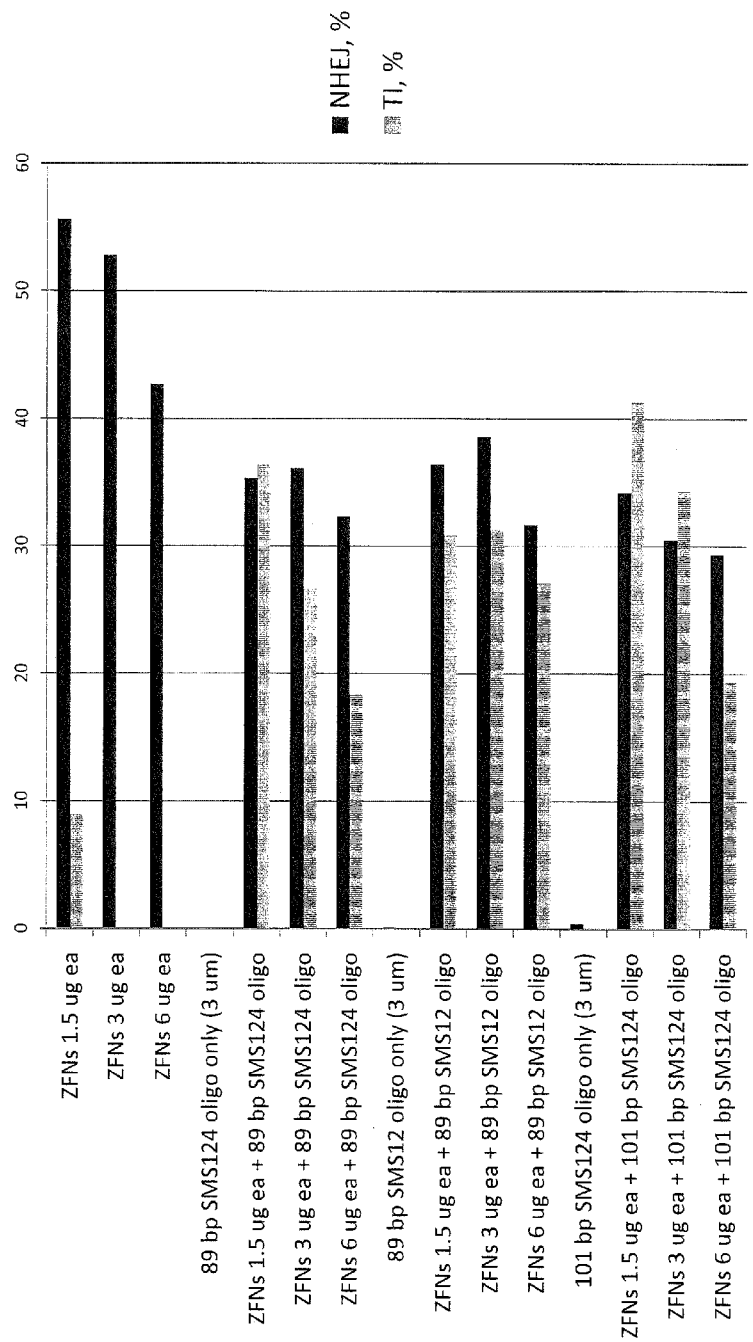
FIG. 11 depicts the amount of NHEJ and targeted integration of a donor nucleotide in CD34+ cells where the homology arms on the donor are varied.
Figure 12:
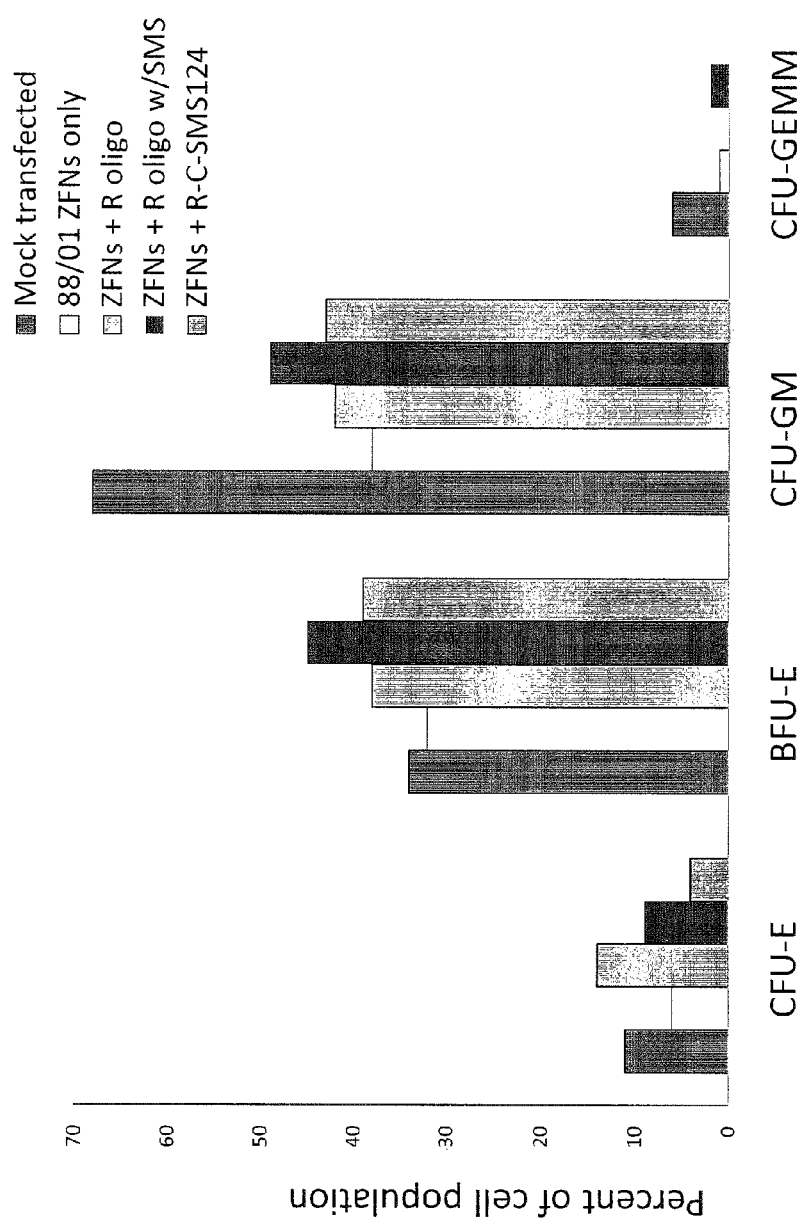
FIG. 12 depicts the persistence of gene editing in erythroid derivatives of stem cells that have been treated with ZFNs and oligonucleotide donor. Gene modification was analyzed in four types of cell populations arising from the differentiation, colony-forming units, erythroid ("CFU-E"), burst-forming units, erythroid ("BFU-E"), colony-forming units, granulocyte/macrophage ("CFU-GM") and colony-forming units, granulocyte/erythrocyte/monocyte/macrophage ("CFU-GEMM").
Figure 13:
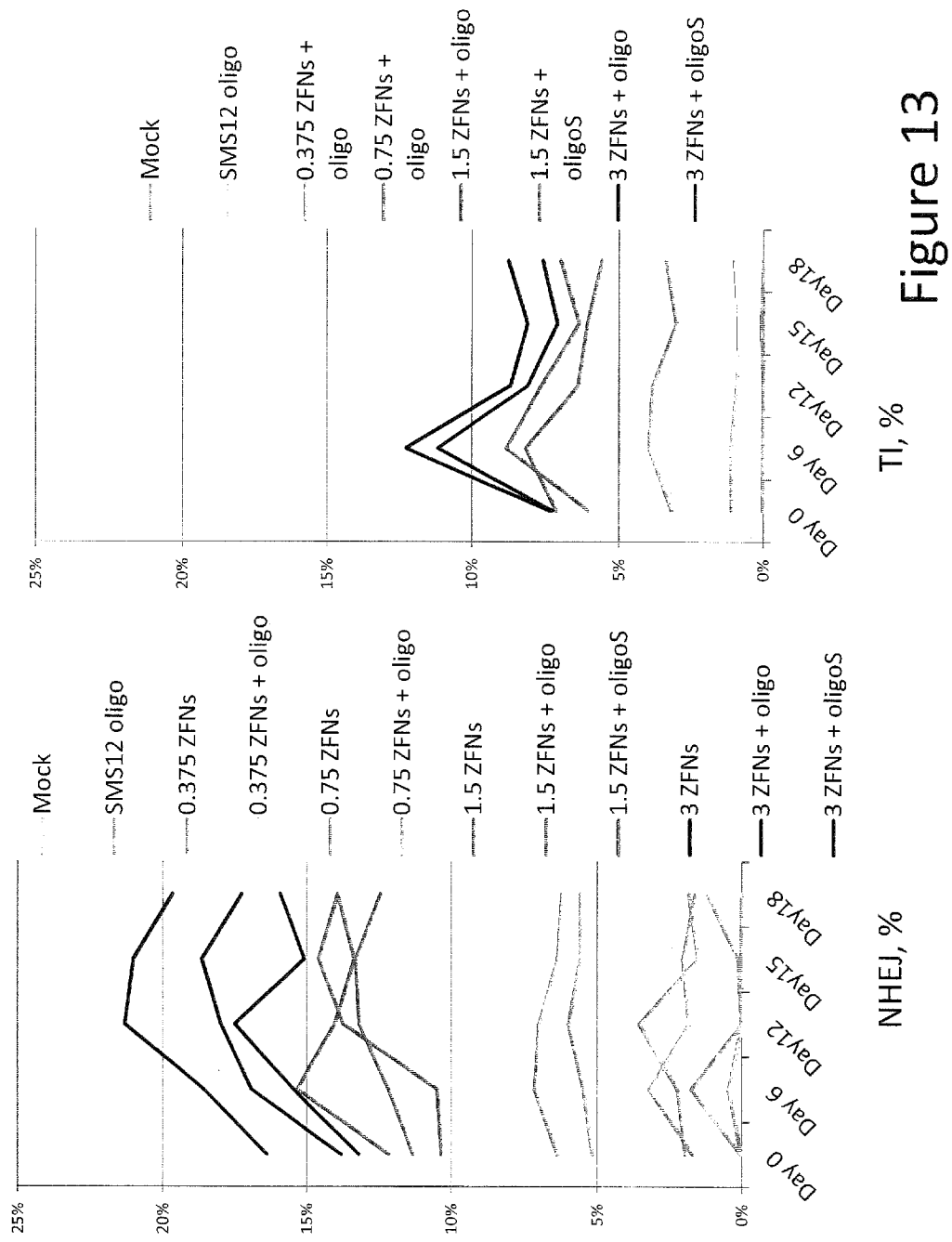
FIG. 13 depicts the stability of gene modification of the beta globin gene over time.

To investigate the differentiation capacity and the longevity of gene correction during CD34+ cell differentiation, pools of ZFN-modified CD34+ cells were induced to differentiate using Stemcell Technologies' Methocult methylcellulose medium according to manufacturer's directions. Differentiation was analyzed by assay off colony types arising from Methocult-induced differentiation: colony-forming units, erythroid ("CFU-E"); burst-forming units, erythroid ("BFU-E"); colony-forming units, granulocyte/macrophage ("CFU-GM") and colony-forming units; granulocyte/erythrocyte/monocyte/macrophage ("CFU-GEMM"). The results indicated that ZFN-treated cells retain the same capacity to differentiate as mock-transfected cells. Individual BFU-E colonies were picked from the plate and genotyped at HBB. The results indicated that the ZFN-induced modifications were maintained during colony differentiation (see FIG. 11). Further, the frequency of modified BFU-E colonies was similar to the frequency of modified alleles in the starting pool, demonstrating that there is no bias against edited cells during BFU-E formation. Additionally, the cell population as a whole was assayed for gene modification over the course of liquid culture in vitro red blood cell differentiation. The modifications were stable throughout for at least the 18 day red blood cell differentiation process (see FIG. 12).

Another common mutation in the beta globin gene that is associated with beta-thalassemia is known as IVS1.1. This G→A mutation is located within the first base pair of intron 1 of the beta globin gene, and its presence in the gene results in faulty splicing of the beta globin pre-mRNA. Thus, a pair of ZFNs was engineered to recognize and cleave the region, essentially recapitulating this mutation for model purposes. Testing of these ZFNs found that they were able to cleave the site in the beta globin gene resulting in 52.63% NHEJ in CD34+ cells.

Example 5: Insertion of a Beta-Globin Donor into a Safe Harbor Locus

To insert a wild type beta-globin gene into a safe harbor locus, such that expression from the transgene will correct a beta globin deficit in a HSC, nucleases specific to that safe harbor locus are introduced into the cell along with a donor nucleic acid. Nucleases specific for HPRT (see co-owned U.S. Patent Publication Nos. 20130137104 and 20130122591), AAVS1 (see U.S. Pat. No. 8,110,379), CCR5 (see U.S. Pat. No. 7,951,925) or beta-globin (see Table 1A) are introduced into a patient derived CD34+ stem cell. Introduction can be through any method known in the art such as mRNA electroporation. The donor DNA is designed to contain the transgene, wild type beta-globin, and regions of homology flanking the transgene with sufficient homology with the region surrounding the safe harbor target to allow for HDR (typically 500 bp on each side). Alternatively, a donor construct can be provided that, whether it lacks or contains regions of homology, is integrated into the ZFN or TALEN-targeted locus via end-capture (see U.S. Publication No. 20130326645). The donor is co-introduced into the CD34+ cell either prior, during or after the introduction of the ZFN. The modified CD34+ cells are the re-introduced into the patient and after engraftment, produce beta hemoglobin at sufficient levels to allow a therapeutically relevant amount of hemoglobin to be produced.

Example 6: Inactivation of BCL11A and KLF1

Figure 3:
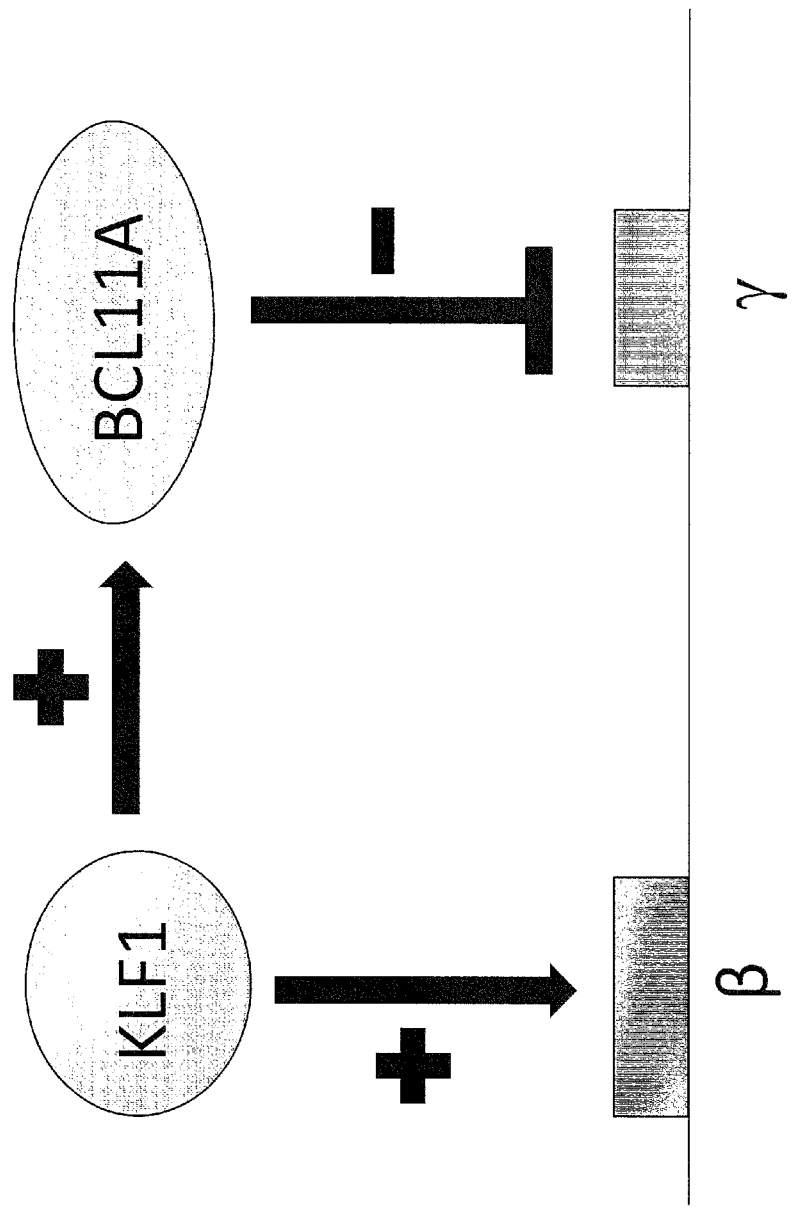
FIG. 3 is a graphic depicting the roles that KLF1 and BCL11A play in the regulation of β and gamma globin gene expression. Expression of KLF1 stimulates expression of both the BCL11a and β globin genes. The BCL11A protein represses gamma-globin expression.

Nucleases specific for BCL11A and KLF1 (e.g., ZFNs as shown in Table 1A) were introduced into HSCs as described above to cause an up regulation of gamma globin expression (see FIG. 3) and the genome of the cells analyzed by Cel 1 assay as described above (Perez et al (2008), ibid).

Figure 4:
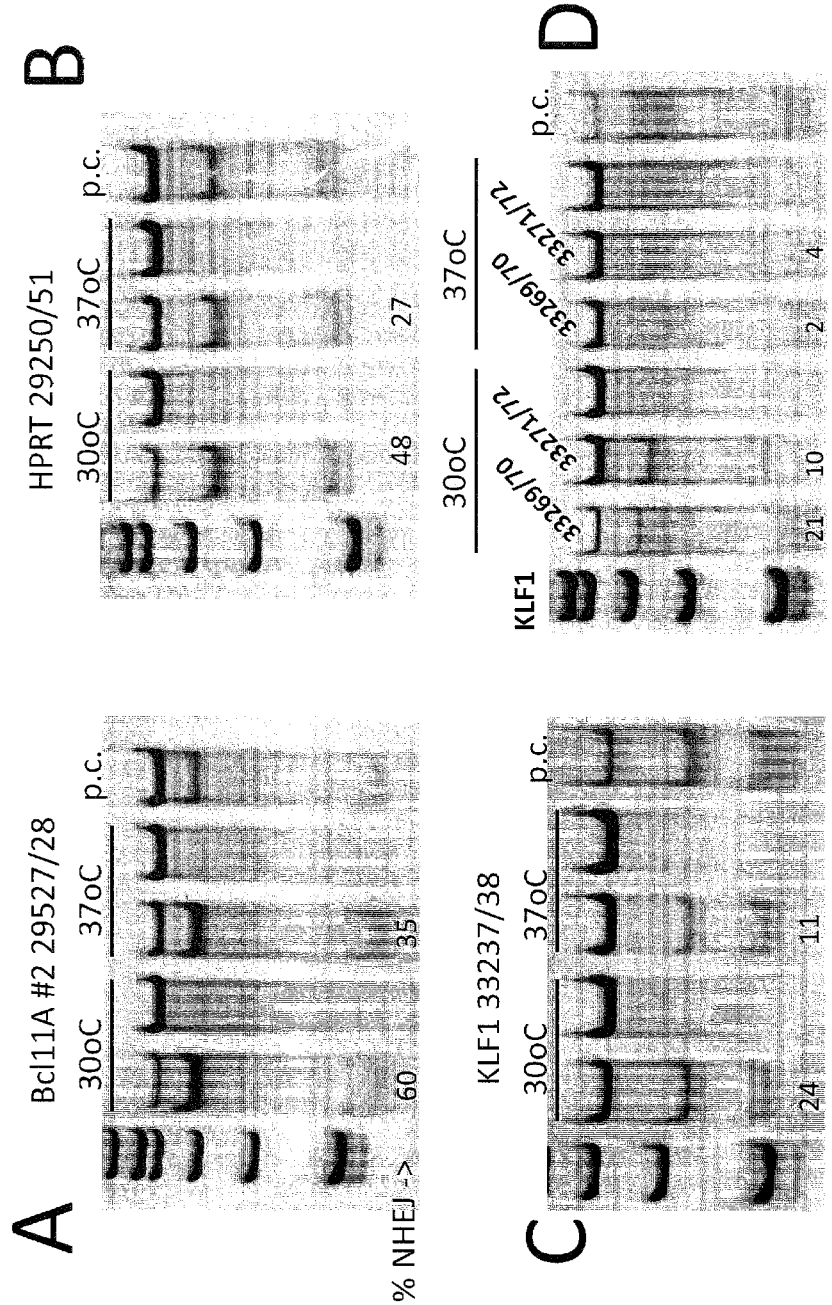
FIG. 4, panels A through E, depict gels showing the results of a Cel 1 assay as described above following treatment of HSCs with the indicated BCL11A—(FIG. 4A), KLF1—(FIGS. 4C and 4D) or HPRT—(FIG. 4B) specific ZFNs and either treating the transduced cells with a brief hypothermic shock (30°) or under standard conditions (37°). DNA was harvested 3 days after transfection.
Figure 4:
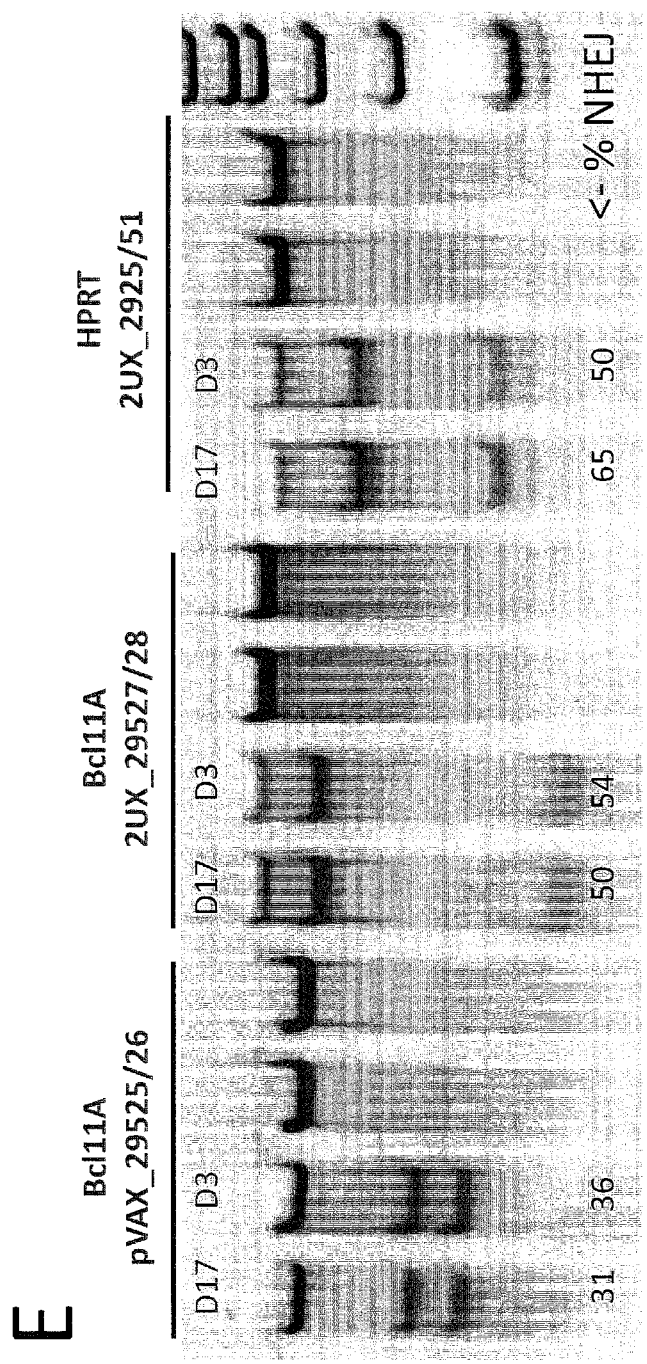

As shown in FIG. 4, following treatment of HSC with the indicated KLF1-specific ZFNs, the ZFNs successfully modified the KLF1 locus (FIGS. 4C and 4D). Likewise, BCL11A-specific ZFNs modified the BCL11A locus (FIG. 4A). A pair of ZFNs targeting the HPRT locus (see co-owned U.S. provisional application 61/552,309) were used as a control and also demonstrated successful cleavage (FIG. 4B). Comparison of the signal at day 3 following CD34+ cell transduction with day 17 of differentiation culture (FIG. 4E) demonstrated that the percentage of gene editing (% NHEJ) is stable over time. In each gel shown in FIG. 4E, the lanes lacking identification are negative controls.

Additional pairs of ZFNs, either targeting BCL11A exon 2 or exon 4 were similarly tested. For these studies, the candidate ZFN pairs were introduced into K562 cells by Amaxa as described previously or were introduced into CD34+ cells. For the CD34+ transduction, a BTX ECM830 device with a 2 mm gap cuvette was used. mRNAs from the cells were prepared using a mMessageMachine T7 Ultra Kit (#AM1345, Ambion). Human CD34+ cells were grown in x-vivo 10 media (Lonza) with 1×CC110 (Stem cell Technology) in non-tissue culture treated plates. The cells were counted and collected by centrifugation at 1200 rpm for 10 minutes at room temperature. The cells were washed 1-2× with room temperature PBS. 200,000 cells were used for each transfection, and they were resuspended in 100 μL BTexpress solution. 2-4 μg mRNA was added per transfection and the mixture was transferred to the cuvette. Immediately following transfer, the mixture was electroporated at 250V for 5 msec. Pre-warmed media was added to the cuvette and the media plus cells were transferred to a 48 well non-tissue culture treated plates and then incubated at 37° C.

After the specified number of days, the cells were then were subject to genome analysis using an Illumina MiSeq. To quantitate the percent of edited alleles, the genomic region of interest was PCR amplified using primers which add the standard Illumina sequencing adapter sequences. A second group of 13 rounds of PCR was performed to add barcode and bridge adapter sequences to both ends. Sequencing was performed on an Illumina MiSeq according to manufacturer's protocols for amplicon sequencing. The MiSeq generates paired-end reads, which are merged and adapter-trimmed using a standard alignment software. Reads were then demultiplexed by sample via barcode sequence pairs using custom scripts. Amplicon sequences were then globally aligned to a reference sequence via an implementation of the Needleman-Wunsch algorithm (Needleman, Saul B.; and Wunsch, Christian D. (1970). *Jour Mol Bio* 48 (3): 443-53). Gaps or insertions in the alignment were counted as % NHEJ events, and compared to an untreated control sample sequence to determine sequence-specific background rates.

For calculation of targeted integration, Amplicon sequences were globally aligned to a reference sequence via a biopython implementation of the Needleman-Wunsch algorithm (Needleman, Saul B.; and Wunsch, Christian D. ibid). Sequence changes generated via experimental treatments were searched for, counted, and compared to counts in control samples. Known single feature polymorphisms (SFPs) may be masked out during this process and excluded from further counts (e.g., 1-bp deletion SFPs close to the ZFN target site). NHEJ % (also referred to as indels) was calculated by determining the percentage of sequences that contain insertions or deletions. Samples treated only with GFP vector were used to assess the PCR and sequencing error based background frequency of insertions and deletions. Background frequencies of less than 1% were observed.

A representative data set is shown below in Table 1B and demonstrated that these nuclease proteins are active in cleaving their targets. In addition, expression of gamma globin was monitored in some of the nuclease treated cells. To perform this analysis, real time RT-qPCR ("Taqman") was used as per standard procedure (see below). The results from a representative data set are displayed as the fold increase in expression of gamma globin as compared to GFP treated control cells. The gamma values are calculated as a ratio of gamma globin to alpha globin, so any observed increase shown below represents an increase in the ratio of gamma to alpha in nuclease treated cells compared to the ratio of gamma to alpha in GFP vector treated cells.

TABLE 1B

Activity of BCL11A exon 2 and exon 4 ZFN pairs

| Target | ZFN pair | % indels, K562 | % indels, CD34+ | Fold increase in gamma mRNA |
|---|---|---|---|---|
| Exon 2 | 39145/39172 |  | 69.78 | 3.65X |
|  | 39145/43490 | 19.88 |  | nd |
|  | 39145/44642 | 38.52 |  | nd |
|  | 39145/45148 | 42.26 |  | nd |
|  | 39145/45147 | 35.63 |  | nd |
|  | 44490/39172 | 29.38 |  | nd |
|  | 44489/39172 | 24.34 |  | nd |
|  | 45081/39172 | 27.80 |  | nd |
|  | 44493/39172 | 25.68 |  | nd |
| Exon 4 | 34678/34642 |  | 82.24 | 3.52X |

TALENs were also made to both the exon2 and exon4 regions of BCL11A. The TALENs were constructed as described previously, using the canonical TALE code and the '+17' TALEN backbone (see co-owned U.S. Patent publication 20110301073). Table 1C shows the target sequence for the TALENs as well as the RVD sequence in the DNA binding domain.

TABLE 1C

TALEN pairs against BCL11A

| SBS number (exon) | Target Sequence 5'->3' | RVD sequence (N->C) |
|---|---|---|
| 101291 (exon 2) | ctGTGGGCAGTGCCAGATga (SEQ ID NO: 236) | NN-NG-NN-NN-NN-HD-NI-NN-NG-NN-HD-HD-NI-NN-NI-NG (SEQ ID NO: 237) |
| 101292 (exon 2) | ctCGATAAAAATAAGAATgt (SEQ ID NO: 238) | HD-NN-NI-NG-NI-NI-NI-NI-NI-NG-NI-NI-NN-NI-NI-NG (SEQ ID NO: 239) |
| 101301 (exon 4) | atGTCCTTCCCAGCCACCTct (SEQ ID NO: 240) | NN-NG-HD-HD-NG-NG-HD-HD-HD-NI-NN-HD-HD-NI-HD-HD-NG (SEQ ID NO: 241) |
| 101304 (exon 4) | gtTAAAGGGGTTATTGTct (SEQ ID NO: 242) | NG-NI-NI-NI-NN-NN-NN-NN-NG-NG-NI-NG-NG-NN-NG (SEQ ID NO: 243) |

The TALEN pairs shown above were introduced into cells and showed cleavage activity. Pair 101291/101292 yielded a value of 0.8% indels as measured by the Cel-1 assay in K562 cells. TALEN pair 101301/101304 gave a value of 35.7% indel formation in CD34+ cells, and was found by the RT-PCR assay described above to induce an increase in gamma globin mRNA expression of about 2.31 fold.

ZFN pairs were also made to target the 'XL' portion of the BCL11A-XL splice variant. These proteins were tested in K562 cells and a representative data set is shown below in Table 1D. The 'XL' isoform of BCL11A contains 3 additional natural zinc fingers (fingers 4-6), thus the approach taken involved disrupting the BCL11A gene in this region to cause unfolding of potentially zinc fingers 4, 5, and/or 6 and combinations thereof (numbers 1 through 3 within the XL region). The ZFNs were also engineered to avoid cleavage of the related BCL11B gene sequence. One ZFN pair, 44888/44889, targeted the fourth zinc finger of BCL11A, while two pairs 44904/44905 and 44910/44911 targeted upstream of the fourth finger (number 1 within the XL, region) while the two other pairs, 44946/44947 and 44945/44944 targeted the fifth finger (number 2 within the XL region). These proteins were tested in K562 cells and a representative data set is shown below in Table 1D. Two of the ZFN pairs contained novel linker sequences between the ZFP DNA binding domain and the Fok1 nuclease domain. The 44904/44905 pair both contain the L7a linker sequence (see U.S. Patent Application No. 20090305419) and the 44946/44947 pair both contained the L8p linker sequence, both of which are shown below. See also U.S. Publication No. 20150064789.

```
L7a:  HTKIHLRGSQLVKSKSEAAAR   (SEQ ID NO: 244)
L8p:  HTKIHLRGSYAPMPPLALASP.  (SEQ ID NO: 245)
```

TABLE 1D

Activity of ZFN pairs specific for BCL11A XL

| ZFN pair | % indels, K562 |
|---|---|
| 44889/44888 | 35.14 |
| 44905/44904 | 25.45 |
| 44911/44910 | 36.43 |
| 44945/44944 | 24.03 |
| 44947/44946 | 34.22 |

The BCL11A XL pairs are then tested in CD34+ cells and are active. Measurement of the expression of gamma globin demonstrates that the modification of BCL11A XL results in an increase of gamma globin expression relative to alpha globin.

Additional pairs of KLF1-specific ZFNs were tested for activity in CD34+ cells, and these cells were analyzed for any change in gamma globin expression. A representative data set is shown below in Table 1E.

TABLE 1E

Activity of KLF-specific ZFN pairs

| Target | ZFN pair | % indels, CD34+ | Fold increase in gamma mRNA |
|---|---|---|---|
| KLF exon 1 | 36004/36021 | 44.4 | 2.2X |
| KLF exon 2 | 36071/36085 | 22.6 | 3.17X |

Figure 5:
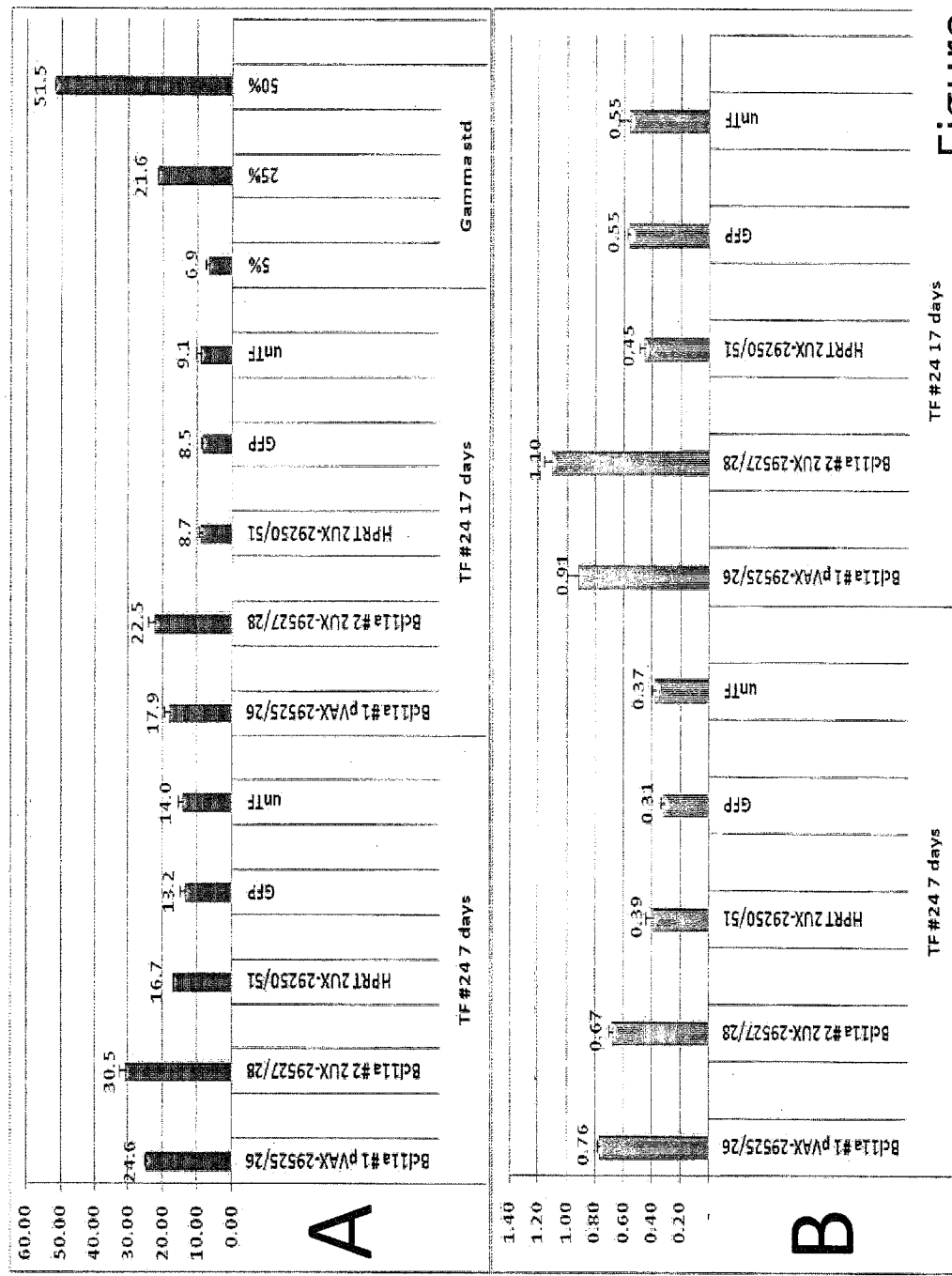
FIG. 5, panels A and B, depict the expression of either gamma globin compared to beta-globin (FIG. 5A) or gamma globin mRNA corrected with the 18s RNA standard (FIG. 5B) either 7 or 17 days following differentiation as analyzed by a Taqman® procedure. The percent of gamma globin mRNA compared to gamma+beta-globin mRNA is shown above each bar in FIG. 5A.

The ratios of mRNAs encoding γ globin and β globin following treatment of BCL11A- or KLF1 specific nucleases in HSCs were determined at various time points up to 17 days following ZFN introduction by Taqman analysis, and the beta-like globin mRNA levels were also normalized to the level of 18S rRNA. Gamma globin expression levels increased in those cells that had been treated with the BCL11A or KLF1 specific nucleases (FIG. 5). The analysis was done by standard Taqman analysis, following the protocol and using gene specific assays supplied by the manufacturer (Applied Biosystems).

The BCL11A ZFN-modified cells were also analyzed to determine the γ/β mRNA ratios as between cell populations in which one allele was modified by the ZFNs ("Bb"), cells in which both alleles were modified by the ZFNs ("knockout") and wild-type ("BB").

As shown in FIG. 6, the γ/β mRNA ratios are different between cells in which the BCL11A knockout has occurred at one allele only (Bb, bars 6-10 from the left) or where both alleles have been knocked out (knockout, rightmost 5 bars, bars 11-15 from the left), and both pools of cells differ from the wild type (BB, first 5 bars).

Example 7: Modification of the Regulatory Region of the Gamma Globin Gene

Figure 9:
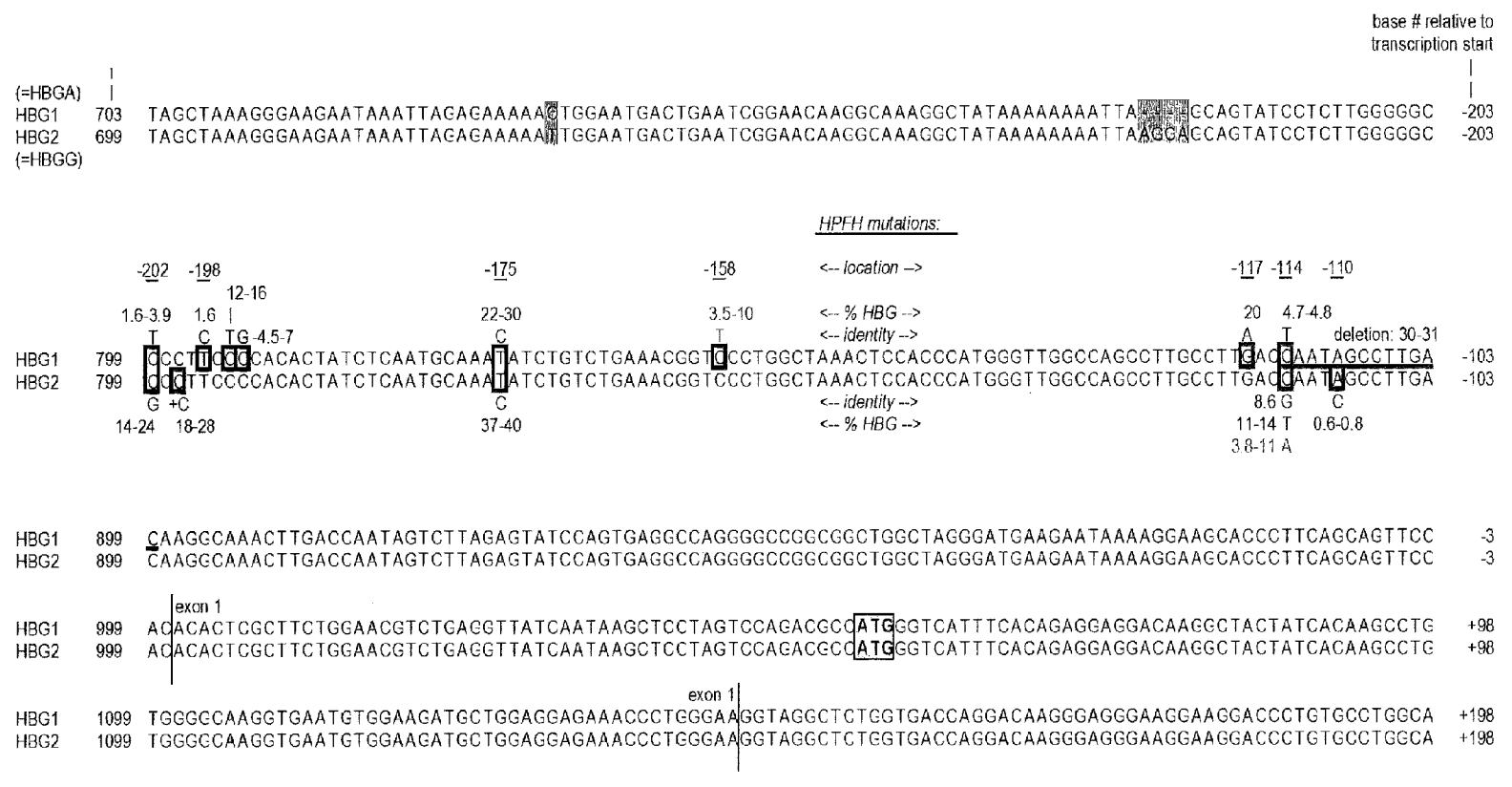

In another approach to increase the expression of gamma globin, mutations were made in the regulatory region of the gamma globin gene to mimic HPFH mutations (see FIG. 9). Shown below is the region from −202 to −102 relative to the ATG in the gamma globin gene. On this sequence are grey boxes indicating areas that have been shown to be associated with HPFH, and an underlined sequence that, when deleted, has also been associated with HPFH (see *A Syllabus of Thalassemia Mutations* (1997) by Titus H. J. Huisman, Marianne F. H. Carver, and Erol Baysal, published by The Sickle Cell Anemia Foundation in Augusta, Ga., USA. Copyright© 1997 by Titus H. J. Huisman):

−202

(SEQ ID NO: 132)

CCGTCCGCACACTATCTCAATGCAAATATGTCTCTGAAACGGTCCTGGCTAAACTCCACCCATGGGTT

GGCCTTGCCTTGACGAATAGCCTTGAC

−102

Nucleases were designed as described in Example 1 and shown in Table 1A to bind in the region of these HPFH associated mutations to induce mutations in the wild type region. The percent edited alleles detected (% NHEJ) in K562 cells by Cel I analysis (see Perez et al (2008), ibid) is shown below in Table 2. Additionally some pairs were tested in CD34+ cells as described above and analyzed by MiSeq sequencing as described above. For some pairs, cells were analyzed for any change in gamma globin expression. Table 2 below shows representative data sets:

TABLE 2

Editing by gamma globin specific ZFN pairs

| ZFN pair (location) | % NHEJ K562 | % NHEJ CD34+ | Fold increase in gamma mRNA |
|---|---|---|---|
| 34360/34363 (−175) | 39 | | |
| 34398/34400 (−175) | 54 | | |
| 31160/34365 (−175) | 53 | 45.22 | 1.63X |
| 34539/34574 (−110) | | 45.71 | 5.38X |
| 43865/43852 (−110) | | 56.13 | |

The first three pairs tested in this assay targeted the region around −175 in the gamma promoter region while the last two targeted the −110 region in the gamma globin promoter.

Figure 8:
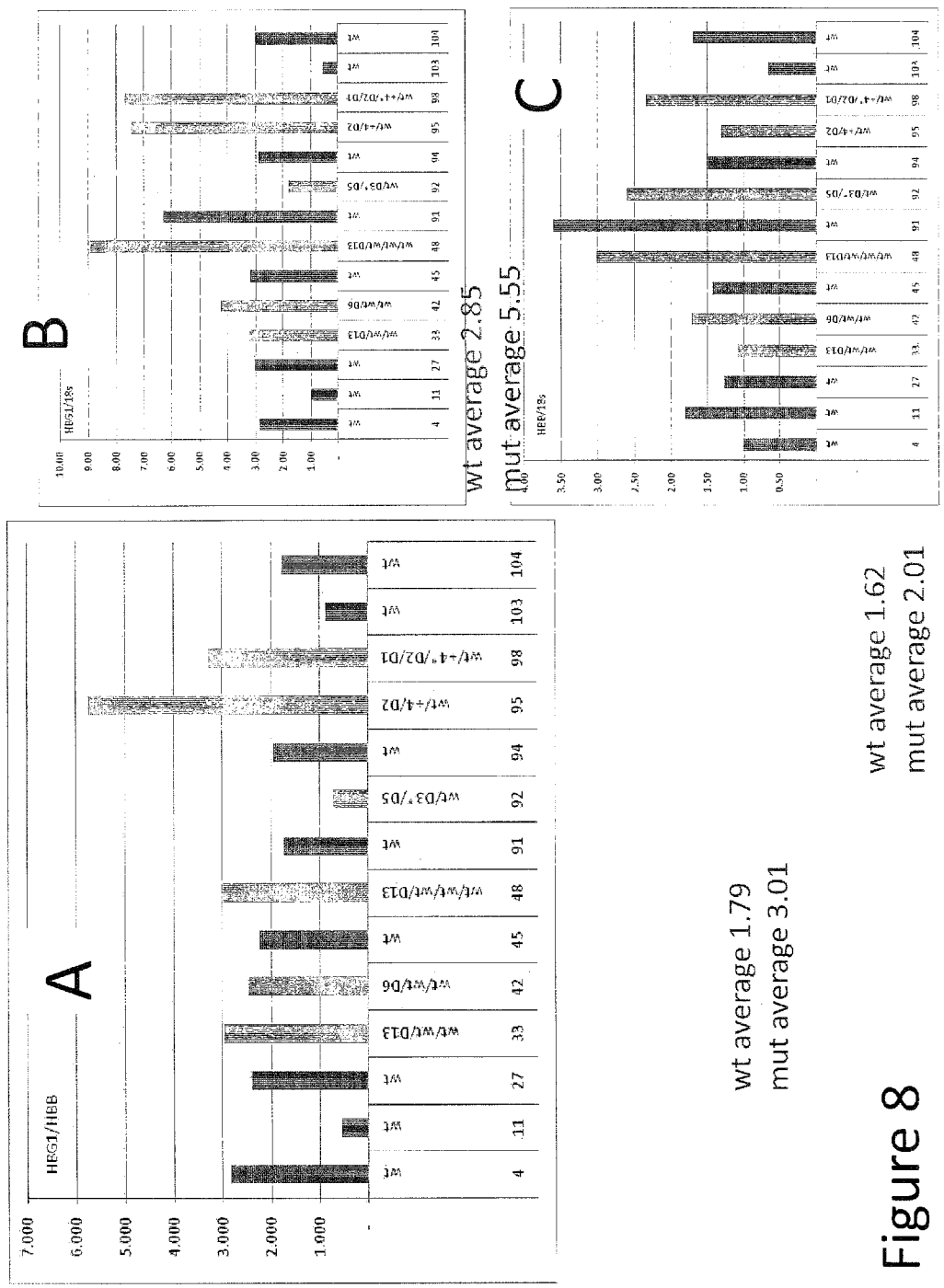
FIG. 8, panels A to C, depict the Taqman analysis of erythroid colonies derived from HSCs treated with ZFNs targeting the gamma-globin promoter followed by plating out on methylcellulose colonies. The colony numbers are indicated at the bottom of each bar as is the genotype.

The gamma promoter region in K562 cells that had been edited was sequenced to analyze the mutations created. The region was first PCR amplified and then the PCR products were sequenced and a number of different mutations were observed, including deletions and insertions (FIG. 8). In this experiment, 42% of the alleles were mutated, and 20% carried the 13 bp deletion from −114 through −102 associated with HPFH.

Two pairs of the ZFNs targeting the gamma globin promoter were also used to treat cells in combination with an oligonucleotide donor designed to recreate the most common mutations in subject with HPFH. The same protocol described above for use with the BTX device was followed with the addition of 3 μL of a 100 μM solution of the donor oligonucleotide. The sequence of the oligonucleotide donors is shown below. Typically, the forward oligonucleotide donor was used in these experiments, but the reverse donor worked as well:

HBG_d13 forward:
(124mer, SEQ ID NO: 246)
acactatctcaatgcaaatatctgtctgaaacggtccctggctaaactcc acccatgggttggccagccttgccttgacaaggcaaacttgaccaatagt cttagagtatccagtgaggccagg HBG_d13_reverse:
(124mer, SEQ ID NO: 247)
cctggcctcactggatactctaagactattggtcaagtttgccttgtcaa ggcaaggctggccaacccatgggtggagtttagccagggaccgtttcaga cagatatttgcattgagatagtgt For ZFN pair 34539/34574 in the presence of the donor, the mRNA production from the gamma globin gene increased 6.38 fold as compared to cells treated with a GFP vector while for the ZFN pair 31160/34365, gamma mRNA increased by 6.13 fold as compared to cells treated with a GFP vector.

The nuclease treated HSCs were plated on methylcellulose. After genotyping individual colonies by PCR sequencing, we measured the mRNA levels for gamma-globin, beta-globin and the 18s rRNA control for wild type and mutated colonies by RT-PCR. (FIG. 8). On average, the gamma globin promoter mutants had a higher ratio of gamma globin to beta globin message than wild type cells and correction by the 18s rRNA signal indicates that the increase in the gamma-globin/beta-globin ratio in the mutated colonies is caused by an increase in gamma-globin mRNA levels in these colonies rather than a reduction of beta-globin mRNA levels.

Example 8: TALE Nucleases Targeted to the Gamma Globin Promoter

TALE nucleases were also made to target the −200 region or −110 region (described above) of the gamma globin promoter region. The TALENs were constructed as described previously, using the canonical TALE code and the '+17' TALEN backbone (see co-owned U.S. Patent publication 20110301073).

TABLE 3

Gamma globin promoter specific TALENs

| SBS number | Sequence 5'->3' | RVD sequence (N->C) |
|---|---|---|
| 102314 | gtATCCTCTTGGGGGcc (SEQ ID NO: 133) | NI-NG-HD-HD-NG-HD-NG-NG-NN-NN-NN-NN-NK (SEQ ID NO: 134) |
| 102318 | atATTTGCATTGAGATAGTgt (SEQ ID NO: 135) | NI-NG-NG-NG-NN-HD-NI-NG-NG-NN-NI-NN-NI-NG-NI-NN-NG (SEQ ID NO: 136) |
| 102315 | gtATCCTCTTGGGGGCcc (SEQ ID NO: 254) | NI-NG-HD-HD-NG-HD-NG-NG-NN-NN-NN-NN-HD (SEQ ID NO: 137) |
| 102320 | atATTTGCATTGAGATAgt (SEQ ID NO: 255) | NI-NG-NG-NG-NN-HD-NI-NG-NG-NN-NI-NN-NI-NG-NI (SEQ ID NO: 258) |
| 102316 | gtATCCTCTTGGGGGCCcc (SEQ ID NO: 256) | NI-NG-HD-HD-NG-HD-NG-NG-NN-NN-NN-NN-HD-HD (SEQ ID NO: 138) |
| 102321 | atATTTGCATTGAGATAg (SEQ ID NO: 257) | NI-NG-NG-NG-NN-HD-NI-NG-NG-NN-NI-NN-NI-NG (SEQ ID NO: 139) |

TABLE 3-continued

Gamma globin promoter specific TALENs

| SBS number | Sequence 5'->3' | RVD sequence (N->C) |
|---|---|---|
| 102566 (-110) | gtTGGCCAGCCTTGCCTTG ac (SEQ ID NO: 248) | NG-NN-NN-HD-HD-NI-NN-HD-HD-NG-NG-NN-HD-HD-NG-NG-NK (SEQ ID NO: 249) |
| 102568 (-110) | ttGGTCAAGTTTGCCTTGT ca (SEQ ID NO: 250) | NN-NN-NG-HD-NI-NI-NN-NG-NG-NG-NN-HD-HD-NG-NG-NN-NG (SEQ ID NO: 251) |

The TALENs were then used in pairs to test cleavage in K562 cells and assayed by the Cel 1 assay as described previously and the results of the pairs are shown below in Table 4. In addition, TALEN pair 102566/102568 was tested against CD34+ cells and found to have 51.39% NHEJ as measured by MiSeq analysis.

Two pairs of the TALENs were also tested for gamma globin mRNA expression as measured by the ratio of gamma globin to alpha globin mRNAs. Pair 102566/102568 was found to increase gamma globin expression by 6.25 fold as compared to CD34+ cells treated with a GFP vector, and pair 102318/102314 increased gamma globin by 2.14 fold as compared to CD34+ cells treated with a GFP vector. Pair 102566/102568 was also tested with the donor oligo described above and the resulting cells were found to have an increase in gamma globin expression of 9.13 fold as compared to CD34+ cells treated with a GFP vector.

TABLE 4

Editing of the gamma globin promoter region with TALENs

| TALEN pair | % NHEJ '+17' |
|---|---|
| 102314:102318 | 41.6 |
| 102315:102320 | 47.9 |
| 102316:102321 | 46.6 |

Example 9: Gamma Globin Editing in CD34+ Stem Cells

The nucleases specific for the gamma globin promoter region are then used in patient derived CD34+ cells. The cells are treated with the nucleases and then analyzed for successful editing by Cel 1 analysis. The cells are further analyzed to examine the ratios of gamma globin versus beta globin and demonstrate an increased expression of gamma globin. The representative data found for increased gamma globin expression is located in the experimental sections for the different approaches above.

Example 10: Edited CD34+ Engraftment in Mice

Nuclease-treated CD34+ cells (human stem cell progenitor HSPCs) retained the ability to engraft NOD/SCID/IL2rgamma(null) mice and give rise to polyclonal multi-lineage progeny in which genes involved in the regulation of gamma globin are permanently disrupted (see Holt et al, (2010) Nat Biotechnol. August; 28(8):839-47). Similarly, CD34+ or HSPCs edited at the beta globin locus where a mutation is corrected, or a donor beta globin gene is inserted into a safe harbor locus, or are treated with nucleases to alter the expression of gamma globin are able to engraft and give rise to multi-lineage progeny carrying the desired genome editing. The demonstration that a minority of edited HSPCs can populate an animal with edited progeny supports the use of nuclease-modified autologous hematopoietic stem cells as a clinical approach to treating hemoglobinopathies.

All patents, patent applications and publications mentioned herein are hereby incorporated by reference in their entirety.

Although disclosure has been provided in some detail by way of illustration and example for the purposes of clarity of understanding, it will be apparent to those skilled in the art that various changes and modifications can be practiced without departing from the spirit or scope of the disclosure. Accordingly, the foregoing descriptions and examples should not be construed as limiting.

What is claimed is:

1. A zinc finger protein comprising five or six zinc finger domains designated and ordered F1 to F5 or F1 to F6 from N-terminus to C-terminus, wherein F1 to F5 or F1 to F6 comprises any one of the following recognition helix regions:

(i) F1: DRSNLSR (SEQ ID NO:9);
  F2: LRQNLIM (SEQ ID NO:161);
  F3: TSANLTV (SEQ ID NO:162);
  F4: RSDHLSR (SEQ ID NO:94);
  F5: QSGNLAR (SEQ ID NO:39); and
  F6: QRNDRKS (SEQ ID NO:163), wherein the zinc finger protein binds to a target site as set forth in SEQ ID NO:160;

(ii) F1: DRSNLSR (SEQ ID NO:9);
  F2: LRQNLIM (SEQ ID NO:161);
  F3: LQSQLNR (SEQ ID NO:164);
  F4: RSDHLSR (SEQ ID NO:94);
  F5: QSGNLAR (SEQ ID NO:39); and
  F6: QRNDRKS (SEQ ID NO:163), wherein the zinc finger protein binds to a target site as set forth in SEQ ID NO:160;

(iii) F1: DRANLSR (SEQ ID NO:165);
  F2: LRQNLIM (SEQ ID NO:161);
  F3: LQSQLNR (SEQ ID NO:164);
  F4: RSDHLSR (SEQ ID NO:94);
  F5: QSGNLAR (SEQ ID NO:39); and
  F6: QRNDRKS (SEQ ID NO:163), wherein the zinc finger protein binds to a target site as set forth in SEQ ID NO:160;

(iv) F1: DRSNLSR (SEQ ID NO:9);
  F2: TSSNRNH (SEQ ID NO:166);
  F3: HSGNLTK (SEQ ID NO:167);
  F4: RSDHLSR (SEQ ID NO:94);
  F5: QSGNLAR (SEQ ID NO:39); and
  F6: QKVDLSR (SEQ ID NO:168), wherein the zinc finger protein binds to a target site as set forth in SEQ ID NO:160;

(v) F1: DRSNLSR (SEQ ID NO:9);
  F2: TSSNRNH (SEQ ID NO:166);
  F3: QANNLKV (SEQ ID NO:169);
  F4: RSDHLSR (SEQ ID NO:94);
  F5: QSGNLAR (SEQ ID NO:39); and
  F6: QKVDLSR (SEQ ID NO:168), wherein the zinc finger protein binds to a target site as set forth in SEQ ID NO:160;

(vi) F1: RSDHLSA (SEQ ID NO:59);
  F2: DRSALAR (SEQ ID NO:30);
  F3: RSDSLSR (SEQ ID NO:171);
  F4: DRSVRTK (SEQ ID NO:172);
  F5: RSDHLSA (SEQ ID NO:59); and
  F6: QRSNLKV (SEQ ID NO:173), wherein the zinc finger protein binds to a target site as set forth in SEQ ID NO:170;

(vii) F1: RSDHLTQ (SEQ ID NO:35);
  F2: DRSALAR (SEQ ID NO:30);
  F3: RSDSLSR (SEQ ID NO:171);
  F4: DRSVRTK (SEQ ID NO:172);
  F5: RSDHLSA (SEQ ID NO:59); and
  F6: QRSNLKV (SEQ ID NO:173), wherein the zinc finger protein binds to a target site as set forth in SEQ ID NO:170;

(viii) F1: RSDHLTT (SEQ ID NO:174);
  F2: DRSALAR (SEQ ID NO:30);
  F3: RSDSLSR (SEQ ID NO:171);
  F4: DRSVRTK (SEQ ID NO:172);
  F5: RSDHLSA (SEQ ID NO:59); and
  F6: QRSNLKV (SEQ ID NO:173), wherein the zinc finger protein binds to a target site as set forth in SEQ ID NO:170;

(ix) F1: RSDHLSA (SEQ ID NO:59);
  F2: WATARDR (SEQ ID NO:175);
  F3: RSDSLSR (SEQ ID NO:171);
  F4: HTKSLSR (SEQ ID NO:176);
  F5: RSDHLSA (SEQ ID NO:59);
  F6: QRSNLKV (SEQ ID NO:173); wherein the zinc finger protein binds to a target site as set forth in SEQ ID NO:170;

(x) F1: RSAHLTQ (SEQ ID NO:177);
  F2: DRSVLRR (SEQ ID NO:178)
  F3: RSDSLSR (SEQ ID NO:171);
  F4: DRSVRTK (SEQ ID NO:172);
  F5: RSDHLSA (SEQ ID NO:59); and
  F6: QRSNLKV (SEQ ID NO:173), wherein the zinc finger protein binds to a target site as set forth in SEQ ID NO:170;

(xi) F1: RSDVLSE (SEQ ID NO:57);
F2: RNQHRKT (SEQ ID NO:58);
F3: RSDHLSA (SEQ ID NO:59);
F4: RSANLTR (SEQ ID NO:60;
F5: RSDVLSN (SEQ ID NO:61); and
F6: DRSTRIT (SEQ ID NO:62), wherein the zinc finger protein binds to a target site as set forth in SEQ ID NO:56;

(xii) F1: DRSNLSR (SEQ ID NO:9);
F2: HRQHLVT (SEQ ID NO:64);
F3: DRSNLTR (SEQ ID NO:65);
F4: QSGDLTR (SEQ ID NO:13); and
F5: HRSSLLN (SEQ ID NO:66), wherein the zinc finger protein binds to a target site as set forth in SEQ ID NO:63;

(xiii) F1: QSGHLSR (SEQ ID NO:32);
F2: RSDHLST (SEQ ID NO:67);
F3: RSADLSR (SEQ ID NO:68);
F4: RSDNLSQ (SEQ ID NO:69); and
F5: ASNDRKK (SEQ ID NO:70), wherein the zinc finger protein binds to a target site as shown in SEQ ID NO:66; or (xiv) F1: RSDNLSA (SEQ ID NO:72);
F2: RNNDRKT (SEQ ID NO:73);
F3: DRSDLSR (SEQ ID NO:29);
F4: TSSNRTK (SEQ ID NO:74);
F5: QSGNLAR (SEQ ID NO:39); and
F6: QSGDLTR (SEQ ID NO:13), wherein the zinc finger protein binds to a target site as set forth in SEQ ID NO:71.

2. A fusion protein comprising the zinc finger protein of claim 1 and a cleavage domain or cleavage half-domain.

3. An isolated polynucleotide encoding the zinc finger proteins of claim 1.

4. An isolated cell comprising the zinc finger proteins of claim 1.

5. An isolated cell comprising the polynucleotides of claim 3.

6. The cell of claim 5, wherein the cell is a red blood cell precursor cell.

7. The cell of claim 5, wherein the cell is a red blood cell (RBC).

8. The cell of claim 6, wherein the precursor cell is a CD34+ hematopoietic stem cell.

9. A kit comprising the protein of claim 1.

10. A kit comprising the polynucleotide of claim 3.

11. An isolated cell comprising the fusion protein of claim 2.

* * * * *

SEQUENCE LISTING

```
<160> NUMBER OF SEQ ID NOS: 258

<210> SEQ ID NO 1
<211> LENGTH: 102
<212> TYPE: DNA
<213> ORGANISM: Homo sapiens

<400> SEQUENCE: 1
cagacaccat ggtgcacctg actcctgtgg agaagtctgc cgttactgcc ctgtggggca      60
aggtgaacgt ggatgaagtt ggtggtgagg ccctgggcag gt                        102

<210> SEQ ID NO 2
<211> LENGTH: 102
<212> TYPE: DNA
<213> ORGANISM: Homo sapiens
```

```
<400> SEQUENCE: 2
cagacaccat ggtgcacctg actcctgagg agaagtctgc cgttactgcc ctgtggggca    60
aggtgaacgt ggatgaagtt ggtggtgagg ccctgggcag gt                      102

<210> SEQ ID NO 3
<211> LENGTH: 102
<212> TYPE: DNA
<213> ORGANISM: Homo sapiens

<400> SEQUENCE: 3
cagacaccat ggtgcatctg actcctgagg agaagactgc tgtcaatgcc ctgtggggca    60
aagtgaacgt ggatgcagtt ggtggtgagg ccctgggcag gt                      102

<210> SEQ ID NO 4
<211> LENGTH: 101
<212> TYPE: DNA
<213> ORGANISM: Homo sapiens

<400> SEQUENCE: 4
ctgacactgt agtgcatttc actgctgaca agaaggctgc tgccaccagc ctgtgaagca    60
aggttaaggt gagaaggctg gaggtgagat tctgggcagg t                       101

<210> SEQ ID NO 5
<211> LENGTH: 102
<212> TYPE: DNA
<213> ORGANISM: Homo sapiens

<400> SEQUENCE: 5
ctggcatcat ggtgcatttt actgctgagg agaaggctgc cgtcactagc ctgtggagca    60
agatgaatgt ggaagaggct ggaggtgaag ccttgggcag gt                      102

<210> SEQ ID NO 6
<211> LENGTH: 102
<212> TYPE: DNA
<213> ORGANISM: Homo sapiens

<400> SEQUENCE: 6
cagacgccat gggtcatttc acagaggagg acaaggctac tatcacaagc ctgtggggca    60
aggtgaatgt ggaagatgct ggaggagaaa ccctgggaag gt                      102

<210> SEQ ID NO 7
<211> LENGTH: 102
<212> TYPE: DNA
<213> ORGANISM: Homo sapiens

<400> SEQUENCE: 7
cagacgccat gggtcatttc acagaggagg acaaggctac tatcacaagc ctgtggggca    60
aggtgaatgt ggaagatgct ggaggagaaa ccctgggaag gt                      102

<210> SEQ ID NO 8
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 8
gggcagtaac ggcagacttc tcctcagg                                      28
```

```
<210> SEQ ID NO 9
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Asp Arg Ser Asn Leu Ser Arg
1               5

<210> SEQ ID NO 10
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Gln Ser Ser Asp Leu Arg Arg
1               5

<210> SEQ ID NO 11
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Arg Ser Asp Thr Leu Ser Ala
1               5

<210> SEQ ID NO 12
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Gln Ser Gly Ala Leu Ala Arg
1               5

<210> SEQ ID NO 13
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13

Gln Ser Gly Asp Leu Thr Arg
1               5

<210> SEQ ID NO 14
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide
```

```
<400> SEQUENCE: 14
tggggcaagg tgaacgtgga tgaagttg                                        28

<210> SEQ ID NO 15
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

Gln Ser Ala His Arg Lys Asn
1               5

<210> SEQ ID NO 16
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

Leu Lys His His Leu Thr Asp
1               5

<210> SEQ ID NO 17
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17

Gln Arg Ser Asn Leu Val Arg
1               5

<210> SEQ ID NO 18
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18

Thr Ser Gly His Leu Ser Arg
1               5

<210> SEQ ID NO 19
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 19

Gln Ser Asn His Leu Thr Glu
1               5

<210> SEQ ID NO 20
<211> LENGTH: 7
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 20

Arg Ser His His Leu Lys Ala
1               5

<210> SEQ ID NO 21
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 21
agagtcaggt gcaccatggt gtctgttt                                            28

<210> SEQ ID NO 22
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 22

Thr Asn Gln Asn Arg Ile Thr
1               5

<210> SEQ ID NO 23
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 23

Asp Arg Ser Asn Arg Thr Thr
1               5

<210> SEQ ID NO 24
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 24

Arg Asn Ala Ser Arg Thr Arg
1               5

<210> SEQ ID NO 25
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 25

Arg Ser Asp Asn Leu Ser Glu
1               5
```

```
<210> SEQ ID NO 26
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 26

Arg Ser Gln His Arg Lys Thr
1               5

<210> SEQ ID NO 27
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 27
gtggagaagt ctgccgttac tgccctgt                                        28

<210> SEQ ID NO 28
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 28

Thr Ser Gly Ser Leu Ser Arg
1               5

<210> SEQ ID NO 29
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 29

Asp Arg Ser Asp Leu Ser Arg
1               5

<210> SEQ ID NO 30
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 30

Asp Arg Ser Ala Leu Ala Arg
1               5

<210> SEQ ID NO 31
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 31
```

Gln Ser Ser Asn Leu Ala Arg
1               5

<210> SEQ ID NO 32
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 32

Gln Ser Gly His Leu Ser Arg
1               5

<210> SEQ ID NO 33
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 33
acaggagtca ggtgcaccat ggtgtctg                                            28

<210> SEQ ID NO 34
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 34

Asp Gln Ser Asn Leu Arg Ala
1               5

<210> SEQ ID NO 35
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 35

Arg Ser Asp His Leu Thr Gln
1               5

<210> SEQ ID NO 36
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 36
gagaagtctg ccgttactgc cctgtggg                                            28

<210> SEQ ID NO 37
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 37

Ala Arg Ser Thr Arg Thr Asn
1               5

<210> SEQ ID NO 38
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 38

Asp Arg Ser Ala Arg Thr Arg
1               5

<210> SEQ ID NO 39
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 39

Gln Ser Gly Asn Leu Ala Arg
1               5

<210> SEQ ID NO 40
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 40
taacggcaga cttctccaca ggagtcag                                      28

<210> SEQ ID NO 41
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 41

Ser Ser Ser Asp Arg Lys Lys
1               5

<210> SEQ ID NO 42
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 42

Gln Ser Ala Asp Arg Thr Lys
1               5

<210> SEQ ID NO 43
<211> LENGTH: 28
<212> TYPE: DNA

```
<213> ORGANISM: Artificial Sequence
<220> FEATURE:
<223> OTHER INFORMATION: Description of Artificial Sequence: Synthetic
      oligonucleotide

<400> SEQUENCE: 43
gccctgtggg gcaaggtgaa cgtggatg                                           28

<210> SEQ ID NO 44
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 44

Leu Arg His His Leu Thr Arg
1               5

<210> SEQ ID NO 45
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 45

Gln Ser Gly Asn Leu His Val
1               5

<210> SEQ ID NO 46
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 46

Arg Ser Ala His Leu Ser Arg
1               5

<210> SEQ ID NO 47
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 47

Arg Ser Asp Val Leu Ser Thr
1               5

<210> SEQ ID NO 48
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 48

Arg Lys Gln Asp Leu Arg Thr
1               5
```

```
<210> SEQ ID NO 49
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 49

Met Ser His His Leu Arg Asp
1               5

<210> SEQ ID NO 50
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 50
cacagggcag taacggcaga cttctcct                                         28

<210> SEQ ID NO 51
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 51

Asp Arg Ser His Leu Thr Arg
1               5

<210> SEQ ID NO 52
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 52

Arg Ser Asp Asn Leu Arg Glu
1               5

<210> SEQ ID NO 53
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 53
ggcaaggtga acgtggatga agttggtg                                         28

<210> SEQ ID NO 54
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 54
```

```
Gln Ser Gly His Leu Ala Arg
1               5

<210> SEQ ID NO 55
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 55

Val Ser His His Leu Arg Asp
1               5

<210> SEQ ID NO 56
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 56
atcccatgga gaggtggctg ggaaggac                                        28

<210> SEQ ID NO 57
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 57

Arg Ser Asp Val Leu Ser Glu
1               5

<210> SEQ ID NO 58
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 58

Arg Asn Gln His Arg Lys Thr
1               5

<210> SEQ ID NO 59
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 59

Arg Ser Asp His Leu Ser Ala
1               5

<210> SEQ ID NO 60
<211> LENGTH: 7
<212> TYPE: PRT
<213> ORGANISM: Artificial Sequence
<220> FEATURE:
<223> OTHER INFORMATION: Description of Artificial Sequence: Synthetic
``` peptide

<400> SEQUENCE: 60

Arg Ser Ala Asn Leu Thr Arg
1               5

<210> SEQ ID NO 61
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 61

Arg Ser Asp Val Leu Ser Asn
1               5

<210> SEQ ID NO 62
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 62

Asp Arg Ser Thr Arg Ile Thr
1               5

<210> SEQ ID NO 63
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 63
atattgcaga caataacccc tttaacct                                        28

<210> SEQ ID NO 64
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 64

His Arg Gln His Leu Val Thr
1               5

<210> SEQ ID NO 65
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 65

Asp Arg Ser Asn Leu Thr Arg
1               5

<210> SEQ ID NO 66
<211> LENGTH: 7

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 66

His Arg Ser Ser Leu Leu Asn
1               5

<210> SEQ ID NO 67
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 67

Arg Ser Asp His Leu Ser Thr
1               5

<210> SEQ ID NO 68
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 68

Arg Ser Ala Asp Leu Ser Arg
1               5

<210> SEQ ID NO 69
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 69

Arg Ser Asp Asn Leu Ser Gln
1               5

<210> SEQ ID NO 70
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 70

Ala Ser Asn Asp Arg Lys Lys
1               5

<210> SEQ ID NO 71
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 71
gtgcagaata tgccccgcag ggtatttg                                        28
```

```
<210> SEQ ID NO 72
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 72

Arg Ser Asp Asn Leu Ser Ala
1               5

<210> SEQ ID NO 73
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 73

Arg Asn Asn Asp Arg Lys Thr
1               5

<210> SEQ ID NO 74
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 74

Thr Ser Ser Asn Arg Thr Lys
1               5

<210> SEQ ID NO 75
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 75
gggaaggggc ccagggcggt cagtgtgc                                        28

<210> SEQ ID NO 76
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 76

Asp Arg Ser His Leu Ala Arg
1               5

<210> SEQ ID NO 77
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 77

Ala Ser Lys Thr Arg Lys Asn
1               5

<210> SEQ ID NO 78
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 78

Arg Ser Asp His Leu Ser Glu
1               5

<210> SEQ ID NO 79
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 79
acacacagga tgacttcctc aaggtggg                                          28

<210> SEQ ID NO 80
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 80

Thr Ser Gly Asn Leu Thr Arg
1               5

<210> SEQ ID NO 81
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 81

Gln Ser Ala Ser Arg Lys Asn
1               5

<210> SEQ ID NO 82
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 82
cgccaccggg ctccgggccc gagaagtt                                          28

<210> SEQ ID NO 83
<211> LENGTH: 7
<212> TYPE: PRT
<213> ORGANISM: Artificial Sequence
<220> FEATURE:
```

<223> OTHER INFORMATION: Description of Artificial Sequence: Synthetic
      peptide

<400> SEQUENCE: 83

Asp Ser Ser Asp Arg Lys Lys
1               5

<210> SEQ ID NO 84
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 84

Arg Ser Asp Thr Leu Ser Glu
1               5

<210> SEQ ID NO 85
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 85
ccccagacct gcgctctggc gcccagcg                                          28

<210> SEQ ID NO 86
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 86

Arg Ser Asp Ser Leu Leu Arg
1               5

<210> SEQ ID NO 87
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 87

Arg Leu Asp Trp Leu Pro Val
1               5

<210> SEQ ID NO 88
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 88

Gln Ser Ser Asp Leu Ser Arg
1               5

<210> SEQ ID NO 89

```
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 89

Ala Ala Ser Asn Arg Ser Lys
1               5

<210> SEQ ID NO 90
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 90
ggctcggggg ccggggctgg agccaggg                                      28

<210> SEQ ID NO 91
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 91

Gln Ser Ser His Leu Thr Arg
1               5

<210> SEQ ID NO 92
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 92

Gln Ser Ser Asp Leu Thr Arg
1               5

<210> SEQ ID NO 93
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 93

His Ser Arg Thr Arg Thr Lys
1               5

<210> SEQ ID NO 94
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 94

Arg Ser Asp His Leu Ser Arg
```

```
1               5
```

<210> SEQ ID NO 95
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 95

```
Asp Arg Ser Ala Arg Asn Ser
1               5
```

<210> SEQ ID NO 96
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 96

```
aaggcgctgg cgctgcaacc ggtgtacc                                    28
```

<210> SEQ ID NO 97
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 97

```
Gln Ser His Asn Arg Thr Lys
1               5
```

<210> SEQ ID NO 98
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 98

```
ttgcagcgcc agcgccttgg gctcgggg                                    28
```

<210> SEQ ID NO 99
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 99

```
Arg Ser Asp His Leu Ser Gln
1               5
```

<210> SEQ ID NO 100
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 100

His Arg Ser Ser Leu Gly Asp
1               5

<210> SEQ ID NO 101
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 101

Arg Ser Asp Asp Leu Thr Arg
1               5

<210> SEQ ID NO 102
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 102

Gln Arg Ser Thr Leu Ser Ser
1               5

<210> SEQ ID NO 103
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 103

Arg Ser Ala Asp Leu Thr Arg
1               5

<210> SEQ ID NO 104
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 104
cggtgtaccc ggggcccggc gccggctc                                        28

<210> SEQ ID NO 105
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 105

Arg Ser Thr His Leu Val Arg
1               5

<210> SEQ ID NO 106
<211> LENGTH: 7
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 106

Arg Ser Asp Ser Leu Ser Thr
1               5

<210> SEQ ID NO 107
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 107

Asp Ser Ser Asp Arg Thr Lys
1               5

<210> SEQ ID NO 108
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 108

Arg Ser Ala Ala Leu Ala Arg
1               5

<210> SEQ ID NO 109
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 109
ttgcattgag atagtgtggg gaaggggc                                            28

<210> SEQ ID NO 110
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 110

Arg Ser Asp His Leu Ser Val
1               5

<210> SEQ ID NO 111
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 111

Arg Ser Asp Val Arg Lys Thr
1               5
```

<210> SEQ ID NO 112
<211> LENGTH: 7
<212> TYPE: PRT
<213> ORGANISM: Artificial Sequence
<220> FEATURE:
<223> OTHER INFORMATION: Description of Artificial Sequence: Synthetic
    peptide

<400> SEQUENCE: 112

Arg Ser Asp Tyr Leu Ser Lys
1               5

<210> SEQ ID NO 113
<211> LENGTH: 7
<212> TYPE: PRT
<213> ORGANISM: Artificial Sequence
<220> FEATURE:
<223> OTHER INFORMATION: Description of Artificial Sequence: Synthetic
    peptide

<400> SEQUENCE: 113

Thr Ser Ser Val Arg Thr Thr
1               5

<210> SEQ ID NO 114
<211> LENGTH: 7
<212> TYPE: PRT
<213> ORGANISM: Artificial Sequence
<220> FEATURE:
<223> OTHER INFORMATION: Description of Artificial Sequence: Synthetic
    peptide

<400> SEQUENCE: 114

Arg Pro Tyr Thr Leu Arg Leu
1               5

<210> SEQ ID NO 115
<211> LENGTH: 7
<212> TYPE: PRT
<213> ORGANISM: Artificial Sequence
<220> FEATURE:
<223> OTHER INFORMATION: Description of Artificial Sequence: Synthetic
    peptide

<400> SEQUENCE: 115

Gln Asn Ala Thr Arg Thr Lys
1               5

<210> SEQ ID NO 116
<211> LENGTH: 28
<212> TYPE: DNA
<213> ORGANISM: Artificial Sequence
<220> FEATURE:
<223> OTHER INFORMATION: Description of Artificial Sequence: Synthetic
    oligonucleotide

<400> SEQUENCE: 116
atctgtctga aacggtccct ggctaaac                                        28

<210> SEQ ID NO 117
<211> LENGTH: 7
<212> TYPE: PRT
<213> ORGANISM: Artificial Sequence
<220> FEATURE:
<223> OTHER INFORMATION: Description of Artificial Sequence: Synthetic
    peptide

<400> SEQUENCE: 117

Arg Arg Asp Ile Leu His Gln
1               5

<210> SEQ ID NO 118
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 118

Leu Ala Tyr Asp Arg Arg Lys
1               5

<210> SEQ ID NO 119
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 119
tttgcattga gatagtgtgg ggaagggg                                         28

<210> SEQ ID NO 120
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 120

Gln Ser Cys Ala Arg Asn Val
1               5

<210> SEQ ID NO 121
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 121

Arg Ser Asp Asn Leu Ala Arg
1               5

<210> SEQ ID NO 122
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 122

His Arg Asn Thr Leu Leu Gly
1               5

<210> SEQ ID NO 123
<211> LENGTH: 7
<212> TYPE: PRT
<213> ORGANISM: Artificial Sequence
<220> FEATURE:
<223> OTHER INFORMATION: Description of Artificial Sequence: Synthetic peptide

<400> SEQUENCE: 123

Met Arg Asn Arg Leu Asn Arg
1               5

<210> SEQ ID NO 124
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 124
ctgtctgaaa cggtccctgg ctaaactc                                          28

<210> SEQ ID NO 125
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 125

Arg Arg Asp Ala Leu Leu Met
1               5

<210> SEQ ID NO 126
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 126

Gln Asn Ala His Arg Lys Thr
1               5

<210> SEQ ID NO 127
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 127
tatttgcatt gagatagtgt ggggaagg                                          28

<210> SEQ ID NO 128
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 128

Leu Gln His His Leu Thr Asp
1               5

<210> SEQ ID NO 129
<211> LENGTH: 7
<212> TYPE: PRT

```
<213> ORGANISM: Artificial Sequence
<220> FEATURE:
<223> OTHER INFORMATION: Description of Artificial Sequence: Synthetic
      peptide

<400> SEQUENCE: 129

Thr Ser Thr His Leu His Ile
1               5

<210> SEQ ID NO 130
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 130

His Lys Trp Val Leu Arg Gln
1               5

<210> SEQ ID NO 131
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 131

Arg Arg Asp Ala Leu Leu Met
1               5

<210> SEQ ID NO 132
<211> LENGTH: 97
<212> TYPE: DNA
<213> ORGANISM: Homo sapiens

<400> SEQUENCE: 132
cccttcccca cactatctca atgcaaatat gtctctgaaa cggtccctgg ctaaactcca    60
cccatgggtt ggccttgcct tgaccaatag ccttgac                            97

<210> SEQ ID NO 133
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 133
gtatcctctt gggggcc                                                  17

<210> SEQ ID NO 134
<211> LENGTH: 13
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 134
atcctcttrr rrg                                                      13

<210> SEQ ID NO 135
<211> LENGTH: 21
```

```
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 135
atatttgcat tgagatagtg t                                              21

<210> SEQ ID NO 136
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 136
atttrcattr aratart                                                   17

<210> SEQ ID NO 137
<211> LENGTH: 14
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 137
atcctcttrr rrrc                                                      14

<210> SEQ ID NO 138
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 138
atcctcttrr rrrcc                                                     15

<210> SEQ ID NO 139
<211> LENGTH: 14
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 139
atttrcattr arat                                                      14

<210> SEQ ID NO 140
<211> LENGTH: 51
<212> TYPE: DNA
<213> ORGANISM: Homo sapiens

<400> SEQUENCE: 140
ggccagcctt gccttgacca atagccttga caaggcaaac ttgaccaata g             51

<210> SEQ ID NO 141
<211> LENGTH: 50
<212> TYPE: DNA
<213> ORGANISM: Homo sapiens

<400> SEQUENCE: 141
```

-continued ggccagcctt gccttgacca tagccttgac aaggcaaact tgaccaatag     50

<210> SEQ ID NO 142
<211> LENGTH: 47
<212> TYPE: DNA
<213> ORGANISM: Homo sapiens

<400> SEQUENCE: 142
ggccagcctt gccttaatag ccttgacaag gcaaacttga ccaatag     47

<210> SEQ ID NO 143
<211> LENGTH: 45
<212> TYPE: DNA
<213> ORGANISM: Homo sapiens

<400> SEQUENCE: 143
ggccagcctt gccttgaccc ttgacaaggc aaacttgacc aatag     45

<210> SEQ ID NO 144
<211> LENGTH: 45
<212> TYPE: DNA
<213> ORGANISM: Homo sapiens

<400> SEQUENCE: 144
ggccagcctt gccttgacca atagcaaggc aaacttgacc aatag     45

<210> SEQ ID NO 145
<211> LENGTH: 38
<212> TYPE: DNA
<213> ORGANISM: Homo sapiens

<400> SEQUENCE: 145
ggccagcctt gccttgacaa ggcaaacttg accaatag     38

<210> SEQ ID NO 146
<211> LENGTH: 51
<212> TYPE: DNA
<213> ORGANISM: Homo sapiens

<400> SEQUENCE: 146
ggccagcctt gccttgacca aatagccttg acaaggcaaa cttgaccaat a     51

<210> SEQ ID NO 147
<211> LENGTH: 51
<212> TYPE: DNA
<213> ORGANISM: Homo sapiens

<400> SEQUENCE: 147
ggccagcctt gccttgacca atagcagcct tgacaaggca aacttgacca a     51

<210> SEQ ID NO 148
<211> LENGTH: 51
<212> TYPE: DNA
<213> ORGANISM: Homo sapiens

<400> SEQUENCE: 148
ggccagcctt gccttgacca atagaatagc cttgacaagg caaacttgac c     51

<210> SEQ ID NO 149
<211> LENGTH: 196
<212> TYPE: DNA
<213> ORGANISM: Homo sapiens

<400> SEQUENCE: 149

```
tagctaaagg gaagaataaa ttagagaaaa actggaatga ctgaatcgga acaaggcaaa    60
ggctataaaa aaaattagca gtatcctctt gggggcccct tccccacact atctcaatgc   120
aaatatctgt ctgaaacggt ccctggctaa actccaccca tgggttggcc agccttgcct   180
tgaccaatag ccttga                                                   196
```

<210> SEQ ID NO 150
<211> LENGTH: 200
<212> TYPE: DNA
<213> ORGANISM: Homo sapiens

<400> SEQUENCE: 150

```
tagctaaagg gaagaataaa ttagagaaaa attggaatga ctgaatcgga acaaggcaaa    60
ggctataaaa aaaattaagc agcagtatcc tcttgggggc cccttcccca cactatctca   120
atgcaaatat ctgtctgaaa cggtccctgg ctaaactcca cccatgggtt ggccagcctt   180
gccttgacca atagccttga                                               200
```

<210> SEQ ID NO 151
<211> LENGTH: 300
<212> TYPE: DNA
<213> ORGANISM: Homo sapiens

<400> SEQUENCE: 151

```
caaggcaaac ttgaccaata gtcttagagt atccagtgag gccaggggcc ggcggctggc    60
tagggatgaa gaataaaagg aagcacccct cagcagttcc acacactcgc ttctggaacg   120
tctgaggtta tcaataagct cctagtccag acgccatggg tcatttcaca gaggaggaca   180
aggctactat cacaagcctg tggggcaagg tgaatgtgga agatgctgga ggagaaaccc   240
tgggaaggta ggctctggtg accaggacaa gggagggaag gaaggaccct gtgcctggca   300
```

<210> SEQ ID NO 152
<211> LENGTH: 300
<212> TYPE: DNA
<213> ORGANISM: Homo sapiens

<400> SEQUENCE: 152

```
caaggcaaac ttgaccaata gtcttagagt atccagtgag gccaggggcc ggcggctggc    60
tagggatgaa gaataaaagg aagcacccct cagcagttcc acacactcgc ttctggaacg   120
tctgaggtta tcaataagct cctagtccag acgccatggg tcatttcaca gaggaggaca   180
aggctactat cacaagcctg tggggcaagg tgaatgtgga agatgctgga ggagaaaccc   240
tgggaaggta ggctctggtg accaggacaa gggagggaag gaaggaccct gtgcctggca   300
```

<210> SEQ ID NO 153
<211> LENGTH: 7
<212> TYPE: PRT
<213> ORGANISM: Artificial Sequence
<220> FEATURE:
<223> OTHER INFORMATION: Description of Artificial Sequence: Synthetic
    peptide

<400> SEQUENCE: 153

Gln Ser Gly Thr Arg Lys Thr
1               5

<210> SEQ ID NO 154
<211> LENGTH: 7

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 154

Arg Ser Asp Asn Leu Ser Thr
1               5

<210> SEQ ID NO 155
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 155

Asp Ser Ala Asn Arg Ile Lys
1               5

<210> SEQ ID NO 156
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 156

Ala Met Gln Thr Leu Arg Val
1               5

<210> SEQ ID NO 157
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 157

Arg Asn Ser Asp Arg Thr Lys
1               5

<210> SEQ ID NO 158
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 158
atcaaggtta caagacaggt ttaaggag                                              28

<210> SEQ ID NO 159
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 159
aatctgccca gggcctcacc accaactt                                              28
```

<210> SEQ ID NO 160
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 160
ctccagaagg ggatcatgac ctcctcac                                        28

<210> SEQ ID NO 161
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 161

Leu Arg Gln Asn Leu Ile Met
1               5

<210> SEQ ID NO 162
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 162

Thr Ser Ala Asn Leu Thr Val
1               5

<210> SEQ ID NO 163
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 163

Gln Arg Asn Asp Arg Lys Ser
1               5

<210> SEQ ID NO 164
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 164

Leu Gln Ser Gln Leu Asn Arg
1               5

<210> SEQ ID NO 165
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 165

```
Asp Arg Ala Asn Leu Ser Arg
1               5
```

<210> SEQ ID NO 166
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 166

```
Thr Ser Ser Asn Arg Asn His
1               5
```

<210> SEQ ID NO 167
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 167

```
His Ser Gly Asn Leu Thr Lys
1               5
```

<210> SEQ ID NO 168
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 168

```
Gln Lys Val Asp Leu Ser Arg
1               5
```

<210> SEQ ID NO 169
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 169

```
Gln Ala Asn Asn Leu Lys Val
1               5
```

<210> SEQ ID NO 170
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 170

```
cccaacgggc cgtggtctgg ttcatcat                                          28
```

<210> SEQ ID NO 171
<211> LENGTH: 7
<212> TYPE: PRT
<213> ORGANISM: Artificial Sequence
<220> FEATURE:

```
<223> OTHER INFORMATION: Description of Artificial Sequence: Synthetic
      peptide

<400> SEQUENCE: 171

Arg Ser Asp Ser Leu Ser Arg
1               5

<210> SEQ ID NO 172
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 172

Asp Arg Ser Val Arg Thr Lys
1               5

<210> SEQ ID NO 173
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 173

Gln Arg Ser Asn Leu Lys Val
1               5

<210> SEQ ID NO 174
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 174

Arg Ser Asp His Leu Thr Thr
1               5

<210> SEQ ID NO 175
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 175

Trp Ala Thr Ala Arg Asp Arg
1               5

<210> SEQ ID NO 176
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 176

His Thr Lys Ser Leu Ser Arg
1               5
```

```
<210> SEQ ID NO 177
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 177

Arg Ser Ala His Leu Thr Gln
1               5

<210> SEQ ID NO 178
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 178

Asp Arg Ser Val Leu Arg Arg
1               5

<210> SEQ ID NO 179
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 179
atattgcaga caataacccc tttaacct                                         28

<210> SEQ ID NO 180
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 180

His Arg Trp Leu Arg Ser Asn
1               5

<210> SEQ ID NO 181
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 181

Asp Ser Ser His Arg Thr Arg
1               5

<210> SEQ ID NO 182
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 182
```

Gln Ser Ala His Leu Lys Ala
1               5

<210> SEQ ID NO 183
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 183
ctcactgtcc acaggagaag ccacacgg                                          28

<210> SEQ ID NO 184
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 184

Arg Ser Ala Asn Leu Ala Arg
1               5

<210> SEQ ID NO 185
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 185

Arg Leu Asp Asn Arg Thr Ala
1               5

<210> SEQ ID NO 186
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 186

Gln Ser Asn Asp Leu Asn Ser
1               5

<210> SEQ ID NO 187
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 187

Trp Arg Ser Ser Leu Lys Thr
1               5

<210> SEQ ID NO 188
<211> LENGTH: 7
<212> TYPE: PRT
<213> ORGANISM: Artificial Sequence
<220> FEATURE:
<223> OTHER INFORMATION: Description of Artificial Sequence: Synthetic -continued peptide

<400> SEQUENCE: 188

Asp Arg Ser Asn Arg Lys Thr
1               5

<210> SEQ ID NO 189
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 189
ttgctacagt tcttgaagac tttcccac                                          28

<210> SEQ ID NO 190
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 190

Tyr Lys His Val Leu Ser Asp
1               5

<210> SEQ ID NO 191
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 191

Thr Ser Gly Ser Leu Thr Arg
1               5

<210> SEQ ID NO 192
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 192

Leu Lys Asp Thr Leu Arg Arg
1               5

<210> SEQ ID NO 193
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 193
gagaagccac acgggcgaaa ggccttat                                          28

<210> SEQ ID NO 194
<211> LENGTH: 7
<212> TYPE: PRT

```
<213> ORGANISM: Artificial Sequence
<220> FEATURE:
<223> OTHER INFORMATION: Description of Artificial Sequence: Synthetic
      peptide

<400> SEQUENCE: 194

Gln Ser Gly Asn Leu Asp Ser
1               5

<210> SEQ ID NO 195
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 195

Gln Asn Ala Thr Arg Ile Asn
1               5

<210> SEQ ID NO 196
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 196

Trp Asn Ser Asp Leu Arg Lys
1               5

<210> SEQ ID NO 197
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 197
tggacagtga gattgctaca gttcttga                                            28

<210> SEQ ID NO 198
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 198

Tyr Lys Trp Thr Leu Arg Asn
1               5

<210> SEQ ID NO 199
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 199

Thr Ser Thr Lys Leu Arg Thr
1               5
```

<210> SEQ ID NO 200
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 200
gccacacggg cgaaaggcct tataaatg                                          28

<210> SEQ ID NO 201
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 201

Arg Ser Asp Thr Leu Ser Thr
1               5

<210> SEQ ID NO 202
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 202

Asp Ser Ser Asn Arg Ile Asn
1               5

<210> SEQ ID NO 203
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 203
ctcctgtgga cagtgagatt gctacagt                                          28

<210> SEQ ID NO 204
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 204

Asn Asp Leu Phe Leu Tyr Leu
1               5

<210> SEQ ID NO 205
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 205

```
Arg Ser Asp Ser Leu Ser Val
1               5
```

<210> SEQ ID NO 206
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 206

```
His Asn Asp Ser Arg Lys Asn
1               5
```

<210> SEQ ID NO 207
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 207
aagctcacca ggcacatgaa aacgcatg                                          28

<210> SEQ ID NO 208
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 208

```
Cys Arg Gln Asn Leu Ala Asn
1               5
```

<210> SEQ ID NO 209
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 209

```
Tyr Gln Gly Val Leu Thr Arg
1               5
```

<210> SEQ ID NO 210
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 210

```
His Arg Ser Ser Leu Arg Arg
1               5
```

<210> SEQ ID NO 211
<211> LENGTH: 28
<212> TYPE: DNA
<213> ORGANISM: Artificial Sequence
<220> FEATURE:
<223> OTHER INFORMATION: Description of Artificial Sequence: Synthetic -continued oligonucleotide

<400> SEQUENCE: 211
ctactctggg cacaggcata gttgcaca                                        28

<210> SEQ ID NO 212
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 212

Arg Ser Asp Ala Leu Ser Glu
1               5

<210> SEQ ID NO 213
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 213
ctcaccaggc acatgaaaac gcatggcc                                        28

<210> SEQ ID NO 214
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 214

Gly Ser Ser Ala Leu Thr Gln
1               5

<210> SEQ ID NO 215
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 215

Thr Ala Ser His Leu Lys Glu
1               5

<210> SEQ ID NO 216
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 216

Ser Ser Arg Asn Leu Ala Ser
1               5

<210> SEQ ID NO 217
<211> LENGTH: 7
<212> TYPE: PRT

```
<213> ORGANISM: Artificial Sequence
<220> FEATURE:
<223> OTHER INFORMATION: Description of Artificial Sequence: Synthetic
      peptide

<400> SEQUENCE: 217

Thr Ser Ala Asn Leu Ser Arg
1               5

<210> SEQ ID NO 218
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 218
ggtgaggagg agatccaggt cccaggtg                                          28

<210> SEQ ID NO 219
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 219

Asn Asn Arg Asp Leu Ile Asn
1               5

<210> SEQ ID NO 220
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 220

Thr Ser Ser Asn Leu Ser Arg
1               5

<210> SEQ ID NO 221
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 221

Gln Arg Thr His Leu Asn Ser
1               5

<210> SEQ ID NO 222
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 222
cttctcgggc ccggagcccg gtggcgcg                                          28
```

```
<210> SEQ ID NO 223
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 223

Arg Lys Ser Asp Arg Ile Lys
1               5

<210> SEQ ID NO 224
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 224
tggtcaaggc aaggctggcc aacccatg                                        28

<210> SEQ ID NO 225
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 225
gccttgacaa ggcaaacttg accaatag                                        28

<210> SEQ ID NO 226
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 226

Gln Ser Gly Ser Leu Thr Arg
1               5

<210> SEQ ID NO 227
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 227

Arg Ser Asp Asn Leu Ser Val
1               5

<210> SEQ ID NO 228
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 228

Leu Lys Phe Ala Leu Ala Asn
```

<210> SEQ ID NO 229
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 229

Asn Pro Ala Asn Leu Thr Arg
1               5

<210> SEQ ID NO 230
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 230

Asp Ser Ser Ala Arg Lys Lys
1               5

<210> SEQ ID NO 231
<211> LENGTH: 39
<212> TYPE: DNA
<213> ORGANISM: Homo sapiens

<400> SEQUENCE: 231
accatggtgc acctgactcc tgaggagaag tctgccgtt                              39

<210> SEQ ID NO 232
<211> LENGTH: 39
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 232
accatggtgc atctgactcc tgaggaaaaa agcgctgtg                              39

<210> SEQ ID NO 233
<211> LENGTH: 88
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 233
cgttcacctt gccccacagg gcagtaacag cagattttc ctcaggagtc aggtgcacca       60
tggtgtctgt ttgaggttgc tagtgaac                                         88

<210> SEQ ID NO 234
<211> LENGTH: 88
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 234

```
cgttcaccttt gccccacagg gcagtaacgg cagattttc ctcaggagtc aggtgcacca        60
tggtgtctgt ttgaggttgc tagtgaac                                          88
```

<210> SEQ ID NO 235
<211> LENGTH: 101
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 235

```
cttcatccac gttcaccttg ccccacaggg cagtaacagc agattttcc tcaggagtca        60 ggtgcaccat ggtgtctgtt tgaggttgct agtgaacaca g                          101
```

<210> SEQ ID NO 236
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 236

```
ctgtgggcag tgccagatga                                                   20
```

<210> SEQ ID NO 237
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 237

```
rtrrrcartr ccarat                                                       16
```

<210> SEQ ID NO 238
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 238

```
ctcgataaaa ataagaatgt                                                   20
```

<210> SEQ ID NO 239
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (16)..(16)
<223> OTHER INFORMATION: a, c, t or g

<400> SEQUENCE: 239

```
crataaaaat aaraang                                                      17
```

<210> SEQ ID NO 240
<211> LENGTH: 21
<212> TYPE: DNA

```
<213> ORGANISM: Artificial Sequence
<220> FEATURE:
<223> OTHER INFORMATION: Description of Artificial Sequence: Synthetic
      oligonucleotide

<400> SEQUENCE: 240
atgtccttcc cagccacctc t                                                  21

<210> SEQ ID NO 241
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 241
rtccttccca rccacct                                                       17

<210> SEQ ID NO 242
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 242
gttaaagggg ttattgtct                                                     19

<210> SEQ ID NO 243
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 243
taaarrrrtt attrt                                                         15

<210> SEQ ID NO 244
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 244

His Thr Lys Ile His Leu Arg Gly Ser Gln Leu Val Lys Ser Lys Ser
1               5                   10                  15

Glu Ala Ala Ala Arg
            20

<210> SEQ ID NO 245
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 245

His Thr Lys Ile His Leu Arg Gly Ser Tyr Ala Pro Met Pro Pro Leu
1               5                   10                  15
```

Ala Leu Ala Ser Pro
            20

<210> SEQ ID NO 246
<211> LENGTH: 124
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 246
acactatctc aatgcaaata tctgtctgaa acggtccctg gctaaactcc acccatgggt      60
tggccagcct tgccttgaca aggcaaactt gaccaatagt cttagagtat ccagtgaggc     120
cagg                                                                 124

<210> SEQ ID NO 247
<211> LENGTH: 124
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 247
cctggcctca ctggatactc taagactatt ggtcaagttt gccttgtcaa ggcaaggctg      60
gccaacccat gggtggagtt tagccaggga ccgtttcaga cagatatttg cattgagata     120
gtgt                                                                 124

<210> SEQ ID NO 248
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 248
gttggccagc cttgccttga c                                               21

<210> SEQ ID NO 249
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 249
trrccarcct trccttg                                                    17

<210> SEQ ID NO 250
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 250
ttggtcaagt ttgccttgtc a                                               21

<210> SEQ ID NO 251
<211> LENGTH: 17

```
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 251 rrtcaartt tccttrt                                                          17

<210> SEQ ID NO 252
<211> LENGTH: 9
<212> TYPE: PRT
<213> ORGANISM: Unknown
<220> FEATURE:
<223> OTHER INFORMATION: Description of Unknown: 'LAGLIDADG'
      family peptide

<400> SEQUENCE: 252

Leu Ala Gly Leu Ile Asp Ala Asp Gly
1               5

<210> SEQ ID NO 253
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 253
catcccaggc gtggggatta gagctcca                                             28

<210> SEQ ID NO 254
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 254
gtatcctctt gggggccc                                                        18

<210> SEQ ID NO 255
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 255
atatttgcat tgagatagt                                                       19

<210> SEQ ID NO 256
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 256
gtatcctctt gggggcccc                                                       19

<210> SEQ ID NO 257
<211> LENGTH: 18
```

```
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 257
atatttgcat tgagatag                                                     18

<210> SEQ ID NO 258
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 258
atttrcattr arata                                                        15
```